(12) United States Patent
Morie et al.

(10) Patent No.: US 7,767,854 B2
(45) Date of Patent: Aug. 3, 2010

(54) N-SUBSTITUTED PHENYLACETAMIDE DERIVATIVE AND PHARMACEUTICAL COMPOSITION CONTAINING THE SAME

(75) Inventors: Toshiya Morie, Suita (JP); Yasunori Tsuzuki, Suita (JP); Keiji Adachi, Suita (JP); Kazuhiro Mizuno, Suita (JP); Katsuyoshi Kawashima, Suita (JP); Isao Shimizu, Suita (JP); Daisuke Ishii, Suita (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 464 days.

(21) Appl. No.: 11/918,942

(22) PCT Filed: Apr. 20, 2006

(86) PCT No.: PCT/JP2006/308311

§ 371 (c)(1),
(2), (4) Date: Oct. 22, 2007

(87) PCT Pub. No.: WO2006/115168

PCT Pub. Date: Nov. 2, 2006

(65) Prior Publication Data

US 2009/0082463 A1 Mar. 26, 2009

(30) Foreign Application Priority Data

Apr. 21, 2005 (JP) ............................. 2005-123549

(51) Int. Cl.
C07C 233/05 (2006.01)
A61K 31/165 (2006.01)

(52) U.S. Cl. ............... 564/182; 564/175; 514/617; 514/622

(58) Field of Classification Search ............ 564/175, 564/182; 514/617, 622
See application file for complete search history.

(56) References Cited

U.S. PATENT DOCUMENTS

| 5,013,759 | A | 5/1991 | Berman et al. |
| 5,344,845 | A | 9/1994 | Koda et al. |
| 2004/0248983 | A1 | 12/2004 | Morie et al. |

FOREIGN PATENT DOCUMENTS

| JP | 62-48657 | 3/1987 |
| JP | 5-148202 | 6/1993 |
| WO | 02/100819 | 12/2002 |

OTHER PUBLICATIONS

International Serach Report issued Jul. 11, 2006 in the International (PCT) Application PCT/JP2006/308311 of which the present application is the U.S. National Stage.

Primary Examiner—Shailendra Kumar
(74) Attorney, Agent, or Firm—Wenderoth, Lind & Ponack, L.L.P.

(57) ABSTRACT

The invention provides the following compound (I):

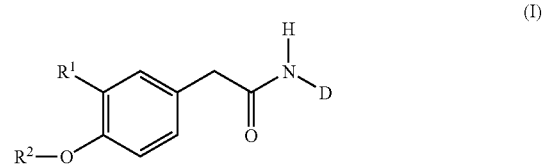

wherein $R^1$ is methoxy group, hydroxyl group or hydrogen atom; $R^2$ is hydrogen atom, $C_{1-4}$ alkyl group, $C_{1-4}$ alkylcarbonyl group or arylcarbonyl group; D is a group of the following formula (A), (B), or (C).

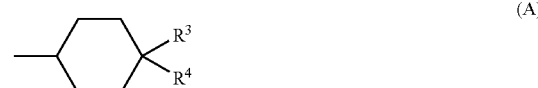

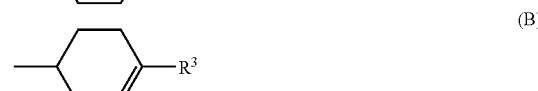

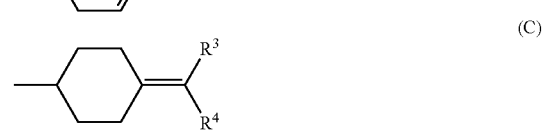

The compound is useful as a medicament for treating neuropathic pain or pain caused by various diseases such as rheumatoid arthritis and osteoarthritis, and inflammation.

24 Claims, No Drawings

N-SUBSTITUTED PHENYLACETAMIDE DERIVATIVE AND PHARMACEUTICAL COMPOSITION CONTAINING THE SAME

TECHNICAL FIELD

The present invention relates to an N-substituted phenylacetamide derivative which is a useful medicament for treating pain and inflammation, and a pharmaceutical composition containing the same.

BACKGROUND OF THE INVENTION

In these days, narcotic analgesic agents such as morphine, nonnarcotic analgesic agents such as NSAIDs (Non-Steroidal Anti-Inflammatory Drugs) have been mainly used as an analgesic agent. However, the use of the narcotic analgesic agent is strictly limited because of its tolerance/addiction or other severe side-effects, and the NSAIDs are not effective against severe pain and also cause upper gastrointestinal disorders or liver toxicities with a high possibility by long-term administration thereof. Therefore, it has been desired to develop a novel analgesic agent that exhibits higher analgesic action with fewer side-effect. Furthermore, an analgesic agent that exhibits a fully-satisfied efficacy for neuropathic pain such as diabetic neuropathic pain, postherpetic neuralgia, trigeminal neuralgia, and HIV-multiple neuropathic pain had not been found yet, and thus it has been expected to develop a useful medicament for treating such diseases.

Capsaicin [(E)-8-methyl-N-vanillyl-6-nonenamide] which is contained in the juice of chili peppers is not used only as a spice, but also known as a material exhibiting analgesic action and anti-inflammation action. In addition, civamide [(Z)-8-methyl-N-vanillyl-6-nonenamide] which is a geometrical isomer of capsaicin is also known as a material exhibiting analgesic action. It has been thought that capsaicin acts specifically on an especial receptor in the primary afferent sensory neuron (mainly C-fiber: capsaicin sensitive neuron) to induce analgesic action and anti-inflammation action as well as strong irritancy (pain) Recently, the receptor was cloned and named as vanilloid receptor subtype 1 (VR$^1$) [Nature, 389, 816 (1997)]. After that, the receptor was classified into TRPVs, one of the TRP (transient receptor potential) superfamily, and is also called TRPV1 [Annu. Rev. Neurosci., 24, 487 (2001)].

TRPV1 is thought to be a high $Ca^{2+}$-permeable cation channel with six-transmembrane domains according to the amino acid sequence thereof and thus it is supposed that TRPV1 is activated by not only a capsaicin-like compound, but also by heat stimulation, proton, etc., and that TRPV1 is related with various type of pain. When capsaicin acts on TRPV1 in the primary afferent sensory neuron; the cation channel thereof is opened, the membrane is depolarized and then neuropeptides such as Substance P are released, then pain is caused. The reason why capsaicin has been actually used for the treatment of pain such as diabetic neuropathy and rheumatoid arthritis in spite of the painful irritancy of capsaicin is thought to be because capsaicin continuously has TRPV1 cation channel open and thereby the sensory neuron becomes non-reactive for pain (desensitization) [Pharmacol. Rev. 51, 159 (1999)].

Thus, it is thought that a capsaicin-like compound (TRPV1 agonist) can exert analgesic effect via new pharmaceutical mechanism (desensitization of capsaicin-sensitive sensory neuron) that is completely different from that of conventional analgesic agents. Therefore, a capsaicin-like compound is expected to become a useful medicament for treating neuropathic pain or other various types of pain caused by various diseases such as rheumatoid arthritis and osteoarthritis, which are not fully cured with existing analgesic agents.

In the U.S., now an analgesic agent comprising capsaicin has been sold as a cream formulation. However, the capsaicin cream formulation is disadvantageous in its strong painful irritancy just after administered. Therefore, it has been especially desired to develop a medicine for treating neuropathic pain or other types of pain such as rheumatoid arthritis and osteoarthritis, which has the capsaicin-like mechanism and can exert a sufficient analgesic effect with low irritancy.

In addition, it is thought that a compound having the capsaicin-like pharmacological mechanism is useful as a medicament for treating pruritus that is relevant disease to the primary afferent sensory neuron(C-fiber), allergic and nonallergic rhinitis, overactive bladder, stroke, irritable bowel syndrome, respiratory disease (such as asthma/chronic obstructive pulmonary disease), dermatitis, mucositis, gastric/duodenal ulcer and inflammatory bowel syndrome.

Furthermore, it is also thought that a compound having the capsaicin-like pharmacological mechanism may be useful as a medicament for treating obesity, since it is reported that capsaicin can promote the adrenaline secretion to exhibit an anti-obesity activity [Pharmacol. Rev., 38, 179 (1986)]. In addition, it is also thought that the compound may be useful as a medicament for treating diabetes, since it is reported that diabetic rats were improved at the insulin resistance by the treatment for capsaicin [Eur. J Endocrinol., 153, 963, (2005)].

WO 02/100819 discloses that N-arylphenylacetamide derivatives has an analgesic action, however, the derivatives are quite different in chemical structure from the compound (I) of the present invention, namely, it is essential that the compound of the present invention is bound to cyclohexyl or cyclohexenyl group on the nitrogen atom of the acetamide, while it is essential that the compounds of the reference is bound to aryl such as phenyl on the corresponding position.

In addition, Arzneim.-Forsch., 25, 1877 (1975) discloses that the following compound exhibits a little lower irritancy than capsaicin.

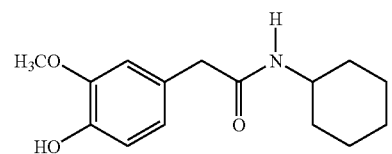

And, Arzneim.-Forsch., 26, 33 (1976) (page 35, left column, lines 10 to 14; and FIG. 4) discloses that said compound exhibits a strong stimulatory but it exhibits a weak desensitization. Further, WO 92/18463 (Example 127) discloses N-substituted phenylacetamide compound having the following structure.

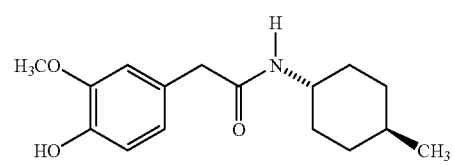

However, the above two compounds are different from the below-mentioned present compound of the formula (I) from the viewpoints of the chemical structure of the substituent on the cyclohexane ring and also the pharmacological activity, i.e. the above two compounds exhibits little analgesic effect that the compound of the invention exhibits.

DISCLOSURE OF INVENTION

Problem to be Solved by the Invention

A problem to be solved by the invention is to provide a compound that exhibits a potent analgesic action but a low irritancy, which is useful as a medicament for treating neuropathic pain or pain caused by various diseases such as rheumatoid arthritis and osteoarthritis, and inflammation.

Means to Solve the Problem

The present inventors have intensively studied in order to solve the above-mentioned problems, and have found that a phenylacetamide derivative of the following formula (I) which is bound on its nitrogen atom with a cyclohexyl group or cyclohexenyl group that has a specific substituent exhibits a potent analgesic action but a low irritancy, and they have accomplished the present invention. That is, the present invention relates to the following embodiments:

[1] A N-substituted phenylacetamide derivative of the formula (I):

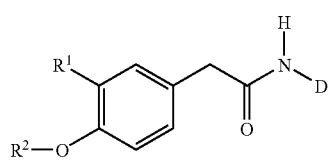

wherein
$R^1$ is a methoxy group, a hydroxyl group, or a hydrogen atom;
$R^2$ is a hydrogen atom, a $C_{1-4}$ alkyl group, a $C_{1-4}$ alkylcarbonyl group, or an arylcarbonyl group; and
D is a group of the following formula (A), (B), or (C):

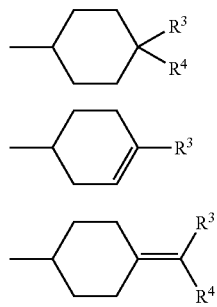

wherein
$R^3$ is defined as a group of —X—Y—Z, wherein
X is a single bond, a $C_{1-10}$ alkylene group, a $C_{2-10}$ alkenylene group or a $C_{2-10}$ alkynylene group;
Y is a single bond, —O—, —O—C(=O)—, —C(=O)—, or C(=O)—O—;
Z is a straight or branched hydrocarbon group selected from the group consisting of a $C_{1-10}$ alkyl group, a $C_{2-10}$ alkenyl group, a $C_{2-10}$ alkynyl group, and a $C_{4-10}$ alkenylalkynyl group, in which the hydrocarbon may be optionally substituted with a $C_{3-8}$ cycloalkyl or an aryl; or a cyclic group selected from the group consisting of a $C_{3-8}$ cycloalkyl group, a $C_{3-8}$ cycloalkylidene-$C_{1-3}$ alkyl group, and an aryl group;

the alkylene group, the alkenylene group, the alkynylene group, the alkyl group, the alkenyl group, the alkynyl group, and the alkenylalkynyl group in the above X and Z may be optionally substituted with 1-5 substituents selected from the group consisting of fluorine atoms and hydroxyl groups;

the cycloalkyl group and the cycloalkyl moiety in the above Z may be optionally substituted with 1-5 substituents selected from the group consisting of fluorine atoms, hydroxyl groups, and $C_{1-6}$ alkyl groups;

the aryl group and the aryl moiety in the above Z may be optionally substituted with 1-5 substituents selected from the group consisting of fluorine atoms, hydroxyl groups, $C_{1-6}$ alkyl groups optionally substituted with 1-5 fluorine atoms, $C_{1-6}$ alkoxy groups optionally substituted with 1-5 fluorine atoms, nitro groups, amino groups, cyano groups, $C_{1-4}$ alkyloxycarbonyl groups, $C_{1-4}$ alkylcarbonyloxy groups, carboxyl groups, and methylenedioxy groups;

provided that X is a single bond when Y is a single bond; both X and Y are a single bond when Z is a $C_{3-8}$ cycloalkylidene-$C_{1-3}$ alkyl group; or X is a $C_{1-10}$ alkylene group when Y in the formula (B) or (C) is —O—;

$R^4$ is a hydrogen atom, a hydroxyl group, a $C_{1-4}$ alkyl group, a $C_{2-4}$ alkenyl group, or a $C_{2-4}$ alkynyl group, provided that $R^4$ in formula (C) is not a hydroxyl group; alternatively $R^3$ and $R^4$ are taken together to form a $C_{3-8}$ cycloalkyl group or a saturated $C_{3-8}$ heteromonocyclyl group containing 1 or 2 oxygen atoms, each of which may be optionally substituted with 1-5 $C_{1-6}$ alkyl groups;

further provided that $R^3$ and $R^4$ in formula (A) contain at least 3 carbon atoms in total; $R^3$ in formula (B) contains at least 3 carbon atoms; and $R^3$ and $R^4$ in formula (C) contain at least 2 carbon atoms in total, or a physiologically acceptable salt thereof.

[2] The N-substituted phenylacetamide derivative of the above [1] wherein
$R^1$ is a methoxy group, a hydroxyl group, or a hydrogen atom;
$R^2$ is a hydrogen atom, a $C_{1-4}$ alkyl group, a $C_{1-4}$ alkylcarbonyl group, or an arylcarbonyl group; and
D is a group of the following formula (A), (B), or (C):

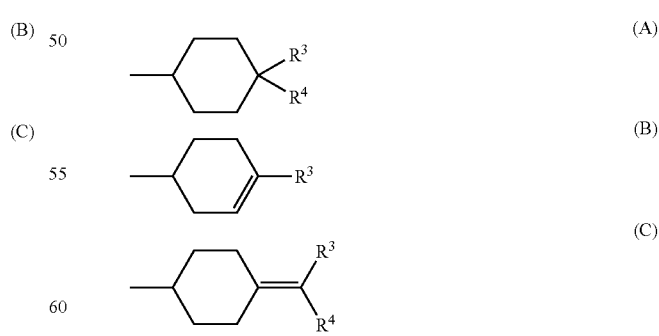

wherein
$R^3$ is defined as a group of —X—Y—Z, wherein
X is a single bond, a $C_{1-10}$ alkylene group, or a $C_{2-10}$ alkenylene group;

Y is a single bond, —O—, —O—C(=O)—, —C(=O)—, or —C(=O)—O—;

Z is a straight or branched hydrocarbon group selected from the group consisting of a $C_{1-10}$ alkyl group, a $C_{2-10}$ alkenyl group, a $C_{2-10}$ alkynyl group, and a $C_{4-10}$ alkenylalkynyl group, in which the hydrocarbon may be optionally substituted with a $C_{3-8}$ cycloalkyl or an aryl; or a cyclic group selected from the group consisting of a $C_{3-8}$ cycloalkyl group, a $C_{3-8}$ cycloalkylidene-$C_{1-3}$ alkyl group, and an aryl group;

the alkylene group, the alkenylene group, the alkyl group, the alkenyl group, the alkynyl group, and the alkenylalkynyl group in the above X and Z may be optionally substituted with 1-5 substituents selected from the group consisting of fluorine atoms and hydroxyl groups;

the cycloalkyl group and the cycloalkyl moiety in the above Z may be optionally substituted with 1-5 substituents selected from the group consisting of fluorine atoms, hydroxyl groups, and $C_{1-6}$ alkyl groups;

the aryl group and the aryl moiety in the above Z may be optionally substituted with 1-5 substituents selected from the group consisting of fluorine atoms, hydroxyl groups, $C_{1-6}$ alkyl groups optionally substituted with 1-5 fluorine atoms, $C_{1-6}$ alkoxy groups optionally substituted with 1-5 fluorine atoms, nitro groups, amino groups, cyano groups, $C_{1-4}$ alkyloxycarbonyl groups, $C_{1-4}$ alkylcarbonyloxy groups, carboxyl groups, and methylenedioxy groups;

provided that X is a single bond when Y is a single bond; both X and Y are a single bond when Z is a $C_{3-8}$ cycloalkylidene-$C_{1-3}$ alkyl group; or X is a $C_{1-10}$ alkylene group when Y in the formula (B) or (C) is —O—;

$R^4$ is a hydrogen atom, a hydroxyl group, a $C_{1-4}$ alkyl group, a $C_{2-4}$ alkenyl group, or a $C_{2-4}$ alkynyl group, provided that $R^4$ in formula (C) is not a hydroxyl group; alternatively $R^3$ and $R^4$ are taken together to form a $C_{3-8}$ cycloalkyl group or a saturated $C_{3-8}$ heteromonocyclyl group containing 1 or 2 oxygen atoms, each of which may be optionally substituted with 1-5 $C_{1-6}$ alkyl groups;

further provided that $R^3$ and $R^4$ in formula (A) contain at least 3 carbon atoms in total; $R^3$ in formula (B) contains at least 3 carbon atoms; and $R^3$ and $R^4$ in formula (C) contain at least 2 carbon atoms in total, or a physiologically acceptable salt thereof.

[3] The N-substituted phenylacetamide derivative of the above [1] wherein $R^1$ is a methoxy group, a hydroxyl group, or a hydrogen atom;

$R^2$ is a hydrogen atom, a $C_{1-4}$ alkyl group, a $C_{1-4}$ alkylcarbonyl group, or an arylcarbonyl group; and D is a group of the following formula (A), (B), or (C):

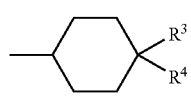

(A)

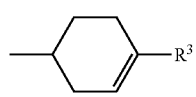

(B)

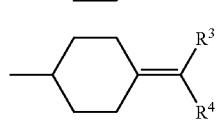

(C)

wherein $R^3$ is defined as a group of —X—Y—Z, wherein

X is a single bond, a $C_{1-10}$ alkylene group, or a $C_{2-10}$ alkenylene group;

Y is a single bond, —O—, —O—C(=O)—, —C(=O)—, or —C(=O)—O—;

Z is a straight or branched hydrocarbon group selected from the group consisting of a $C_{1-10}$ alkyl group and a $C_{2-10}$ alkenyl group, in which the hydrocarbon may be optionally substituted with a $C_{3-8}$ cycloalkyl or an aryl; or a cyclic group selected from the group consisting of a $C_{3-8}$ cycloalkyl group, a $C_{3-8}$ cycloalkylidene-$C_{1-3}$ alkyl group, and an aryl group;

the alkylene group, the alkenylene group, the alkyl group, and the alkenyl group in the above X and Z may be optionally substituted with 1-5 substituents selected from the group consisting of fluorine atoms and hydroxyl groups;

the cycloalkyl group and the cycloalkyl moiety in the above Z may be optionally substituted with 1-5 substituents selected from the group consisting of fluorine atoms, hydroxyl groups, and $C_{1-6}$ alkyl groups;

the aryl group and the aryl moiety in the above Z may be optionally substituted with 1-5 substituents selected from the group consisting of fluorine atoms, hydroxyl groups, $C_{1-6}$ alkyl groups optionally substituted with 1-5 fluorine atoms, $C_{1-6}$ alkoxy groups optionally substituted with 1-5 fluorine atoms, nitro groups, amino groups, cyano groups, $C_{1-4}$ alkyloxycarbonyl groups, $C_{1-4}$ alkylcarbonyloxy groups, carboxyl groups, and methylenedioxy groups;

provided that X is a single bond when Y is a single bond; both X and Y are a single bond when Z is a $C_{3-8}$ cycloalkylidene-$C_{1-3}$ alkyl group; or X is a $C_{1-10}$ alkylene group when Y in the formula (B) or (C) is —O—;

$R^4$ is a hydrogen atom, a hydroxyl group, a $C_{1-4}$ alkyl group, a $C_{2-4}$ alkenyl group, or a $C_{2-4}$ alkynyl group, provided that $R^4$ in formula (C) is not a hydroxyl group; alternatively $R^3$ and $R^4$ are taken together to form a $C_{3-8}$ cycloalkyl group or a saturated $C_{3-8}$ heteromonocyclyl group containing 1 or 2 oxygen atoms, each of which may be optionally substituted with 1-5 $C_{1-6}$ alkyl groups;

further provided that $R^3$ and $R^4$ in formula (A) contain at least 3 carbon atoms in total; $R^3$ in formula (B) contains at least 3 carbon atoms; and $R^3$ and $R^4$ in formula (C) contain at least 2 carbon atoms in total, or a physiologically acceptable salt thereof.

[4] The N-substituted phenylacetamide derivative of the above [1] wherein $R^1$ is a methoxy group, a hydroxyl group, or a hydrogen atom;

$R^2$ is a hydrogen atom, a $C_{1-4}$ alkyl group, a $C_{1-4}$ alkylcarbonyl group, or an arylcarbonyl group; and D is a group of the following formula (A), (B), or (C):

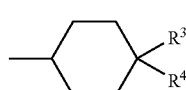

(A)

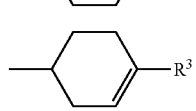

(B)

-continued

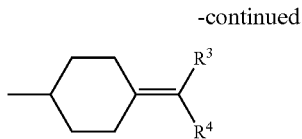

wherein

R³ is defined as a group of —X—Y—Z, wherein

X is a single bond, a $C_{1-10}$ alkylene group, or a $C_{2-10}$ alkenylene group;

Y is a single bond, —O—, —O—C(=O)—, —C(=O)—, or —C(=O)—O—;

Z is a straight or branched hydrocarbon group selected from the group consisting of a $C_{1-10}$ alkyl group and a $C_{2-10}$ alkenyl group, in which the hydrocarbon may be optionally substituted with a $C_{3-8}$ cycloalkyl or an aryl; or a cyclic group selected from the group consisting of a $C_{3-8}$ cycloalkyl group, a $C_{3-8}$ cycloalkylidene-$C_{1-3}$ alkyl group, and an aryl group;

the alkylene group, the alkenylene group, the alkyl group, and the alkenyl group in the above X and Z may be optionally substituted with 1-5 substituents selected from the group consisting of fluorine atoms and hydroxyl groups;

the cycloalkyl group and the cycloalkyl moiety in the above Z may be optionally substituted with 1-5 substituents selected from the group consisting of fluorine atoms, hydroxyl groups, and $C_{1-6}$ alkyl groups;

the aryl group and the aryl moiety in the above Z may be optionally substituted with 1-5 substituents selected from the group consisting of fluorine atoms, hydroxyl groups, $C_{1-6}$ alkyl groups optionally substituted with 1-5 fluorine atoms, $C_{1-6}$ alkoxy groups optionally substituted with 1-5 fluorine atoms, nitro groups, amino groups, cyano groups, $C_{1-4}$ alkyloxycarbonyl groups, $C_{1-4}$ alkylcarbonyloxy groups, carboxyl groups, and methylenedioxy groups;

provided that X is a single bond when Y is a single bond; both X and Y are a single bond when Z is a $C_{3-8}$ cycloalkylidene-$C_{1-3}$ alkyl group; or X is a $C_{1-10}$ alkylene group when Y in the formula (B) or (C) is —O—;

R⁴ is a hydrogen atom or a $C_{1-4}$ alkyl group; alternatively

R³ and R⁴ are taken together to form a $C_{3-8}$ cycloalkyl group or a saturated $C_{3-8}$ heteromonocyclyl group containing 1 or 2 oxygen atoms, each of which may be optionally substituted with 1-5 $C_{1-6}$ alkyl groups;

further provided that R³ and R⁴ in formula (A) contain at least 3 carbon atoms in total; R³ in formula (B) contains at least 3 carbon atoms; and R³ and R⁴ in formula (C) contain at least 2 carbon atoms in total, or a physiologically acceptable salt thereof.

[5] The N-substituted phenylacetamide derivative of the above [1] wherein R³ is defined as a group of —X—Y—Z, and X is a single bond; or a physiologically acceptable salt thereof.

[6] The N-substituted phenylacetamide derivative of the above [1] wherein R³ is defined as a group of —X—Y—Z, and Y is a single bond or —O—; or a physiologically acceptable salt thereof.

[7] The N-substituted phenylacetamide derivative of the above [1] wherein R³ is defined as a group of —X—Y—Z, and both X and Y are a single bond; or a physiologically acceptable salt thereof.

[8] The N-substituted phenylacetamide derivative of the above [1] wherein R³ and R⁴ are taken together to form a $C_{3-8}$ cycloalkyl group which may be optionally substituted with 1-5 $C_{1-6}$ alkyl groups; or a physiologically acceptable salt thereof.

[9] The N-substituted phenylacetamide derivative of the above [1] wherein R³ and R⁴ in formula (A) contain 3-10 carbon atoms in total, R³ in formula (B) contains 3-10 carbon atoms, and R³ and R⁴ in formula (C) contain 2-9 carbon atoms in total; or a physiologically acceptable salt thereof.

[10] The N-substituted phenylacetamide derivative of the above [1] wherein R³ and R⁴ in formula (A) contain 3-8 carbon atoms in total, R³ in formula (B) contains 3-8 carbon atoms, and R³ and R⁴ in formula (C) contain 2-7 carbon atoms in total; or a physiologically acceptable salt thereof.

[11] The N-substituted phenylacetamide derivative of the above [1] wherein

R¹ is a methoxy group, a hydroxyl group, or a hydrogen atom;

R² is a hydrogen atom, a $C_{1-4}$ alkyl group, a $C_{1-4}$ alkylcarbonyl group, or an arylcarbonyl group; and D is a group of the following formula (A), (B), or (C):

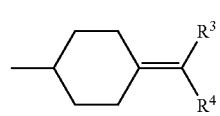

wherein

R³ is defined as a group of —X—Y—Z, wherein

X is a single bond;

Y is a single bond;

Z is a straight or branched hydrocarbon group selected from the group consisting of a $C_{1-7}$ alkyl group or a $C_{2-7}$ alkenyl group, in which the hydrocarbon may be optionally substituted with a $C_{3-8}$ cycloalkyl or an aryl; or a cyclic group selected from the group consisting of a $C_{3-8}$ cycloalkyl group, a $C_{3-8}$ cycloalkylidene-$C_{1-3}$ alkyl group, and an aryl group;

the alkyl group or alkenyl group in the above Z may be optionally substituted with 1-5 substituents selected from the group consisting of fluorine atoms and hydroxyl groups;

the cycloalkyl group and the cycloalkyl moiety in the above Z may be optionally substituted with 1-5 substituents selected from the group consisting of fluorine atoms, hydroxyl groups, and $C_{1-6}$ alkyl groups;

the aryl group and the aryl moiety in the above Z may be optionally substituted with 1-5 substituents selected from the group consisting of fluorine atoms, hydroxyl groups, $C_{1-6}$ alkyl groups optionally substituted with 1-5 fluorine atoms, $C_{1-6}$ alkoxy groups optionally substituted with 1-5 fluorine atoms, nitro groups, amino groups, cyano groups, $C_{1-4}$ alkyloxycarbonyl groups, $C_{1-4}$ alkylcarbonyloxy groups, carboxyl groups, and methylenedioxy groups;

R⁴ is a hydrogen atom or a $C_{1-4}$ alkyl group; alternatively

R³ and R⁴ are taken together to form a $C_{3-8}$ cycloalkyl group which may be optionally substituted with 1-5 $C_{1-6}$ alkyl groups;

further provided that $R^3$ and $R^4$ in formula (A) contain 3-10 carbon atoms in total; $R^3$ in formula (B) contains 3-10 carbon atoms; and $R^3$ and $R^4$ in formula (C) contain 2-9 carbon atoms in total, or a physiologically acceptable salt thereof.

[12] The N-substituted phenylacetamide derivative of the above [1] wherein $R^1$ is a methoxy group, a hydroxyl group, or a hydrogen atom;

$R^2$ is a hydrogen atom, a $C_{1-4}$ alkyl group, a $C_{1-4}$ alkylcarbonyl group, or an arylcarbonyl group; and D is a group of the following formula (A), (B), or (C):

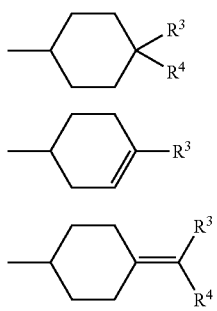

wherein $R^3$ is defined as a group of —X—Y—Z, wherein

X is a single bond;

Y is a single bond;

Z is a straight or branched hydrocarbon group selected from the group consisting of a $C_{1-7}$ alkyl group and a $C_{2-7}$ alkenyl group, in which the hydrocarbon may be optionally substituted with a $C_{3-8}$ cycloalkyl; or a cyclic group selected from the group consisting of a $C_{3-8}$ cycloalkyl group and a $C_{3-8}$ cycloalkylidene-$C_{1-3}$ alkyl group;

the alkyl group or alkenyl group in the above Z may be optionally substituted with 1-5 fluorine atoms;

$R^4$ is a hydrogen atom or a $C_{1-4}$ alkyl group; alternatively $R^3$ and $R^4$ are taken together to form a $C_{3-8}$ cycloalkyl group further provided that $R^3$ and $R^4$ in formula (A) contain 3-10 carbon atoms in total; $R^3$ in formula (B) contains 3-10 carbon atoms; and $R^3$ and $R^4$ in formula (C) contain 2-9 carbon atoms in total, or a physiologically acceptable salt thereof.

[13] The N-substituted phenylacetamide derivative of the above [1] wherein $R^1$ is a methoxy group or a hydroxyl group, or a physiologically acceptable salt thereof.

[14] The N-substituted phenylacetamide derivative of the above [1] wherein $R^2$ is a hydrogen atom, or a physiologically acceptable salt thereof.

[15] The N-substituted phenylacetamide derivative of the above [1] wherein $R^1$ is a methoxy group, and $R^2$ is a hydrogen atom; or a physiologically acceptable salt thereof.

[16] The N-substituted phenylacetamide derivative of any one of the above [1]-[15] wherein D is defined as formula (A), or a physiologically acceptable salt thereof.

[17] The N-substituted phenylacetamide derivative of any one of the above [1]-[15] wherein D is defined as formula (B), or a physiologically acceptable salt thereof.

[18] The N-substituted phenylacetamide derivative of any one of the above [1]-[15] wherein D is defined as formula (C), or a physiologically acceptable salt thereof.

[19] The N-substituted phenylacetamide derivative of the above [1] wherein the compound of formula (I) is selected from the group consisting of N-(4-butyl-3-cyclohexenyl)-2-(4-hydroxy-3-methoxy-phenyl)acetamide, N-(cis-4-butylcyclohexyl)-2-(4-hydroxy-3-methoxy-phenyl)acetamide, N-(trans-4-butylcyclohexyl)-2-(4-hydroxy-3-methoxy-phenyl)acetamide, 2-(4-hydroxy-3-methoxyphenyl)-N-(cis-4-pentyl-cyclohexyl)acetamide, 2-(4-hydroxy-3-methoxyphenyl)-N-(trans-4-pentyl-cyclohexyl)acetamide, N-(4-butylidenecyclohexyl)-2-(4-hydroxy-3-methoxy-phenyl)acetamide, 2-(4-hydroxy-3-methoxyphenyl)-N-(4-pentylidene-cyclohexyl)acetamide, 2-(4-hydroxy-3-methoxyphenyl)-N-[4-(3-methyl-butylidene)cyclohexyl]acetamide, 2-(4-hydroxy-3-methoxyphenyl)-N-[4-(4-pentenylidene)-cyclohexyl]acetamide, N-{trans-4-[(Z)-1-butenyl]cyclohexyl}-2-(4-hydroxy-3-methoxyphenyl)acetamide, 2-(4-hydroxy-3-methoxyphenyl)-N-{trans-4-[(Z)-1-pentenyl]cyclohexyl}acetamide, 2-(4-hydroxy-3-methoxyphenyl)-N-{trans-4-[(Z)-1-propenyl]cyclohexyl}acetamide, 2-(4-hydroxy-3-methoxyphenyl)-N-{trans-4-[(Z)-4,4,4-trifluoro-1-butenyl]cyclohexyl}acetamide, 2-(4-hydroxy-3-methoxyphenyl)-N-[trans-4-(3-methyl-butyl)cyclohexyl]acetamide, 2-(4-hydroxy-3-methoxyphenyl)-N-[trans-4-(4-methyl-pentyl)cyclohexyl]acetamide, N-[trans-4-(2-cyclopropylethyl)cyclohexyl]-2-(4-hydroxy-3-methoxyphenyl)acetamide, 2-(4-hydroxy-3-methoxyphenyl)-N-[trans-4-(2-methyl-propyl)cyclohexyl]acetamide, N-[trans-4-(cyclopentylmethyl)cyclohexyl]-2-(4-hydroxy-3-methoxyphenyl)acetamide, 2-(4-hydroxy-3-methoxyphenyl)-N-[trans-4-(3-methyl-2-butenyl)cyclohexyl]acetamide, 2-(4-hydroxy-3-methoxyphenyl)-N-[cis-4-(3-methyl-2-butenyl)cyclohexyl]acetamide, 2-(4-hydroxy-3-methoxyphenyl)-N-[cis-4-(3-methyl-butyl)cyclohexyl]acetamide, N-{trans-4-[(E)-1-butenyl]cyclohexyl}-2-(4-hydroxy-3-methoxyphenyl)acetamide, 2-(4-hydroxy-3-methoxyphenyl)-N-{trans-4-[(E)-1-pentenyl]cyclohexyl}acetamide, 2-(4-hydroxy-3-methoxyphenyl)-N-{trans-4-[(E)-4-methyl-1-pentenyl]cyclohexyl}acetamide, N-[trans-4-(2-cyclobutylethyl)cyclohexyl]-2-(4-hydroxy-3-methoxyphenyl)acetamide, 2-(4-hydroxy-3-methoxyphenyl)-N-{cis-4-[(E)-1-pentenyl]cyclohexyl}acetamide, N-{cis-4-[(E)-1-butenyl]cyclohexyl}-2-(4-hydroxy-3-methoxyphenyl)acetamide, 2-(4-hydroxy-3-methoxyphenyl)-N-{cis-4-[(E)-3-methyl-1-butenyl]cyclohexyl}acetamide, N-{cis-4-[(E)-2-cyclopropylvinyl]cyclohexyl}-2-(4-hydroxy-3-methoxyphenyl)acetamide, 2-(4-hydroxy-3-methoxyphenyl)-N-(cis-4-propyl-cyclohexyl)acetamide, N-[cis-4-(3-cyclopropylpropyl)cyclohexyl]-2-(4-hydroxy-3-methoxyphenyl)acetamide, 2-(4-hydroxy-3-methoxyphenyl)-N-{trans-4-[(E)-3-methyl-1,3-butadienyl]cyclohexyl}acetamide, 2-(4-hydroxy-3-methoxyphenyl)-N-{trans-4-[(Z)-3-pentenyl]cyclohexyl}acetamide,
2-(4-hydroxy-3-methoxyphenyl)-N-{trans-4-[(E)-3-pentenyl]cyclohexyl}acetamide,
N-(4-cyclohexylidenecyclohexyl)-2-(4-hydroxy-3-methoxyphenyl)acetamide,
N-[4-(1-ethylpropylidene)cyclohexyl]-2-(4-hydroxy-3-methoxyphenyl)acetamide,
N-(4-cycloheptylidenecyclohexyl)-2-(4-hydroxy-3-methoxyphenyl)acetamide,
2-(4-hydroxy-3-methoxyphenyl)-N-(4-isopropylidene-cyclohexyl)acetamide,
N-(trans-4-cyclohexylcyclohexyl)-2-(4-hydroxy-3-methoxyphenyl)acetamide,
2-(4-hydroxy-3-methoxyphenyl)-N-[trans-4-(3-pentyl)-cyclohexyl]acetamide,
N-(trans-4-cyclobutylcyclohexyl)-2-(4-hydroxy-3-methoxyphenyl)acetamide,
N-(trans-4-cycloheptylcyclohexyl)-2-(4-hydroxy-3-methoxyphenyl)acetamide,
2-(4-hydroxy-3-methoxyphenyl)-N-[4-(3-pentyl)-3-cyclohexenyl]acetamide,
N-[4-(4-heptyl)-3-cyclohexenyl]-2-(4-hydroxy-3-methoxyphenyl)acetamide,
N-[trans-4-(2-ethyl-1-butenyl)cyclohexyl]-2-(4-hydroxy-3-methoxyphenyl)acetamide,
N-[trans-4-(cyclobutylidenemethyl)cyclohexyl]-2-(4-hydroxy-3-methoxyphenyl)acetamide,
N-[trans-4-(2-ethylbutyl)cyclohexyl]-2-(4-hydroxy-3-methoxyphenyl)acetamide,
N-[trans-4-(cyclobutylmethyl)cyclohexyl]-2-(4-hydroxy-3-methoxyphenyl)acetamide,
N-{trans-4-[(Z)-2-butenyl]cyclohexyl}-2-(4-hydroxy-3-methoxyphenyl)acetamide,
2-(4-hydroxy-3-methoxyphenyl)-N-[cis-4-(2-methyl-propyl)cyclohexyl]acetamide,
N-[trans-4-(3,3-dimethylbutyl)cyclohexyl]-2-(4-hydroxy-3-methoxyphenyl)acetamide,
2-(4-hydroxy-3-methoxyphenyl)-N-(spiro[5.5]undec-3-yl)acetamide, and
N-(4-butyl-4-ethylcyclohexyl)-2-(4-hydroxy-3-methoxyphenyl)acetamide;

or a physiologically acceptable salt thereof.

[20] The N-substituted phenylacetamide derivative of the above [1] wherein the compound of formula (I) is selected from the group consisting of
N-(4-butyl-3-cyclohexenyl)-2-(4-hydroxy-3-methoxy-phenyl)acetamide,
N-(cis-4-butylcyclohexyl)-2-(4-hydroxy-3-methoxy-phenyl)acetamide,
N-(trans-4-butylcyclohexyl)-2-(4-hydroxy-3-methoxy-phenyl)acetamide,
2-(4-hydroxy-3-methoxyphenyl)-N-(cis-4-pentyl-cyclohexyl)acetamide,
2-(4-hydroxy-3-methoxyphenyl)-N-(trans-4-pentyl-cyclohexyl)acetamide,
N-(4-butylidenecyclohexyl)-2-(4-hydroxy-3-methoxy-phenyl)acetamide,
N-{trans-4-[(Z)-1-butenyl]cyclohexyl}-2-(4-hydroxy-3-methoxyphenyl)acetamide,
2-(4-hydroxy-3-methoxyphenyl)-N-{trans-4-[(Z)-1-propenyl]cyclohexyl}acetamide,
2-(4-hydroxy-3-methoxyphenyl)-N-{trans-4-[(Z)-4,4,4-trifluoro-1-butenyl]cyclohexyl}acetamide,
2-(4-hydroxy-3-methoxyphenyl)-N-[trans-4-(3-methyl-butyl)cyclohexyl]acetamide,
2-(4-hydroxy-3-methoxyphenyl)-N-[trans-4-(4-methyl-pentyl)cyclohexyl]acetamide,
N-[trans-4-(2-cyclopropylethyl)cyclohexyl]-2-(4-hydroxy-3-methoxyphenyl)acetamide,
N-[trans-4-(cyclopentylmethyl)cyclohexyl]-2-(4-hydroxy-3-methoxyphenyl)acetamide,
2-(4-hydroxy-3-methoxyphenyl)-N-[trans-4-(3-methyl-2-butenyl)cyclohexyl]acetamide,
N-{trans-4-[(E)-1-butenyl]cyclohexyl}-2-(4-hydroxy-3-methoxyphenyl)acetamide,
2-(4-hydroxy-3-methoxyphenyl)-N-{trans-4-[(E)-1-pentenyl]cyclohexyl}acetamide,
2-(4-hydroxy-3-methoxyphenyl)-N-{trans-4-[(E)-4-methyl-1-pentenyl]cyclohexyl}acetamide,
2-(4-hydroxy-3-methoxyphenyl)-N-{cis-4-[(E)-1-pentenyl]cyclohexyl}acetamide,
N-{cis-4-[(E)-1-butenyl]cyclohexyl}-2-(4-hydroxy-3-methoxyphenyl)acetamide,
2-(4-hydroxy-3-methoxyphenyl)-N-{cis-4-[(E)-3-methyl-1-butenyl]cyclohexyl}acetamide,
2-(4-hydroxy-3-methoxyphenyl)-N-(cis-4-propyl-cyclohexyl)acetamide,
N-[4-(1-ethylpropylidene)cyclohexyl]-2-(4-hydroxy-3-methoxyphenyl)acetamide,
N-(trans-4-cyclohexylcyclohexyl)-2-(4-hydroxy-3-methoxyphenyl)acetamide,
2-(4-hydroxy-3-methoxyphenyl)-N-[trans-4-(3-pentyl)-cyclohexyl]acetamide,
N-(trans-4-cycloheptylcyclohexyl)-2-(4-hydroxy-3-methoxyphenyl)acetamide,
2-(4-hydroxy-3-methoxyphenyl)-N-[4-(3-pentyl)-3-cyclohexenyl]acetamide, and
N-[4-(4-heptyl)-3-cyclohexenyl]-2-(4-hydroxy-3-methoxyphenyl)acetamide;

or a physiologically acceptable salt thereof.

[21] The N-substituted phenylacetamide derivative of the above [1] wherein the compound of formula (I) is selected from the group consisting of
N-(4-butyl-3-cyclohexenyl)-2-(4-hydroxy-3-methoxy-phenyl)acetamide,
N-(cis-4-butylcyclohexyl)-2-(4-hydroxy-3-methoxy-phenyl)acetamide,
N-(trans-4-butylcyclohexyl)-2-(4-hydroxy-3-methoxy-phenyl)acetamide,
2-(4-hydroxy-3-methoxyphenyl)-N-(cis-4-pentyl-cyclohexyl)acetamide,
2-(4-hydroxy-3-methoxyphenyl)-N-(trans-4-pentyl-cyclohexyl)acetamide,
N-(4-butylidenecyclohexyl)-2-(4-hydroxy-3-methoxy-phenyl)acetamide,
N-{trans-4-[(Z)-1-butenyl]cyclohexyl}-2-(4-hydroxy-3-methoxyphenyl)acetamide,
2-(4-hydroxy-3-methoxyphenyl)-N-{trans-4-[(Z)-1-propenyl]cyclohexyl}acetamide,
2-(4-hydroxy-3-methoxyphenyl)-N-{trans-4-[(Z)-4,4,4-trifluoro-1-butenyl]cyclohexyl}acetamide,
N-{trans-4-[(E)-1-butenyl]cyclohexyl}-2-(4-hydroxy-3-methoxyphenyl)acetamide,
2-(4-hydroxy-3-methoxyphenyl)-N-{trans-4-[(E)-1-pentenyl]cyclohexyl}acetamide,
N-{cis-4-[(E)-1-butenyl]cyclohexyl}-2-(4-hydroxy-3-methoxyphenyl)acetamide,
2-(4-hydroxy-3-methoxyphenyl)-N-(cis-4-propyl-cyclohexyl)acetamide,
N-[4-(1-ethylpropylidene)cyclohexyl]-2-(4-hydroxy-3-methoxyphenyl)acetamide, and 2-(4-hydroxy-3-methoxyphenyl)-N-[4-(3-pentyl)-3-cyclohexenyl]acetamide;

or a physiologically acceptable salt thereof.

[22] A pharmaceutical composition comprising as an active ingredient the N-substituted phenylacetamide derivative of any one of the above [1]-[21] or a physiologically acceptable salt thereof.

[23] An analgesic agent or anti-inflammatory agent comprising as an active ingredient the N-substituted phenylacetamide derivative of any one of the above [1]-[21] or a physiologically acceptable salt thereof.

[24] A method for treating or preventing pain and/or inflammation, which comprises administering an effective amount of the N-substituted phenylacetamide derivative of any one of the above [1]-[21] or a physiologically acceptable salt thereof to a patient in need thereof.

[25] Use of the N-substituted phenylacetamide derivative of any one of the above [1]-[21] or a physiologically acceptable salt thereof, for the manufacture of a medicament for treating or preventing pain and/or inflammation.

[26] The N-substituted phenylacetamide derivative of the above [1] wherein
$R^1$ is a methoxy group or a hydroxyl group;
$R^2$ is a hydrogen atom; and
D is a group of the following formula (A), (B), or (C):

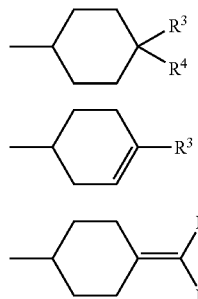

(A)

(B)

(C)

wherein
$R^3$ is defined as a group of —X—Y—Z, wherein
X is a single bond;
Y is a single bond;
Z is a straight or branched hydrocarbon group selected from the group consisting of a $C_{1-7}$ alkyl group and a $C_{2-7}$ alkenyl group having one double bond, in which the hydrocarbon may be optionally substituted with a $C_{3-8}$ cycloalkyl; or a cyclic group selected from the group consisting a $C_{3-8}$ cycloalkyl group and a $C_{3-8}$ cycloalkylidene-$C_{1-3}$ alkyl group;
the alkyl group or the alkenyl group in the above Z may be optionally substituted with 1-5 fluorine atoms;
$R^4$ is a hydrogen atom or a $C_{1-4}$ alkyl group; alternatively $R^3$ and $R^4$ are taken together to form a $C_{3-8}$ cycloalkyl group;
further provided that $R^3$ and $R^4$ in formula (A) contain 3-10 carbon atoms in total; $R^3$ in formula (B) contains 3-10 carbon atoms; and $R^3$ and $R^4$ in formula (C) contain 2-9 carbon atoms in total, or a physiologically acceptable salt thereof.

[27] The N-substituted phenylacetamide derivative of the above [1] wherein
$R^1$ is a methoxy group or a hydroxyl group;
$R^2$ is a hydrogen atom; and
D is a group of the following formula (A), (B), or (C):

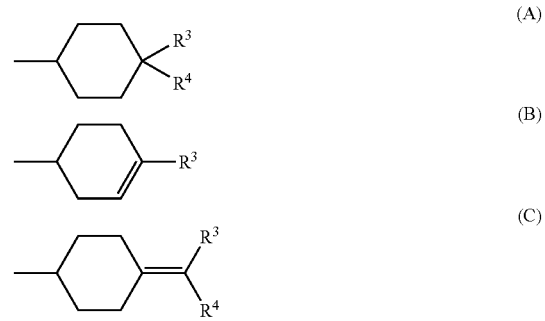

(A)

(B)

(C)

wherein
$R^3$ is defined as a group of —X—Y—Z, wherein
X is a single bond;
Y is a single bond;
Z is a straight or branched hydrocarbon group selected from the group consisting of a $C_{1-7}$ alkyl group and a $C_{2-7}$ alkenyl group, in which the hydrocarbon may be optionally substituted with a $C_{3-8}$ cycloalkyl; or a cyclic group selected from the group consisting of a $C_{3-8}$ cycloalkyl group and a $C_{3-8}$ cycloalkylidene-$C_{1-3}$ alkyl group;
the alkyl group or the alkenyl group in the above Z may be optionally substituted with 1-5 fluorine atoms;
$R^4$ is a hydrogen atom or a $C_{1-4}$ alkyl group;
further provided that $R^3$ and $R^4$ in formula (A) contain 3-10 carbon atoms in total; $R^3$ in formula (B) contains 3-10 carbon atoms; and $R^3$ and $R^4$ in formula (C) contain 2-9 carbon atoms in total, or a physiologically acceptable salt thereof.

[28] The N-substituted phenylacetamide derivative of the above [1] wherein
$R^1$ is a methoxy group or a hydroxyl group;
$R^2$ is a hydrogen atom; and
D is a group of the following formula (A), (B), or (C):

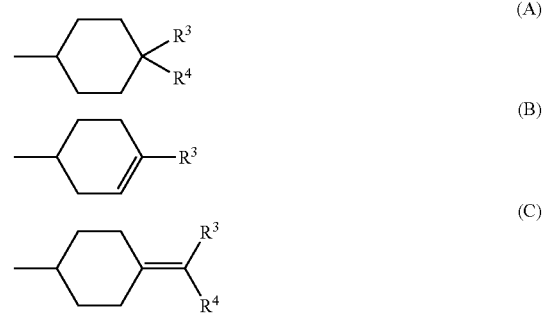

(A)

(B)

(C)

wherein
$R^3$ is defined as a group of —X—Y—Z, wherein
X is a single bond;
Y is a single bond;
Z is a straight or branched hydrocarbon group selected from the group consisting of a $C_{1-7}$ alkyl group and a $C_{2-7}$ alkenyl group having one double bond, in which may be optionally substituted with a $C_{3-8}$ cycloalkyl; or a cyclic group selected from the group consisting of a $C_{3-8}$ cycloalkyl group and a $C_{3-8}$ cycloalkylidene-$C_{1-3}$ alkyl group;

the alkyl group or the alkenyl group in the above Z may be optionally substituted with 1-5 fluorine atoms;

$R^4$ is a hydrogen atom or a $C_{1-4}$ alkyl group;

further provided that $R^3$ and $R^4$ in formula (A) contain 3-10 carbon atoms in total; $R^3$ in formula (B) contains 3-10 carbon atoms; and $R^3$ and $R^4$ in formula (C) contain 2-9 carbon atoms in total, or a physiologically acceptable salt thereof.

[29] The N-substituted phenylacetamide derivative of the above [1] wherein $R^1$ is a methoxy group or a hydroxyl group;

$R^2$ is a hydrogen atom; and

D is a group of the following formula (A), (B), or (C):

(A)

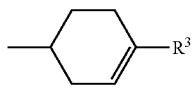
(B)

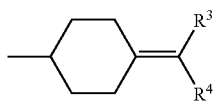
(C)

wherein $R^3$ is defined as a group of —X—Y—Z, wherein

X is a single bond;

Y is a single bond;

Z is a straight or branched hydrocarbon group selected from the group consisting of a $C_{1-7}$ alkyl group and a $C_{2-7}$ alkenyl group having one double bond, in which the hydrocarbon may be optionally substituted with a $C_{3-8}$ cycloalkyl; or a cyclic group selected from the group consisting of a $C_{3-8}$ cycloalkyl group and a $C_{3-8}$ cycloalkylidene-$C_{1-3}$ alkyl group;

the alkyl group or the alkenyl group in the above Z may be optionally substituted with 1-5 fluorine atoms;

$R^4$ is a hydrogen atom or a $C_{1-4}$ alkyl group; alternatively $R^3$ and $R^4$ are taken together to form a $C_{3-8}$ cycloalkyl group;

further provided that $R^3$ and $R^4$ in formula (A) contain 4-10 carbon atoms in total; $R^3$ in formula (B) contains 4-10 carbon atoms; and $R^3$ and $R^4$ in formula (C) contain 3-9 carbon atoms in total, or a physiologically acceptable salt thereof.

[30] The N-substituted phenylacetamide derivative of the above [1] wherein $R^1$ is a methoxy group or a hydroxyl group;

$R^2$ is a hydrogen atom; and

D is a group of the following formula (A), (B), or (C):

(A)

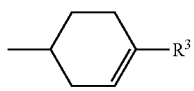
(B)

-continued

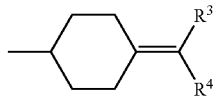
(C)

wherein $R^3$ is defined as a group of —X—Y—Z, wherein

X is a single bond;

Y is a single bond;

Z is a straight or branched hydrocarbon group selected from the group consisting of a $C_{1-7}$ alkyl group and a $C_{2-7}$ alkenyl group, in which the hydrocarbon may be optionally substituted with a $C_{3-8}$ cycloalkyl; or a cyclic group selected from the group consisting of a $C_{3-8}$ cycloalkyl group and a $C_{3-8}$ cycloalkylidene-$C_{1-3}$ alkyl group;

the alkyl group or the alkenyl group in the above Z may be optionally substituted with 1-5 fluorine atoms;

$R^4$ is a hydrogen atom or a $C_{1-4}$ alkyl group;

further provided that $R^3$ and $R^4$ in formula (A) contain 4-10 carbon atoms in total; $R^3$ in formula (B) contains 4-10 carbon atoms; and $R^3$ and $R^4$ in formula (C) contain 3-9 carbon atoms in total, or a physiologically acceptable salt thereof.

[31] The N-substituted phenylacetamide derivative of the above [1] wherein $R^1$ is a methoxy group or a hydroxyl group;

$R^2$ is a hydrogen atom; and

D is a group of the following formula (A), (B), or (C):

(A)

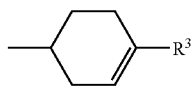
(B)

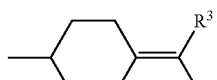
(C)

wherein $R^3$ is defined as a group of —X—Y—Z, wherein

X is a single bond;

Y is a single bond;

Z is a straight or branched hydrocarbon group selected from the group consisting of a $C_{1-7}$ alkyl group and a $C_{2-7}$ alkenyl group having one double bond, in which the hydrocarbon may be optionally substituted with a $C_{3-8}$ cycloalkyl; or a cyclic group selected from the group consisting of a $C_{3-8}$ cycloalkyl group and a $C_{3-8}$ cycloalkylidene-$C_{1-3}$ alkyl group;

the alkyl group or the alkenyl group in the above Z may be optionally substituted with 1-5 fluorine atoms;

$R^4$ is a hydrogen atom or a $C_{1-4}$ alkyl group;

further provided that $R^3$ and $R^4$ in formula (A) contain 4-10 carbon atoms in total; $R^3$ in formula (B) contains 4-10 carbon atoms; and $R^3$ and $R^4$ in formula (C) contain 3-9 carbon atoms in total, or a physiologically acceptable salt thereof.

[32] The N-substituted phenylacetamide derivative of the above [1] wherein
R$^1$ is a methoxy group or a hydroxyl group;
R$^2$ is a hydrogen atom; and
D is a group of the following formula (A), (B), or (C):

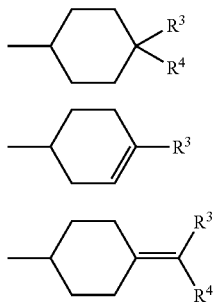

wherein
R$^3$ is defined as a group of —X—Y—Z, wherein
X is a single bond;
Y is a single bond;
Z is a straight or branched hydrocarbon group selected from the group consisting of a C$_{1-7}$ alkyl group and a C$_{2-7}$ alkenyl group having one double bond, in which the hydrocarbon may be optionally substituted with a C$_{3-8}$ cycloalkyl; or a cyclic group selected from the group consisting of a C$_{3-8}$ cycloalkyl group and a C$_{3-8}$ cycloalkylidene-C$_{1-3}$ alkyl group;
the alkyl group or the alkenyl group in the above Z may be optionally substituted with 1-5 fluorine atoms;
R$^4$ is a hydrogen atom; alternatively
R$^3$ and R$^4$ are taken together to form a C$_{3-8}$ cycloalkyl group;
further provided that R$^3$ and R$^4$ in formula (A) contain 3-10 carbon atoms in total; R$^3$ in formula (B) contains 3-10 carbon atoms; and R$^3$ and R$^4$ in formula (C) contain 2-9 carbon atoms in total,
or a physiologically acceptable salt thereof.

[33] The N-substituted phenylacetamide derivative of the above [1] wherein
R$^1$ is a methoxy group or a hydroxyl group;
R$^2$ is a hydrogen atom; and
D is a group of the following formula (A), (B), or (C):

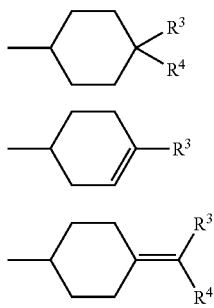

wherein
R$^3$ is defined as a group of —X—Y—Z, wherein
X is a single bond;
Y is a single bond;
Z is a straight or branched hydrocarbon group selected from the group consisting of a C$_{1-7}$ alkyl group and a C$_{2-7}$ alkenyl group, in which the hydrocarbon may be optionally substituted with a C$_{3-8}$ cycloalkyl; or a cyclic group selected from the group consisting of a C$_{3-8}$ cycloalkyl group and a C$_{3-8}$ cycloalkylidene-C$_{1-3}$ alkyl group;
the alkyl group or the alkenyl group in the above Z may be optionally substituted with 1-5 fluorine atoms;
R$^4$ is a hydrogen atom;
further provided that R$^3$ in formula (A) contains 3-10 carbon atoms; R$^3$ in formula (B) contains 3-10 carbon atoms; and R$^3$ in formula (C) contains 2-9 carbon atoms; or a physiologically acceptable salt thereof.

[34] The N-substituted phenylacetamide derivative of the above [1] wherein
R$^1$ is a methoxy group or a hydroxyl group;
R$^2$ is a hydrogen atom; and
D is a group of the following formula (A), (B), or (C):

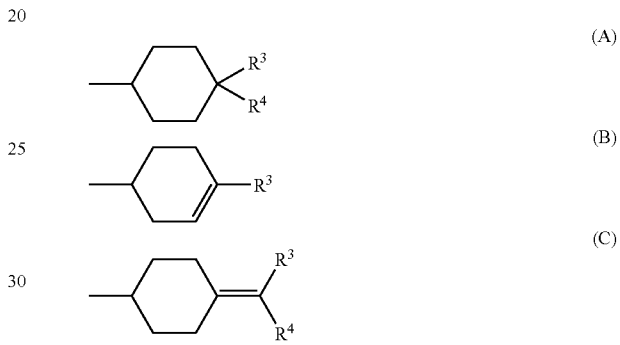

wherein
R$^3$ is defined as a group of —X—Y—Z, wherein
X is a single bond;
Y is a single bond;
Z is a straight or branched hydrocarbon group selected from the group consisting of a C$_{1-7}$ alkyl group and a C$_{2-7}$ alkenyl group having one double bond, in which the hydrocarbon may be optionally substituted with a C$_{3-8}$ cycloalkyl; or a cyclic group selected from the group consisting of a C$_{3-8}$ cycloalkyl group and a C$_{3-8}$ cycloalkylidene-C$_{1-3}$ alkyl group;
the alkyl group or the alkenyl group in the above Z may be optionally substituted with 1-5 fluorine atoms;
R$^4$ is a hydrogen atom;
further provided that R$^3$ in formula (A) contains 3-10 carbon atoms; R$^3$ in formula (B) contains 3-10 carbon atoms; and R$^3$ in formula (C) contains 2-9 carbon atoms, or a physiologically acceptable salt thereof.

[35] The N-substituted phenylacetamide derivative of the above [1] wherein
R$^1$ is a methoxy group or a hydroxyl group;
R$^2$ is a hydrogen atom; and
D is a group of the following formula (A), (B), or (C):

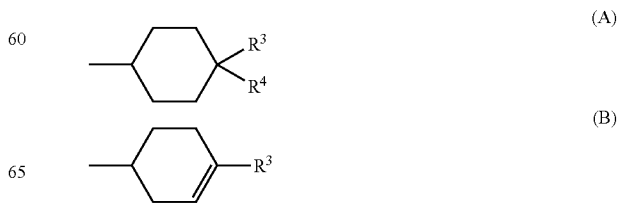

-continued

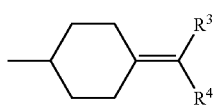
(C)

wherein
$R^3$ is defined as a group of —X—Y—Z, wherein
X is a single bond;
Y is a single bond;
Z is a straight or branched hydrocarbon group selected from the group consisting of a $C_{1-7}$ alkyl group and a $C_{2-7}$ alkenyl group having one double bond, in which the hydrocarbon may be optionally substituted with a $C_{3-8}$ cycloalkyl; or a cyclic group selected from the group consisting of a $C_{3-8}$ cycloalkyl group and a $C_{3-8}$ cycloalkylidene-$C_{1-3}$ alkyl group;
the alkyl group or the alkenyl group in the above Z may be optionally substituted with 1-5 fluorine atoms;
$R^4$ is a hydrogen atom; alternatively
$R^3$ and $R^4$ are taken together to form a $C_{3-8}$ cycloalkyl group;
further provided that $R^3$ and $R^4$ in formula (A) contain 4-10 carbon atoms in total; $R^3$ in formula (B) contains 4-10 carbon atoms; and $R^3$ and $R^4$ in formula (C) contain 3-9 carbon atoms in total,
or a physiologically acceptable salt thereof.

[36] The N-substituted phenylacetamide derivative of the above [1] wherein
$R^1$ is a methoxy group or a hydroxyl group;
$R^2$ is a hydrogen atom; and
D is a group of the following formula (A), (B), or (C):

(A)

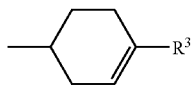
(B)

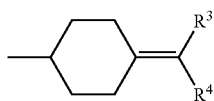
(C)

wherein
$R^3$ is defined as a group of —X—Y—Z, wherein
X is a single bond;
Y is a single bond;
Z is a straight or branched hydrocarbon group selected from the group consisting of a $C_{1-7}$ alkyl group and a $C_{2-7}$ alkenyl group, in which the hydrocarbon may be optionally substituted with a $C_{3-8}$ cycloalkyl; or a cyclic group selected from the group consisting of a $C_{3-8}$ cycloalkyl group and a $C_{3-8}$ cycloalkylidene-$C_{1-3}$ alkyl group;
the alkyl group or the alkenyl group in the above Z may be optionally substituted with 1-5 fluorine atoms;
$R^4$ is a hydrogen atom;
further provided that $R^3$ in formula (A) contains 4-10 carbon atoms; $R^3$ in formula (B) contains 4-10 carbon atoms; and $R^3$ in formula (C) contains 3-9 carbon atoms, or a physiologically acceptable salt thereof.

[37] The N-substituted phenylacetamide derivative of the above [1] wherein
$R^1$ is a methoxy group or a hydroxyl group;
$R^2$ is a hydrogen atom; and
D is a group of the following formula (A), (B), or (C):

(A)

(B)

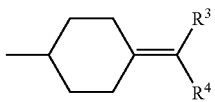
(C)

wherein
$R^3$ is defined as a group of —X—Y—Z, wherein
X is a single bond;
Y is a single bond;
Z is a straight or branched hydrocarbon group selected from the group consisting of a $C_{1-7}$ alkyl group and a $C_{2-7}$ alkenyl group having one double bond, in which the hydrocarbon may be optionally substituted with a $C_{3-8}$ cycloalkyl; or a cyclic group selected from the group consisting of a $C_{3-8}$ cycloalkyl group and a $C_{3-8}$ cycloalkylidene-$C_{1-3}$ alkyl group;
the alkyl group or the alkenyl group in the above Z may be optionally substituted with 1-5 fluorine atoms;
$R^4$ is a hydrogen atom;
further provided that $R^3$ in formula (A) contains 4-10 carbon atoms; $R^3$ in formula (B) contains 4-10 carbon atoms; and $R^3$ in formula (C) contains 3-9 carbon atoms, or a physiologically acceptable salt thereof.

[38] The N-substituted phenylacetamide derivative of the above [1] wherein
$R^1$ is a methoxy group or a hydroxyl group;
$R^2$ is a hydrogen atom; and
D is a group of the following formula (A), (B), or (C):

(A)

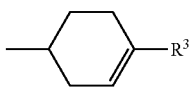
(B)

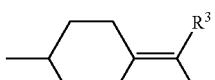
(C)

wherein
$R^3$ is defined as a group of —X—Y—Z, wherein
X is a single bond;
Y is a single bond;
Z is a straight or branched hydrocarbon group selected from the group consisting of a $C_{1-7}$ alkyl group and a $C_{2-7}$ alkenyl group, in which the hydrocarbon may be optionally substituted with a $C_{3-8}$ cycloalkyl; or a $C_{3-8}$ cycloalkylidene-$C_{1-3}$ alkyl group;

the alkyl group or the alkenyl group in the above Z may be optionally substituted with 1-5 fluorine atoms;

$R^4$ is a hydrogen atom;

further provided that $R^3$ in formula (A) contains 4-10 carbon atoms; $R^3$ in formula (B) contains 4-10 carbon atoms; and $R^3$ in formula (C) contains 3-9 carbon atoms, or a physiologically acceptable salt thereof.

[39] The N-substituted phenylacetamide derivative of the above [1] wherein $R^1$ is a methoxy group or a hydroxyl group;

$R^2$ is a hydrogen atom; and

D is a group of the following formula (A), (B), or (C):

 (A)

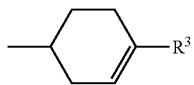 (B)

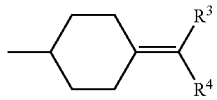 (C)

wherein $R^3$ is defined as a group of —X—Y—Z, wherein

X is a single bond;

Y is a single bond;

Z is a straight or branched hydrocarbon group selected from the group consisting of a $C_{1-7}$ alkyl group and a $C_{2-7}$ alkenyl group having one double bond, in which the hydrocarbon may be optionally substituted with a $C_{3-8}$ cycloalkyl; or a $C_{3-8}$ cycloalkylidene-$C_{1-3}$ alkyl group;

the alkyl group or the alkenyl group in the above Z may be optionally substituted with 1-5 fluorine atoms;

$R^4$ is a hydrogen atom;

further provided that $R^3$ in formula (A) contains 4-10 carbon atoms; $R^3$ in formula (B) contains 4-10 carbon atoms; and $R^3$ in formula (C) contains 3-9 carbon atoms, or a physiologically acceptable salt thereof.

[40] The N-substituted phenylacetamide derivative of the above [1] wherein $R^1$ is a methoxy group or a hydroxyl group;

$R^2$ is a hydrogen atom; and

D is a group of the following formula (A), (B), or (C):

 (A)

 (B)

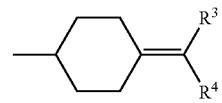 (C)

wherein $R^3$ is defined as a group of —X—Y—Z, wherein

X is a single bond;

Y is a single bond;

Z is a straight or branched hydrocarbon group selected from the group consisting of a $C_{1-7}$ alkyl group and a $C_{2-7}$ alkenyl group, in which the hydrocarbon may be optionally substituted with 1-5 fluorine atoms; or a $C_{3-8}$ cycloalkylidene-$C_{1-3}$ alkyl group;

$R^4$ is a hydrogen atom;

further provided that $R^3$ in formula (A) contains 4-10 carbon atoms; $R^3$ in formula (B) contains 4-10 carbon atoms; and $R^3$ in formula (C) contains 3-9 carbon atoms, or a physiologically acceptable salt thereof.

[41] The N-substituted phenylacetamide derivative of the above [1] wherein $R^1$ is a methoxy group or a hydroxyl group;

$R^2$ is a hydrogen atom; and

D is a group of the following formula (A), (B), or (C):

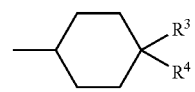 (A)

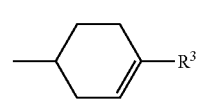 (B)

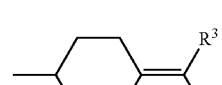 (C)

wherein $R^3$ is defined as a group of —X—Y—Z, wherein

X is a single bond;

Y is a single bond;

Z is a straight or branched hydrocarbon group selected from the group consisting of a $C_{1-7}$ alkyl group and a $C_{2-7}$ alkenyl group having one double bond, in which the hydrocarbon may be optionally substituted with 1-5 fluorine atoms; or a $C_{3-8}$ cycloalkylidene-$C_{1-3}$ alkyl group;

$R^4$ is a hydrogen atom;

further provided that $R^3$ in formula (A) contains 4-10 carbon atoms; $R^3$ in formula (B) contains 4-10 carbon atoms; and $R^3$ in formula (C) contains 3-9 carbon atoms, or a physiologically acceptable salt thereof.

[42] The N-substituted phenylacetamide derivative of the above [1] wherein $R^1$ is a methoxy group or a hydroxyl group;

$R^2$ is a hydrogen atom; and

D is a group of the following formula (A), (B), or (C):

(A)

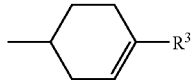
(B)

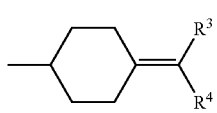
(C)

wherein $R^3$ is defined as a group of —X—Y—Z, wherein

X is a single bond;

Y is a single bond;

Z is a straight or branched hydrocarbon group selected from the group consisting of a $C_{1-7}$ alkyl group and a $C_{2-7}$ alkenyl group, in which the hydrocarbon may be optionally substituted with 1-5 fluorine atoms;

$R^4$ is a hydrogen atom;

further provided that $R^3$ in formula (A) contains 4-10 carbon atoms; $R^3$ in formula (B) contains 4-10 carbon atoms; and $R^3$ in formula (C) contains 3-9 carbon atoms, or a physiologically acceptable salt thereof.

[43] The N-substituted phenylacetamide derivative of the above [1] wherein $R^1$ is a methoxy group or a hydroxyl group;

$R^2$ is a hydrogen atom; and

D is a group of the following formula (A), (B), or (C)

(A)

(B)

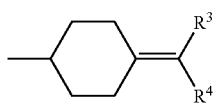
(C)

wherein $R^3$ is defined as a group of —X—Y—Z, wherein

X is a single bond;

Y is a single bond;

Z is a straight or branched hydrocarbon group selected from the group consisting of a $C_{1-7}$ alkyl group and a $C_{2-7}$ alkenyl group having one double bond, in which the hydrocarbon may be optionally substituted with 1-5 fluorine atoms;

$R^4$ is a hydrogen atom;

further provided that $R^3$ in formula (A) contains 4-10 carbon atoms; $R^3$ in formula (B) contains 4-10 carbon atoms; and $R^3$ in formula (C) contains 3-9 carbon atoms, or a physiologically acceptable salt thereof.

[44] The N-substituted phenylacetamide derivative of the above [1] wherein $R^1$ is a methoxy group or a hydroxyl group;

$R^2$ is a hydrogen atom; and

D is a group of the following formula (A), (B), or (C):

(A)

(B)

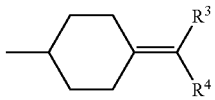
(C)

wherein $R^3$ is defined as a group of —X—Y—Z, wherein

X is a single bond;

Y is a single bond;

Z is a straight hydrocarbon group selected from the group consisting of a $C_{1-7}$ alkyl group and a $C_{2-7}$ alkenyl group having one double bond, in which the hydrocarbon may be optionally substituted with 1-5 fluorine atoms;

$R^4$ is a hydrogen atom;

further provided that $R^3$ in formula (A) contains 4-10 carbon atoms; $R^3$ in formula (B) contains 4-10 carbon atoms; and $R^3$ in formula (C) contains 3-9 carbon atoms, or a physiologically acceptable salt thereof.

[45] The N-substituted phenylacetamide derivative of the above [1] wherein $R^1$ is a methoxy group or a hydroxyl group;

$R^2$ is a hydrogen atom; and

D is a group of the following formula (A), (B), or (C):

(A)

(B)

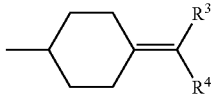
(C)

wherein $R^3$ is defined as a group of —X—Y—Z, wherein

X is a single bond;

Y is a single bond;

Z is a branched hydrocarbon group selected from the group consisting of a $C_{1-7}$ alkyl group and a $C_{2-7}$ alkenyl group having one double bond, in which the hydrocarbon may be optionally substituted with 1-5 fluorine atoms;
R⁴ is a hydrogen atom;
further provided that R³ in formula (A) contains 4-10 carbon atoms; R³ in formula (B) contains 4-10 carbon atoms; and R³ in formula (C) contains 3-9 carbon atoms, or a physiologically acceptable salt thereof.

[46] The N-substituted phenylacetamide derivative of the above [1] wherein
R¹ is a methoxy group;
R² is a hydrogen atom; and
D is a group of the following formula (A):

(A)

wherein
R³ is defined as a group of —X—Y—Z, wherein
X is a single bond;
Y is a single bond;
Z is a straight or branched hydrocarbon group selected from the group consisting of a $C_{3-7}$ alkyl group and a $C_{3-7}$ alkenyl group, in which the hydrocarbon may be optionally substituted with 1-5 fluorine atoms;
R⁴ is a hydrogen atom, or a physiologically acceptable salt thereof.

[47] The N-substituted phenylacetamide derivative of the above [1] wherein
R¹ is a methoxy group;
R² is a hydrogen atom; and
D is a group of the following formula (A):

(A)

wherein
R³ is defined as a group of —X—Y—Z, wherein
X is a single bond;
Y is a single bond;
Z is a straight hydrocarbon group selected from the group consisting of a $C_{3-7}$ alkyl group and a $C_{3-7}$ alkenyl group, in which the hydrocarbon may be optionally substituted with 1-5 fluorine atoms;
R⁴ is a hydrogen atom, or a physiologically acceptable salt thereof.

[48] The N-substituted phenylacetamide derivative of the above [1] wherein
R¹ is a methoxy group;
R² is a hydrogen atom; and
D is a group of the following formula (A):

(A)

wherein
R³ is defined as a group of —X—Y—Z, wherein
X is a single bond;
Y is a single bond;
Z is a branched hydrocarbon group selected from the group consisting of a $C_{3-7}$ alkyl group and a $C_{3-7}$ alkenyl group, in which the hydrocarbon may be optionally substituted with 1-5 fluorine atoms;
R⁴ is a hydrogen atom, or a physiologically acceptable salt thereof.

[49] The N-substituted phenylacetamide derivative of the above [1] wherein
R¹ is a methoxy group;
R² is a hydrogen atom; and
D is a group of the following formula (A):

(A)

wherein
R³ is defined as a group of —X—Y—Z, wherein
X is a single bond;
Y is a single bond;
Z is a straight or branched hydrocarbon group selected from the group consisting of a $C_{3-7}$ alkyl group and a $C_{3-7}$ alkenyl group having one double bond, in which the hydrocarbon may be optionally substituted with 1-5 fluorine atoms;
R⁴ is a hydrogen atom, or a physiologically acceptable salt thereof.

[50] The N-substituted phenylacetamide derivative of the above [1] wherein
R¹ is a methoxy group;
R² is a hydrogen atom; and
D is a group of the following formula (A):

(A)

wherein
R³ is defined as a group of —X—Y—Z, wherein
X is a single bond;
Y is a single bond;
Z is a straight hydrocarbon group selected from the group consisting of a $C_{3-7}$ alkyl group and a $C_{3-7}$ alkenyl group having one double bond, in which the hydrocarbon may be optionally substituted with 1-5 fluorine atoms;
R⁴ is a hydrogen atom, or a physiologically acceptable salt thereof.

[51] The N-substituted phenylacetamide derivative of the above [1] wherein
R¹ is a methoxy group;
R² is a hydrogen atom; and D is a group of the following formula (A):

wherein
$R^3$ is defined as a group of —X—Y—Z, wherein
X is a single bond;
Y is a single bond;
Z is a branched hydrocarbon group selected from the group consisting of a $C_{3-7}$ alkyl group and a $C_{3-7}$ alkenyl group having one double bond, in which the hydrocarbon may be optionally substituted with 1-5 fluorine atoms;
$R^4$ is a hydrogen atom, or a physiologically acceptable salt thereof.

[52] The N-substituted phenylacetamide derivative of the above [1] wherein
$R^1$ is a methoxy group;
$R^2$ is a hydrogen atom; and
D is a group of the following formula (A):

wherein
$R^3$ is defined as a group of —X—Y—Z, wherein
X is a single bond;
Y is a single bond;
Z is a straight or branched hydrocarbon group selected from the group consisting of a $C_{4-7}$ alkyl group and a $C_{4-7}$ alkenyl group having one double bond, in which the hydrocarbon may be optionally substituted with 1-5 fluorine atoms;
$R^4$ is a hydrogen atom, or a physiologically acceptable salt thereof.

[53] The N-substituted phenylacetamide derivative of the above [1] wherein
$R^1$ is a methoxy group;
$R^2$ is a hydrogen atom; and
D is a group of the following formula (A):

wherein
$R^3$ is defined as a group of —X—Y—Z, wherein
X is a single bond;
Y is a single bond;
Z is a straight hydrocarbon group selected from the group consisting of a $C_{4-7}$ alkyl group and a $C_{4-7}$ alkenyl group having one double bond, in which the hydrocarbon may be optionally substituted with 1-5 fluorine atoms;
$R^4$ is a hydrogen atom, or a physiologically acceptable salt thereof.

[54] The N-substituted phenylacetamide derivative of the above [1] wherein
$R^1$ is a methoxy group;
$R^2$ is a hydrogen atom; and
D is a group of the following formula (A):

wherein
$R^3$ is defined as a group of —X—Y—Z, wherein
X is a single bond;
Y is a single bond;
Z is a branched hydrocarbon group selected from the group consisting of a $C_{4-7}$ alkyl group and a $C_{4-7}$ alkenyl group having one double bond, in which the hydrocarbon may be optionally substituted with 1-5 fluorine atoms;
$R^4$ is a hydrogen atom, or a physiologically acceptable salt thereof.

[55] The N-substituted phenylacetamide derivative of the above [1] wherein
$R^1$ is a methoxy group;
$R^2$ is a hydrogen atom; and
D is a group of the following formula (C):

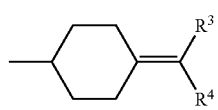

wherein
$R^3$ is defined as a group of —X—Y—Z, wherein
X is a single bond;
Y is a single bond;
Z is a straight or branched hydrocarbon group selected from the group consisting of a $C_{1-7}$ alkyl group and a $C_{2-7}$ alkenyl group, in which the hydrocarbon may be optionally substituted with 1-5 fluorine atoms;
$R^4$ is a hydrogen atom or a $C_{1-4}$ alkyl group; alternatively $R^3$ and $R^4$ are taken together to form a $C_{3-8}$ cycloalkyl group;
further provided that $R^3$ and $R^4$ in formula (C) contain 2-8 carbon atoms in total, or a physiologically acceptable salt thereof.

[56] The N-substituted phenylacetamide derivative of the above [1] wherein
$R^1$ is a methoxy group;
$R^2$ is a hydrogen atom; and
D is a group of the following formula (C):

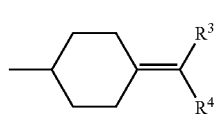

wherein
R³ is defined as a group of —X—Y—Z, wherein
X is a single bond;
Y is a single bond;
Z is a straight or branched hydrocarbon group selected from the group consisting of a C₁₋₇ alkyl group and a C₂₋₇ alkenyl group, in which the hydrocarbon may be optionally substituted with 1-5 fluorine atoms;
R⁴ is a hydrogen atom or a C₁₋₄ alkyl group;
further provided that R³ and R⁴ in formula (C) contain 2-8 carbon atoms in total, or a physiologically acceptable salt thereof.

[57] The N-substituted phenylacetamide derivative of the above [1] wherein
R¹ is a methoxy group;
R² is a hydrogen atom; and
D is a group of the following formula (C):

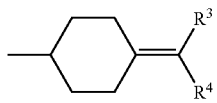

wherein
R³ is defined as a group of —X—Y—Z, wherein
X is a single bond;
Y is a single bond;
Z is a straight or branched hydrocarbon group selected from the group consisting of a C₁₋₇ alkyl group and a C₂₋₇ alkenyl group, in which the hydrocarbon may be optionally substituted with 1-5 fluorine atoms;
R⁴ is a hydrogen atom or a C₁₋₄ alkyl group;
further provided that R³ and R⁴ in formula (C) contain 3-8 carbon atoms in total, or a physiologically acceptable salt thereof.

[58] The N-substituted phenylacetamide derivative of the above [1] wherein
R¹ is a methoxy group;
R² is a hydrogen atom; and
D is a group of the following formula (C):

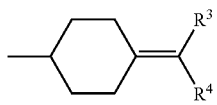

wherein
R³ is defined as a group of —X—Y—Z, wherein
X is a single bond;
Y is a single bond;
Z is a straight or branched hydrocarbon group selected from the group consisting of a C₁₋₇ alkyl group and a C₂₋₇ alkenyl group;
R⁴ is a hydrogen atom or a C₁₋₄ alkyl group; alternatively R³ and R⁴ are taken together to form a C₃₋₈ cycloalkyl group;
further provided that R³ and R⁴ in formula (C) contain 2-8 carbon atoms in total, or a physiologically acceptable salt thereof.

[59] The N-substituted phenylacetamide derivative of the above [1] wherein
R¹ is a methoxy group;
R² is a hydrogen atom; and
D is a group of the following formula (C):

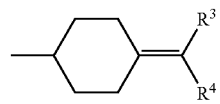

wherein
R³ is defined as a group of —X—Y—Z, wherein
X is a single bond;
Y is a single bond;
Z is a straight or branched hydrocarbon group selected from the group consisting of a C₁₋₇ alkyl group and a C₂₋₇ alkenyl group;
R⁴ is a hydrogen atom or a C₁₋₄ alkyl group;
further provided that R³ and R⁴ in formula (C) contain 2-8 carbon atoms in total, or a physiologically acceptable salt thereof.

[60] The N-substituted phenylacetamide derivative of the above [1] wherein
R¹ is a methoxy group;
R² is a hydrogen atom; and
D is a group of the following formula (C):

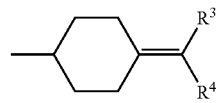

wherein
R³ is defined as a group of —X—Y—Z, wherein
X is a single bond;
Y is a single bond;
Z is a straight or branched hydrocarbon group selected from the group consisting of a C₁₋₇ alkyl group and a C₂₋₇ alkenyl group;
R⁴ is a hydrogen atom or a C₁₋₄ alkyl group;
further provided that R³ and R⁴ in formula (C) contain 3-8 carbon atoms in total, or a physiologically acceptable salt thereof.

[61] The N-substituted phenylacetamide derivative of the above [1] wherein
R¹ is a methoxy group;
R² is a hydrogen atom; and
D is a group of the following formula (C):

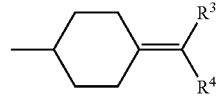

wherein
R³ is defined as a group of —X—Y—Z, wherein
X is a single bond;
Y is a single bond;

Z is a straight or branched hydrocarbon group of a $C_{1-7}$ alkyl group;

$R^4$ is a hydrogen atom or a $C_{1-4}$ alkyl group;

further provided that $R^3$ and $R^4$ in formula (C) contain 3-8 carbon atoms in total, or a physiologically acceptable salt thereof.

EFFECT OF THE INVENTION

The present invention provides compounds that exhibit a potent analgesic action but a low irritancy, and hence will provide an analgesic agent and an anti-inflammatory agent, as well as a medicament for treating neuropathic pain such as diabetic neuropathic pain, postherpetic neuralgia, trigeminal neuralgia, and HIV-multiple neuropathic pain; and pain caused by rheumatoid arthritis or osteoarthritis, which are not sufficiently treated with existing analgesic agents; and furthermore a medicament for treating and/or preventing migraine or cluster headache, pruritus, allergic and nonallergic rhinitis, overactive bladder, stroke, irritable bowel syndrome, respiratory disease such as asthma and chronic obstructive pulmonary disease, dermatitis, mucositis, gastric/duodenal ulcer, inflammatory bowel syndrome, diabetes, and obesity.

DETAILED DESCRIPTION OF THE PREFERRED EMBODIMENTS

Hereinafter, the compounds of formula (I) in the invention are further illustrated.

The compounds of the general formula (I) mentioned above have a potent analgesic action as a property thereof. And additionally the compounds have a feature of a low irritancy. The excellent feature of the compounds of formula (I) in the invention largely depends on partial structures shown below, that is, a partial structure comprising a cyclohexane ring or a cyclohexene ring which has a specific substituent ("$R^3$" and "$R^4$" in (A), "$R^3$" in (B), or "=C(—$R^4$)—$R^3$" in (C)) at 4th position thereof.

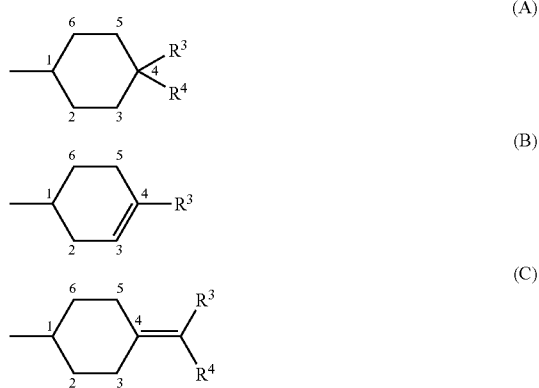

In other words, the structural feature of the compounds of formula (I) in the invention is the specific partial structure mentioned above and the bond between the specific partial structure and the other structure.

The physiologically acceptable salt of the compound of formula (I) means a physiologically acceptable acid addition salt of the compound of formula (I) which has a functional group in the structure to form an acid addition salt, or a physiologically acceptable base addition salt of the compound of formula (I) which has a functional group in the structure to form a basic addition salt. The example of the acid addition salt includes, for example, an inorganic acid salt such as hydrochloride, hydrobromide, hydroiodide, sulfate, perchlorate, and phosphate; an organic acid salt such as oxalate, malonate, maleate, fumarate, lactate, malate, citrate, tartrate, benzoate, trifluoroacetate, acetate, methanesulfonate, p-toluenesulfonate, and trifluoromethanesulfonate; and an amino acid salt such as glutamate and aspartate. The example of the base addition salt includes, for example, an alkali metal or alkaline earth metal salt such as sodium salt, potassium salt, and calcium salt; a salt with an organic base such as pyridine salt and triethylamine salt; and a salt with an amino acid such as lysine and arginine.

The compound of the invention also includes a hydrate and/or solvate thereof since the compound of formula (I) or a salt thereof may exist as a hydrate and/or solvate. That is, "the compound of the invention" includes N-substituted phenylacetamide derivatives of the above formula (I) and physiologically acceptable salts thereof as well as hydrates and/or solvates thereof.

In addition, the compound of formula (I) may have one or optionally more asymmetric carbon atoms or may have geometrical isomerism or axial chirality, and thus it may include several kinds of stereoisomers thereof. Herein, the compound of formula (I) of the invention includes the stereoisomers, mixtures thereof, and racemic compounds thereof.

The meanings of the definition in the compound of formula (I) of the invention are explained as follows.

The proviso of "X is a single bond when Y is a single bond" is added to clarify the definition of $R^3$. Namely, this makes it clear that $R^3$ should be defined only based on Z, not based on the combination of X and Z when $R^3$ is a hydrocarbon group such as an alkyl group.

The proviso of "X is a $C_{1-10}$ alkylene group when Y in the formula (B) or (C) is —O—" is added to exclude the compound wherein the above-defined Y is bound to the group of formula (B) or formula (C) directly or via alkenylene group or alkynylene group because the compound is generally unstable.

In addition, the proviso of "$R^4$ in formula (C) is not hydroxyl group" is added to avoid the duplex definition of formula (A) since the compound wherein $R^4$ in formula (C) is hydroxyl group usually exists in a tautomeric form (keto form).

When $R^3$ and $R^4$ in formula (A) or (C) are the same or different and are an alkyl group, an alkenyl group, or an alkynyl group; the group having the longer carbon chain should be defined as $R^3$.

Next, the terms used herein are explained hereinafter.

The term "alkyl group" means a straight or branched chain saturated hydrocarbon group, and for example, "$C_{1-4}$ alkyl group", "$C_{1-6}$ alkyl group" or "$C_{1-10}$ alkyl group" means an alkyl group having 1-4, 1-6 or 1-10 carbon atoms, respectively. The example of "$C_{1-4}$ alkyl group" includes methyl, ethyl, propyl, isopropyl, butyl, isobutyl, sec-butyl, tert-butyl, etc.; the example of "$C_{1-6}$ alkyl group" includes pentyl, isopentyl, neopentyl, hexyl, etc. in addition to the foregoing examples; and the example of "$C_{1-10}$ alkyl group" includes octyl, nonyl, decyl, etc. in addition to the foregoing examples. Said alkyl groups may include straight chain ones or branched chain ones.

The term "alkenyl group" means a straight or branched chain unsaturated hydrocarbon group which has at least one double bond; and for example, "$C_{2-10}$ alkenyl group" means an unsaturated hydrocarbon group containing 2-10 carbon atoms which has at least one double bond. The example thereof includes vinyl, allyl, 1-propenyl, isopropenyl, 1-, 2- or 3-butenyl, 1,3-butadienyl, 2-, 3- or 4-pentenyl, 2-methyl-2-butenyl, 3-methyl-1-butenyl, 3-methyl-2-butenyl, 4-methyl-1-pentenyl, 3,3-dimethyl-1-butenyl, 5-hexenyl, 3-octenyl, etc. Said alkenyl groups may include straight chain ones or branched chain ones. The number of the double bond in said alkenyl group may be one or two.

The term "$C_{2-10}$ alkynyl group" means a straight or branched chain unsaturated hydrocarbon group containing 2-10 carbon atoms which has at least one triple bond. The example thereof includes ethynyl, 1- or 2-propynyl, 1-, 2- or 3-butynyl, 1-methyl-2-propynyl, 3-hexynyl, etc.

The term "$C_{4-10}$ alkenylalkynyl group" means a straight or branched chain unsaturated hydrocarbon group containing 4-10 carbon atoms which has at least one double and at least one triple bond without limitation of the order of them. The example thereof includes 2-penten-4-ynyl, 3-penten-1-ynyl, 3,6,8-decatrien-1-ynyl, etc.

The term "$C_{3-8}$ cycloalkyl group" means a monocyclic saturated hydrocarbon group containing 3-8 carbon atoms. The example thereof includes cyclopropyl, cyclobutyl, cyclopentyl, cyclohexyl, cycloheptyl, cyclooctyl, etc. The number of carbon atoms in the cycloalkyl group formed by $R^3$ and $R^4$ taken together should include one of the carbon atom attached to $R^3$ and $R^4$.

The term "aryl group" means phenyl group or naphthyl group, and phenyl group is preferable.

The term "$C_{1-6}$ alkoxy group" means a straight or branched chain alkoxy group containing 1-6 carbon atoms. The example thereof includes methoxy, ethoxy, propoxy, isopropoxy, butoxy, isobutoxy, sec-butoxy, tert-butoxy, pentyloxy, hexyloxy, etc.

The alkylene group, alkenylene group, and alkynylene group defined in X group are each group which is given by removing one hydrogen atom from the terminal carbon atom of the above-mentioned alkyl group, alkenyl group and alkynyl group, respectively. In more detail, they are shown as follows.

The term "$C_{1-10}$ alkylene group" may include a straight chain one or a branched chain one, and the example thereof includes methylene, ethylene, trimethylene, propylene, tetramethylene, etc.

The term "$C_{2-10}$ alkenylene group" may include a straight chain one or a branched chain one, and is intended to have at least one double bond. The example thereof includes vinylene, propenylene, 2-pentenylene, etc.

The term "$C_{2-10}$ alkynylene group" may include a straight chain one or a branched chain one, and is intended to have at least one triple bond. The example thereof includes ethynylene, propynylene, etc.

The term "alkyl group substituted with fluorine atom(s)" means a group which is given by replacing 1 or more hydrogen atoms (e.g. 1-5 atoms, preferably 1-3 atoms) of the above-mentioned alkyl group with equivalent fluorine atom(s). The example thereof includes difluoromethyl, trifluoromethyl, 2,2,2-trifluoroethyl, pentafluoroethyl, 3,3,3-trifluoropropyl, 4-fluorobutyl, 4 4,4-trifluorobutyl, 5,5,5-trifluoropentyl, 6,6,6-trifluorohexyl, etc. The following groups substituted with fluorine atom(s): an alkylene group, an alkenylene group, an alkynylene group, an alkenyl group, an alkynyl group, an alkenylalkynyl group, a cycloalkyl group, a cycloalkyl moiety, an aryl group, an aryl moiety are also illustrated. In addition, the term "$C_{1-6}$ alkoxy group substituted with equivalent fluorine atom(s)" means a group which is given by replacing 1 or more hydrogen atoms (e.g. 1-5 atoms, preferably 1-3 atoms) of the above-mentioned $C_{1-6}$ alkoxy group with fluorine atom(s). The example thereof includes difluoromethoxy, trifluoromethoxy, 2,2,2-trifluoroethoxy, pentafluoroethoxy, 3,3,3-trifluoropropoxy, 4,4,4-trifluorobutoxy, etc.

Similarly, the alkylene group, the alkenylene group, the alkynylene group, the alkyl group, the alkenyl group, the alkynyl group, the alkenylalkynyl group, the cycloalkyl group, the cycloalkyl moiety, the aryl group, and the aryl moiety, each of which is substituted with hydroxyl group(s), mean each group which is given by replacing 1 or more hydrogen atoms (e.g. 1-5 atoms, preferably 1-3 atoms) of the above-mentioned each group with equivalent hydroxyl group(s). Also, each the group substituted with the other substituent is exemplified likewise.

The term "$C_{3-8}$ cycloalkylidene-$C_{1-3}$ alkyl group" means a group indicated by the following structure:

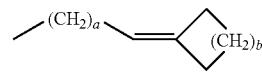

wherein "a" is an integer of 0-2 and "b" is an integer of 0-5. The example thereof includes cyclopropylidenemethyl group, cyclobutylidenemethyl group, cyclopentylidenemethyl group, cyclohexylidenemethyl group, cyclopropylideneethyl group, cyclobutylideneethyl group, cyclopentylideneethyl group, cyclohexylideneethyl group, cyclopentylidenepropyl group, cyclohexylidenepropyl group, etc.

The example of the complex group containing an alkyl whose number of carbon atoms is defined includes the alkyl moiety bound with each example of the above-mentioned various groups. For example, the number of the carbon atoms in "$C_{1-6}$ alkylcarbonyl" covers only the group or moiety (i.e. alkyl) directly following the number (1-6)-Thus, in the above case, "$C_{1-6}$" covers only the alkyl; and "$C_1$ alkylcarbonyl" denotes acetyl. The example of "$C_{1-4}$ alkyloxycarbonyl group" includes methoxycarbonyl, ethoxycarbonyl, propoxycarbonyl, isopropoxycarbonyl, butoxycarbonyl, isobutoxycarbonyl, tert-butoxycarbonyl, etc. The example of "$C_{1-4}$ alkylcarbonyl group" includes methylcarbonyl, ethylcarbonyl, propylcarbonyl, isopropylcarbonyl, butylcarbonyl, isobutylcarbonyl, tert-butylcarbonyl, etc. In addition, the example of "$C_{1-4}$ alkylcarbonyloxy group" includes methylcarbonyloxy, ethylcarbonyloxy, propylcarbonyloxy, isopropylcarbonyloxy, butylcarbonyloxy, isobutylcarbonyloxy, tert-butylcarbonyloxy, etc.

The example of "$C_{3-8}$ monocyclic saturated heterocyclyl group containing 1 or 2 oxygen atoms" includes tetrahydropyranyl, tetrahydrofuranyl, 1,3-dioxolanyl, 1,4-dioxanyl, etc. The number of carbon atoms in the $C_{3-8}$ should include one of the carbon atom attached to $R^3$ and $R^4$.

The example of each group defined in the compound (I) of the invention includes the followings.

$R^1$ denotes methoxy group, hydroxyl group or hydrogen atom, preferably methoxy group or hydroxyl group. $R^2$ denotes hydrogen atom, $C_{1-4}$ alkyl group, $C_{1-4}$ alkylcarbonyl group or arylcarbonyl group, preferably hydrogen atom.

"D" is the following formula (A), (B), or (C):

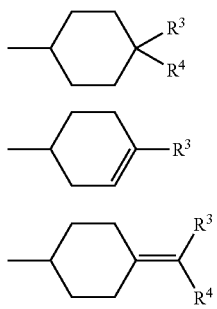

wherein $R^3$ and $R^4$ in formula (A) contain at least 3 carbon atoms in total, for example, 3-10 carbon atoms, preferably 3-8 carbon atoms (more preferably 3-7 carbon atoms, even more preferably 4-7 carbon atoms), or 4-10 carbon atoms. Or, $R^3$ may contain 3-10 carbon atoms, preferably 3-8 carbon atoms (more preferably 4-8 carbon atoms), or 4-10 carbon atoms. $R^3$ in formula (B) contains at least 3 carbon atoms, for example, 3-10 carbon atoms, preferably 3-8 carbon atoms (more preferably 4-8 carbon atoms), or 4-10 carbon atoms. $R^3$ and $R^4$ in formula (C) contain at least 2 carbon atoms in total, for example, 2-9 carbon atoms, preferably 2-8 carbon atoms (more preferably 2-7 carbon atoms), or 3-9 carbon atoms (more preferably 3-8 carbon atoms). Or, $R^3$ may contain 2-9 carbon atoms, preferably 2-8 carbon atoms (more preferably 2-7 carbon atoms, even more preferably 2-6 carbon atoms), or 3-9 carbon atoms.

When $R^3$ is defined as a group of —X—Y—Z,

X is a single bond, a $C_{1-10}$ alkylene group, a $C_{2-10}$ alkenylene group or a $C_{2-10}$ alkynylene group, Y is a single bond, —O—, —O—C(=O)—, —C(=O)— or —C(=O)—O, and Z is a straight or branched hydrocarbon group selected from the group consisting of a $C_{1-10}$ alkyl group, a $C_{2-10}$ alkenyl group, a $C_{2-10}$ alkynyl group, and a $C_{4-10}$ alkenylalkynyl group, in which the hydrocarbon may be optionally substituted with a $C_{3-8}$ cycloalkyl or an aryl; or a cyclic group selected from the group consisting of a $C_{3-8}$ cycloalkyl group, a $C_{3-8}$ cycloalkylidene-$C_{1-3}$ alkyl group, and an aryl group.

The preferable X is a single bond, a $C_{1-10}$ alkylene group or a $C_{2-10}$ alkenylene group, more preferably a single bond or a $C_{1-10}$ alkylene group, even more preferably a single bond. The preferable Y is a single bond or —O—, more preferably a single bond. The preferable Z is a straight or branched hydrocarbon group selected from the group consisting of a $C_{1-10}$ alkyl group (more preferably a $C_{1-7}$ alkyl group) and a $C_{2-10}$ alkenyl group (more preferably $C_{2-7}$ alkenyl group), in which the hydrocarbon may be optionally substituted with a $C_{3-8}$ cycloalkyl (preferably a $C_{3-6}$ cycloalkyl) or an aryl (preferably phenyl), preferably a $C_{3-8}$ cycloalkyl (more preferably $C_{3-6}$ cycloalkyl); or a cyclic group selected from the group consisting of a $C_{3-8}$ cycloalkyl group (more preferably a $C_{4-8}$ cycloalkyl group), a $C_{3-8}$ cycloalkylidene-$C_{1-3}$ alkyl group (more preferably a $C_{3-6}$ cycloalkylidene-$C_{1-2}$ alkyl group), and an aryl group (more preferably phenyl).

The above-mentioned alkylene group, alkenylene group, alkynylene group, alkyl group, alkenyl group, alkynyl group, and alkenylalkynyl group defined in X and Z may be substituted with 1-5 substituents selected from the group consisting of fluorine atoms and hydroxyl groups (preferably, may be substituted with 1-5 fluorine atoms); the cycloalkyl group and cycloalkyl moiety defined in Z may be substituted with 1-5 substituents selected from the group consisting of fluorine atoms, hydroxyl groups and $C_{1-6}$ alkyl groups. The aryl group or aryl moiety defined in Z group may be substituted with 1-5 substituents selected from the group consisting of fluorine atoms, hydroxyl groups, $C_{1-6}$ alkyl groups optionally substituted with 1-5 fluorine atoms, $C_{1-6}$ alkoxy groups optionally substituted with 1-5 fluorine atoms, nitro groups, amino groups, cyano groups, $C_{1-4}$ alkyloxycarbonyl groups, $C_{1-4}$ alkylcarbonyloxy groups, carboxyl groups, and methylenedioxy groups. The preferable Z is a straight or branched hydrocarbon group selected from $C_{1-7}$ alkyl group and $C_{2-7}$ alkenyl group, in which the hydrocarbon may be substituted with a $C_{3-8}$ cycloalkyl; or a cyclic group selected from the group consisting of a $C_{3-8}$ cycloalkyl group and a $C_{3-8}$ cycloalkylidene-$C_{1-3}$ alkyl group; and the alkyl group or the alkenyl group may be substituted with 1-5 fluorine atoms.

More preferably, Z is a straight or branched hydrocarbon group selected from a $C_{1-7}$ alkyl group and a $C_{2-7}$ alkenyl group, in which the hydrocarbon may be substituted with 1-5 of fluorine atoms or $C_{3-8}$ cycloalkyl groups. Said hydrocarbon groups may include straight chain ones or branched chain ones. And the preferable Z is a straight or branched hydrocarbon group selected from a $C_{1-7}$ alkyl group and a $C_{2-7}$ alkenyl group.

$R^4$ means hydrogen atom, hydroxyl group, a $C_{1-4}$ alkyl group, a $C_{2-4}$ alkenyl group or a $C_{2-4}$ alkynyl group, preferably hydrogen atom or a $C_{1-4}$ alkyl group, more preferably hydrogen atom.

And $R^3$ and $R^4$ may be taken together to form a $C_{3-8}$ cycloalkyl group or a saturated $C_{3-8}$ heteromonocyclyl group containing 1 or 2 oxygen atoms, each of which may be optionally substituted with 1-5 $C_{1-6}$ alkyl groups; in this case, the preferable example is a $C_{4-7}$ cycloalkyl group or a saturated $C_{3-6}$ heteromonocyclyl group containing 1 oxygen atom, and more preferably a $C_{4-7}$ cycloalkyl group.

The examples of the compound of formula (I) include the compounds of the following Examples as well as physiologically acceptable salts, or hydrates or solvates thereof.

The following abbreviate symbols are optionally used herein to simplify the chemical names.

Me: methyl group, Et: ethyl group, t-: tert-, n-: normal, Ms: methanesulfonyl group, Boc: tert-butoxycarbonyl group, Ph: phenyl group, Tr: triphenylmethyl group, THF: tetrahydrofuran, DMF: N,N-dimethylformamide, TFA: trifluoroacetic acid, P-: protective group.

Manufacturing Process of the Compounds of the Invention

The compounds of formula (I) and physiologically acceptable salts thereof are unknown, which can be prepared according to the following processes, the below-mentioned Examples or any processes known in the art.

The compound used in the following processes may be a salt thereof the same as the salt of the compound of formula (I) as far as the salt does not disturb the reaction.

When any starting material in each of the following reactions includes any substituent(s) which may be undesirably reactive such as amino group, carboxyl group, hydroxyl group, and carbonyl group; the substituent can be protected by introducing a conventional protective group to the substituent. And the protective group can be optionally removed to give the desired compound.

The example of the protective group using for amino group includes an alkylcarbonyl (e.g. acetyl, propionyl, etc.), formyl, phenylcarbonyl, an alkyloxycarbonyl (e.g. methoxycarbonyl, ethoxycarbonyl, t-butoxycarbonyl, etc.), phenyloxycarbonyl, aralkyloxycarbonyl (e.g. benzyloxy-carbonyl, etc.), triphenylmethyl, phthaloyl, toluene-sulfonyl, benzyl, etc.

The example of the protective group using for carboxyl group includes alkyl (e.g. methyl, ethyl, propyl, isopropyl, butyl, tert-butyl, etc.), phenyl, benzyl, triphenylmethyl, silyl (e.g. trimethylsilyl, tert-butyldimethylsilyl, etc.), etc.

The example of the protective group using for hydroxyl group includes methyl, tert-butyl, allyl, a substituted methyl (e.g. methoxymethyl, methoxyethoxymethyl, etc.), ethoxyethyl, tetrahydropyranyl, tetrahydrofuranyl, triphenylmethyl, an aralkyl (e.g. benzyl, etc.), an alkylcarbonyl (e.g. acetyl, propionyl, etc.), formyl, benzoyl, an aralkyloxycarbonyl (e.g. benzyloxycarbonyl, etc.), silyl, etc.

Protecting a carbonyl group is carried out by transforming the carbonyl group into an acyclic ketal (e.g. dimethyl ketal, diethyl ketal, etc.) thereof or a cyclic ketal (e.g. 1,3-dioxolane, 1,3-dioxane, etc.) thereof.

Process A

The compound of the invention can be prepared by the condensation of the following compound of formula (II) and the following compound of formula (III).

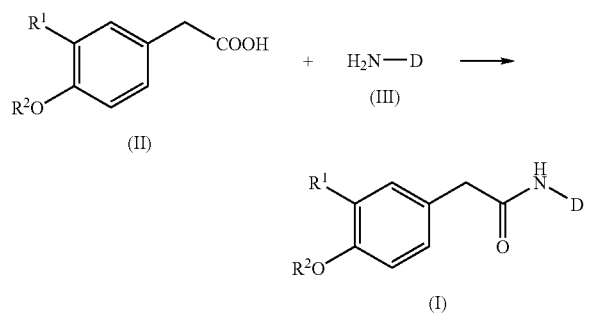

Wherein $R^1$, $R^2$ and D are as defined in the above [1].

The reaction of the compound of formula (II) and the compound of formula (III) is carried out under the reaction condition which is generally used in amide-forming reaction. The compound of formula (II) may be reacted with the compound of formula (III) after it is converted into a reactive derivative at the carboxyl group thereof.

The reactive derivative of the carboxyl group of the compound of formula (II) is, for example, a lower alkyl ester (especially methyl ester), an active ester, an acid anhydride, an acid halide (especially acid chloride). The active ester is, for example, p-nitrophenyl ester, N-hydroxysuccinimide ester, pentafluorophenyl ester. The acid anhydride is, for example, a mixed acid anhydride prepared with ethyl chlorocarbonate, isobutyl chlorocarbonate, isopentanoic acid, and pivalic acid.

When the compound of formula (II) per se is used, the reaction is generally carried out in the presence of a condensing agent. The example of the condensing agent includes N,N'-dicyclohexylcarbodiimide, 1-ethyl-3-(3-dimethylaminopropyl)carbodiimide hydrochloride, N,N'-carbonyldiimidazole, benzotriazol-1-yl-oxytris-(pyrrolidino)phosphonium hexafluorophosphate, etc. These condensing agents can be used alone or in connection with peptide synthetic reagent such as N-hydroxysuccinimide and N-hydroxybenzotriazole.

The reaction of the compound of formula (II) or a reactive derivative thereof and the compound of formula (III) is carried out with/without a solvent. The solvent used should be selected depending to the starting compound, etc. and includes, for example, toluene, tetrahydrofuran, dioxane, ethylene glycol dimethyl ether, dichloromethane, chloroform, ethyl acetate, acetone, acetonitrile, dimethylformamide, etc. These solvents may be used alone or as a mixture of 2 or more of the solvents. The compound of formula (III) may be used as an acid addition salt such as hydrochloride, which can be converted to a free base thereof in the reaction system.

The above-mentioned reaction is generally carried out in the presence of a base. The example of the base includes an inorganic base such as potassium carbonate and sodium bicarbonate; and an organic base such as triethylamine, ethyldiisopropylamine, N-methylmorpholine, pyridine, and 4-dimethylaminopyridine. The reaction temperature is varied depending on the starting compound, and generally is about −30° C. to about 150° C., preferably about −10° C. to about 70° C.

The above-mentioned compound of formula (II) is a known compound or can be prepared according to the process for the known compound. For example, it can be prepared according to methods described in J. Am. Chem. Soc., 16, 3340 (1973), Synthetic Communication, 33, 59 (2003), J. Med. Chem., 39, 2939 (1996), or similar methods thereof.

In addition, the above compound of formula (III) is also a known compound or can be prepared according to the process for the known compound. Hereinafter, some typical processes are illustrated.

Process of the Compound of Formula (III) (1)

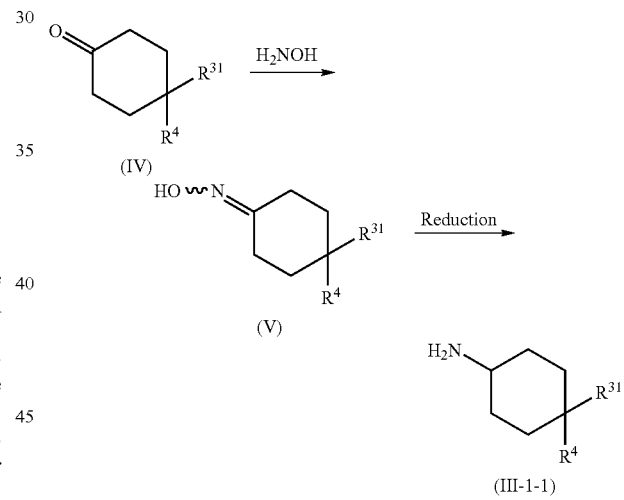

Wherein $R^{31}$ is defined as a group: $-X^1-Y^1-Z^1$;

$X^1$ is the same as X defined in the above [1], $Y^1$ is a single bond or $-O-$, $Z^1$ is the same as Z defined in the above [1], provided that $X^1$ is a single bond when $Y^1$ is a single bond;

$R^4$ is defined in the above [1]; or $R^{31}$ and $R^4$ are taken together to form a $C_{3-8}$ cycloalkyl group or a saturated $C_{3-8}$ heteromonocyclyl group containing 1 or 2 oxygen atoms, each of which may be optionally substituted with a $C_{1-6}$ alkyl group(s);

further provided that $R^{31}$ and $R^4$ contain at least 3 carbon atoms in total.

Using the compound of formula (IV) as a starting material, the compound of formula (III-1-1) can be prepared via the compound of formula (V) which is prepared according to a method of Chem. Ber., 88, 1906 (1955), etc. and then is reduced.

In actual procedure, the compound of formula (IV) can be reacted with hydroxylamine hydrochloride in the presence of a base to give the compound of formula (V). As a base used in the reaction, for example, sodium carbonate, pyridine, triethylamine, sodium acetate, etc. can be used; and as the solvent used in the reaction, for example, methanol, ethanol, water or the above base as a solvent can be used. The reaction is generally carried out at about 0° C.-150° C., and the reaction time is about 1-48 hours. In addition, the preparation of the above compound of formula (III-1-1) from the above compound of formula (V) can be carried out by a conventional reduction.

The compound of formula (IV) which is the starting material is commercially available or can be prepared according to a known method, for example, Tetrahedron Lett., 34, 3209 (1979); Chem. Ber., 118, 3332 (1985); Org. Mass Spect., 24, 773 (1989), etc. Additionally, it can be prepared by hydrogenating the following compound of formula (VI) according to a method, for example, J. Org. Chem., 45, 5399 (1980); or J. Org. Chem., 41, 3338 (1976) (see Example 9).

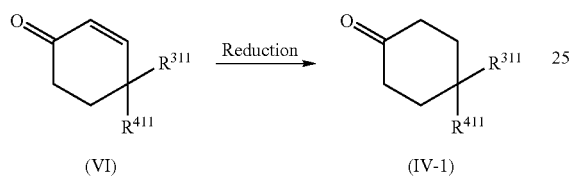

Wherein $R^{311}$ and $R^{411}$ both are a group selected from the above-mentioned $R^{31}$ and $R^4$, which is not reacted under the reduction condition, such as a $C_{1-10}$ alkyl group.

Process of the Compound of Formula (III) (2)

Using the compound of formula (VII) (or formula (IV')) as a starting material, the compound of formula (III-1-2) can be prepared according to the following process.

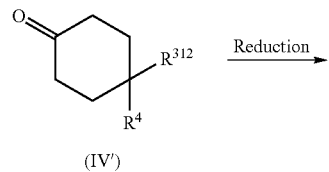

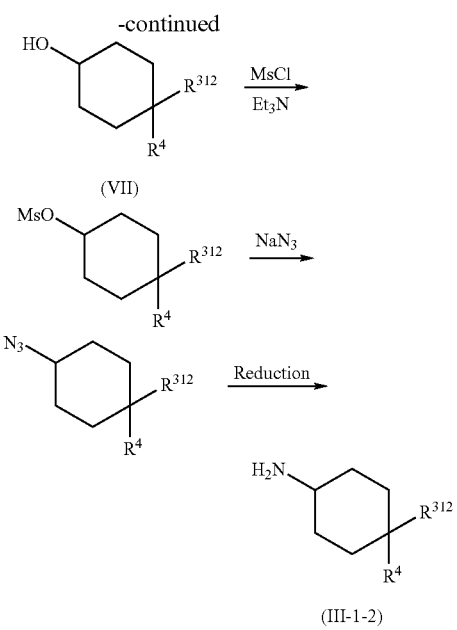

Wherein $R^{312}$ is the same as $R^3$ defined in the above [1] provided that Y is not —C(═O)—, and $R^4$ is the same as $R^4$ defined in the above [1].

Namely, according to a method, for example, J. Org. Chem., 22, 238 (1957); or J. Am. Chem. Soc., 77, 951 (1955), the compound of formula (VII) having the hydroxyl group is transformed into an azide derivative, and the azide derivative can be reduced to give the compound of formula (III-1-2). In actual procedure, first of all, the compound of formula (VII) having the hydroxyl group is reacted with methanesulfonyl chloride in the presence of a base such as triethylamine to give a methanesulfonyloxy (MsO—) derivative. And said derivative is transformed into an azide derivative by using sodium azide, then the azide derivative is reduced into an amino group by various method, for example, hydrogenation with Pd, Pt, Raney nickel, etc., reduction with a hydride such as LiAlH$_4$, or reduction with triphenylphosphine, thereby the compound of formula (III-1-2) can be prepared.

The compound of formula (VII) is a known compound, or can be prepared using a known method, for example, reducing the compound of formula (IV').

Process of the Compound of Formula (III) (3)

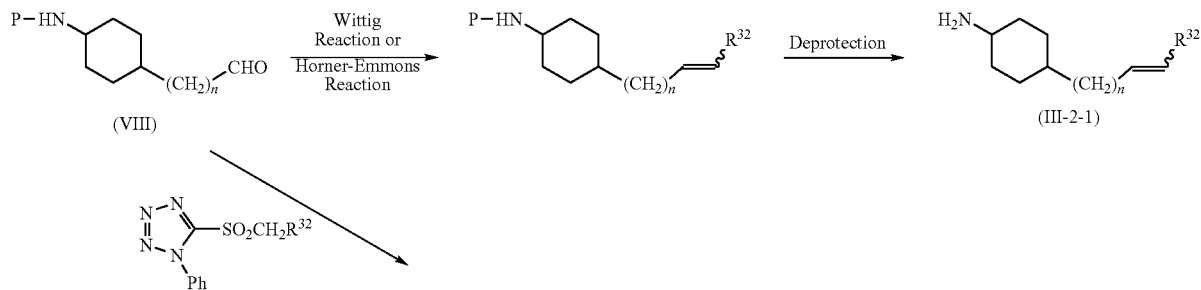

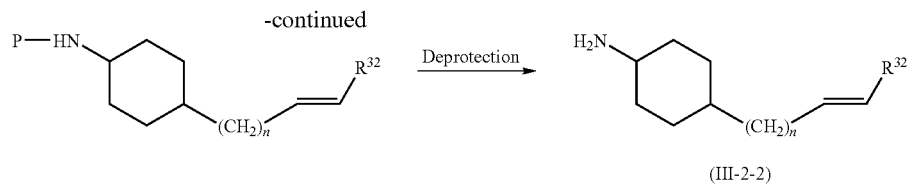

(III-2-2)

Wherein n is an integer of 0-3; $R^{32}$ is an alkyl group, an alkenyl group, an alkynyl group, a cycloalkyl group, an alkylcarbonyl group, an alkyloxycarbonyl group or an aryl group, which may be optionally substituted with fluorine atom(s), hydroxyl group(s), etc.

The above compound of formula (III-2-1) can be prepared for example, by reacting the compound of formula (VIII) with the corresponding triphenylphosphonium halide compound (Org. React., 14, 270 (1965)) or phosphonic acid diester compound (Chem. Rev., 74, 87 (1974)) in the presence of a base such as butyl lithium and potassium t-butoxide in a solvent such as THF and DMF at –80° C. to 50° C. (Wittig reaction or Horner-Emmons reaction) and then removing the protective group (P) of the compound. Wittig reaction mainly gives Z form thereof and Horner-Emmons reaction mainly gives E form thereof, but it is not limited.

The above compound of formula (III-2-2) which is E form can be prepared according to a method described in Synlett, 26 (1998); Tetrahedron, 58, 4425 (2002), etc. In actual procedure, first of all, the compound of formula (VIII) and the corresponding 1-phenyl-1H-tetrazole reagent having sulfonyl group in 5-position can be reacted in the presence of a base such as potassium hexamethyldisilazane, in a solvent such as DME and THF, at –70° C. to 50° C.; and then the protective group (P) of the compound is removed to prepare the desired compound.

The above compound of formula (VIII) is commercially available, or can be prepared according to a known method or a similar method thereof.

Process of the Compound of Formula (III) (4)

The manufacturing process of the compound wherein Y is —O— is shown below as one example.

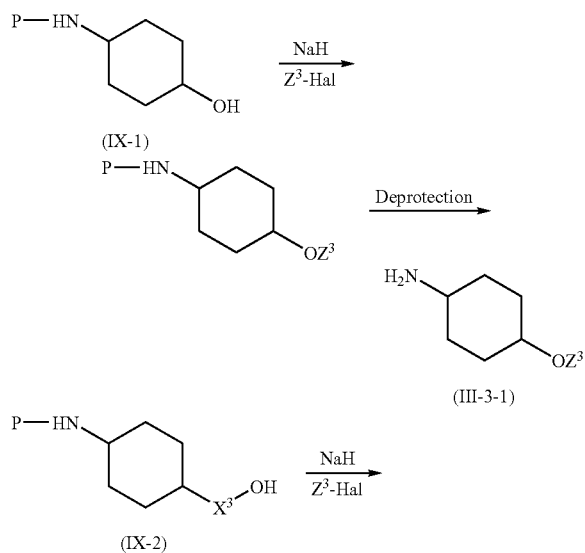

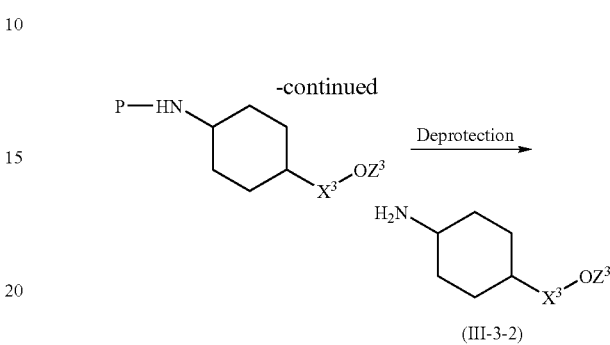

(III-3-2)

Wherein $X^3$ is a $C_{1-10}$ alkylene, a $C_{2-10}$ alkenylene, or a $C_{2-10}$ alkynylene, which may be optionally substituted;

$Z^3$ is a $C_{1-10}$ alkyl group, a $C_{2-10}$ alkenyl group, a $C_{2-10}$ alkynyl group, or a $C_{4-10}$ alkenylalkynyl group, which may be optionally substituted;

$Z^3$ in the compound of formula (III-3-1) or $X^3$ and $Z^3$ in the compound of formula (III-3-2) contain at least 3 carbon atoms in total; and Hal is chlorine, bromine or iodine atom.

The preparation of the compound (III-3-1) from the compound (IX-1) or the preparation of the compound (III-3-2) from the compound (IX-2) can be carried out according to a method, for example, J. Am. Chem. Soc., 70, 3098 (1948). In actual procedure, the compound (IX-1) or the compound (IX-2) can be reacted with the corresponding organic halide reagent ($Z^3$-Hal) in the presence of sodium hydride, and then the protective group (P) of the reaction product is removed to prepare the desired compound (III-3-1) or compound (III-3-2).

The compound of formula (IX-1) or the compound of formula (IX-2) which is the starting material is commercially available or can be prepared according to a known method.

Process of the Compound of Formula (III) (5)

The manufacturing process of the compound of formula (III) wherein Y is —O—C(=O)— is shown below as one example. The preparation of the compound of formula (III-4) from the compound of formula (IX-1) can be carried out according to the following process.

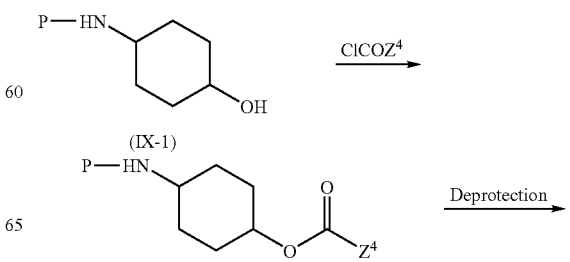

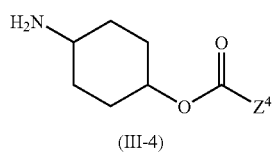

(III-4)

Wherein $Z^4$ is the same as Z defined in the above [1].

In actual procedure, the compound of formula (IX-1) can be reacted with the corresponding $ClCOZ^4$ in the presence of a base such as potassium carbonate, triethylamine, and pyridine, in a solvent such as dichloromethane, tetrahydrofuran, at −20° C. to 50° C. to give an ester compound thereof, and then the protective group (P) is removed to prepare the compound of formula (III-4).

Process of the Compound of Formula (III) (6)

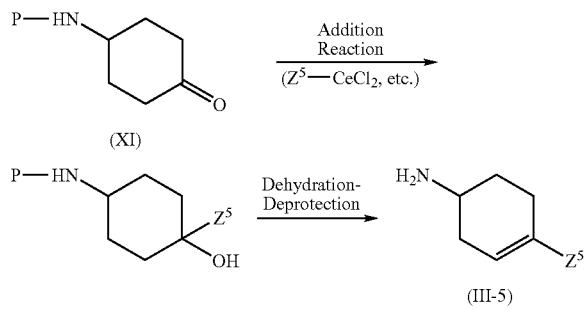

(XI)

(III-5)

Wherein $Z^5$ is an optionally-substituted $C_{1-10}$ alkyl group containing at least 3 carbon atoms.

The preparation of the compound (III-5) from the compound (XI) can be carried out by addition reaction and then dehydration, according to a method, for example, J. Org. Chem., 49, 3904 (1984). In actual procedure, after protecting a functional group which is affectable for the reaction (e.g. hydroxyl group), the compound (XI) can be alkylated with the corresponding organo-cerium compound ($Z^5$-CeCl$_2$, etc.), and then dehydrated and deprotected to prepare the desired compound.

The compound of formula (XI) which is the starting material can be prepared according to a known method.

Process of the Compound of Formula (III) (7)

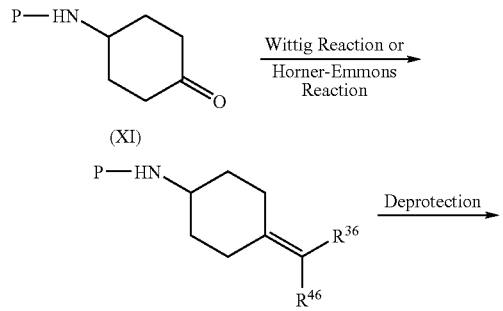

(XI)

(III-6-1)

Wherein $R^{36}$ is a $C_{1-10}$ alkyl group, a $C_{2-10}$ alkenyl group, a $C_{2-10}$ alkynyl group, a $C_{3-8}$ cycloalkyl group, a $C_{1-10}$ alkylcarbonyl group, a $C_{1-10}$ alkyloxycarbonyl group, or an aryl group, which may be optionally substituted with fluorine atom(s), hydroxyl group(s) and so on; $R^{46}$ is a hydrogen atom, a $C_{1-4}$ alkyl group, a $C_{2-4}$ alkenyl group, or a $C_{2-4}$ alkynyl group; $R^{36}$ and $R^{46}$ contain at least 2 carbon atoms in total.

The preparation of the above compound of formula (III-6-1) from the above compound of formula (XI) can be carried out, for example, in a similar manner of the above-mentioned process of the compound of formula (III) (3).

Process of the Compound of Formula (III) (8)

Using the compound of formula (XII) as a starting material, the compound of formula (III-6-2) can be prepared according to the following process.

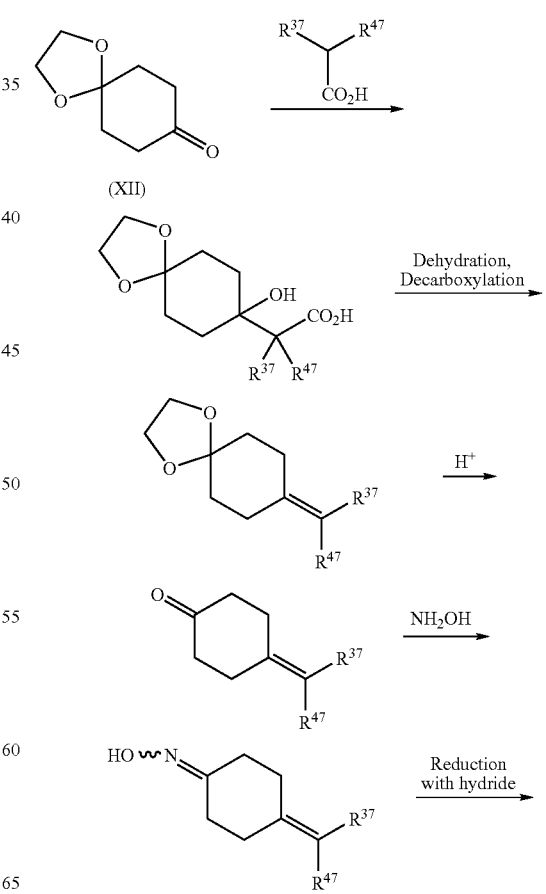

(XII)

-continued

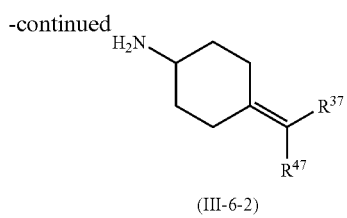

(III-6-2)

Wherein $R^{37}$ is a $C_{1-10}$ alkyl group, a $C_{2-10}$ alkenyl group, a $C_{2-10}$ alkynyl group, etc., which may be optionally substituted with fluorine atom(s) or hydroxyl group(s); $R^{47}$ is a $C_{1-4}$ alkyl group, a $C_{2-4}$ alkenyl group, or a $C_{2-4}$ alkynyl group; alternatively $R^{37}$ and $R^{47}$ are taken together to form a $C_{3-8}$ cycloalkyl group or a saturated $C_{3-8}$ heteromonocyclyl group containing 1 or 2 oxygen atoms, each of which may be optionally substituted with a $C_{1-6}$ alkyl group(s).

Namely, according to a method, for example, Tetrahedron Lett., 19, 1548 (1975); or Synthesis, 1053 (1990), the compound of formula (III-6-2) can be prepared by reacting the compound of formula (XII) with the carboxylic acid; dehydrating, decarboxylating, and acid-treating the reacting product; and then transforming ketone derivative into amino one. In actual procedure, first of all, the carboxylic acid is transformed into dianion derivative by treating it with a base such as lithiumdiisopropyl amide. The resulting derivative is reacted with the compound of formula (XII) having the ketone group to give a carboxylic acid derivative having hydroxyl group in β position. Then, the product can be heated in the presence of a dehydrating agent such as N,N-dimethylformamide dineopentyl acetal to give a compound having an alkenyl group. And then the product is treated with an acid to give a ketone derivative. The ketone derivative is transformed into an oxime one by hydroxylamine, then said oxime derivative can be transformed an amino one by reduction with a hydride such as $LiAlH_4$ to prepare the compound of formula (III-6-2). The compound of formula (XII) which is the starting material is commercially available.

Process B

When group D of the compound of formula (I) has a unsaturated binding group such as an alkenyl group, the reduction of the compound can provide the compound of formula (I) wherein group D has no unsaturated binding group, for example a alkyl group.

Process C

When $R^2$ in the compound of formula (I) is a hydrogen atom, the acylation of the compound can provide the compound of formula (I) wherein $R^2$ is a $C_{1-4}$ alkylcarbonyl group or an arylcarbonyl group.

The compound of formula (I) prepared in the above-mentioned processes can be isolated/purified according to a conventional method such as chromatography, recrystallization, re-precipitation, etc. In addition, an optically active isomer thereof can be prepared with a chiral column or by an optical resolution; and a geometrical isomer such as a cis form and a trans form can be prepared using the corresponding starting material.

The compound of formula (I) may be given in a free base form or an acid addition salt form depending on the type of functional group in the structure, the selection of the starting material, or the reacting condition, which can be converted to the compound of formula (I) according to a conventional method. On the contrary, the compound of formula (I) having a group that can be formed to an acid addition salt in the structure can be transformed into an acid addition salt thereof using a variety of acids according to a conventional method.

The compound of the invention and a physiologically acceptable salt thereof and a hydrate or solvate thereof have a potent analgesic action. Additionally, for a weak irritancy of the compound, they are useful not only for oral administration, but also for parenteral administration such as percutaneous, topical, nasal and intravesical-injection administrations. Therefore, the compounds of the invention are useful as an analgesic agent and an anti-inflammatory agent, as well as a medicament for treating neuropathic pain such as diabetic neuropathic pain, postherpetic neuralgia, trigeminal neuralgia, and HIV-multiple neuropathic pain; and pain caused by rheumatoid arthritis or osteoarthritis, which are not sufficiently treated with existing analgesic agents. Furthermore, the compounds are also useful as a medicament for treating and/or preventing migraine or cluster headache, pruritus, allergic and nonallergic rhinitis, overactive bladder, stroke, irritable bowel syndrome, respiratory disease such as asthma and chronic obstructive pulmonary disease, dermatitis, mucositis, gastric/duodenal ulcer, inflammatory bowel syndrome, diabetes, and obesity.

The preferable administration route of the compound of the invention is oral or parenteral administration, more preferably percutaneous administration which is a kind of parenteral administration. The dosage of the compound of the invention can vary depending upon the kind of the compound, administration form, administration route, conditions and age of patient, and so on, generally 0.005 to 150 mg/kg/day, preferably 0.05 to 20 mg/kg/day, which can be administrated in one or several portions.

The compound of the invention is administrated as a pharmaceutical composition prepared by mixing the compound with pharmaceutical carrier(s). The example of the pharmaceutical composition includes an oral formulation such as tablets and capsules; an external liquid formulation such as ointment and intravesical-infusion; an external formulation such as cataplasm, inhalant, and nasal drop; an injection for intrabody-cavity such as intradermal injection, subcutaneous injection or intraperitoneal injection, and intraarticular injection. These pharmaceutical compositions can be prepared according to a conventional method.

The pharmaceutical carrier used for pharmaceutical composition is a material that is conventional in the pharmaceutical field and inert to the compound of the present invention. The example of the pharmaceutical carrier for preparing tablets and capsules includes an excipient such as lactose, corn starch, white soft sugar, mannitol, calcium sulfate, and microcrystalline cellulose; a disintegrating agent such as croscarmellose sodium, modified starch, carmellose calcium, crospovidone, and low substituted hydroxypropylcellulose; a binding agent such as methylcellulose, gelatin, acacia, ethylcellulose, hydroxypropylcellulose, and povidone; a lubricant such as light anhydrous silicic acid, magnesium stearate, talc, sucrose esters of fatty acids, and hydrogenated oil. The tablets of the invention may be coated with a coating agent such as carnauba wax, hydroxypropylmethylcellulose, macrogol, cellulose acetate phthalate, hydroxypropyl-methylcellulose acetate phthalate, white soft sugar, titanium oxide, sorbitan esters of fatty acid, and calcium phosphate, according to a conventional method.

The external formulation includes, but not limited thereto, what an active ingredient is dissolved or mixed-dispersed with a substrate to give a cream, paste, jelly, gel, emulsion, suspension, or liquid form, etc. (ointment, external liquid formulation, etc.); what an active ingredient and a percutaneous-penetration enhancer is dissolved or mixed-dispersed with a substrate and then is extended on a support material such as polyethylene, polypropylene, and polyvinyl chloride (cataplasm, tape formulation, etc.), inhalant, nasal drop, etc. The above-mentioned substrate may be any substrate as far as it is physiologically acceptable, it is possible to use as, for example, ointment, external liquid formulation, etc. including for example, oil substrate, water-soluble substrate, hydrophilic substrate, etc.

The example of the oil substrate (or solvent) includes oils such as olive oil, purified lanolin, squalane, silicon oil, castor oil, olive oil, soybean oil, and cotton seed oil; hydrocarbons such as liquid paraffin, white petrolatum, yellow petrolatum, and paraffin; higher fatty acids such as lauric acid, myristic acid, stearic acid, and oleic acid; higher alcohols such as lauryl alcohol, myristyl alcohol, oleyl alcohol, and cetyl alcohol; waxes such as yellow beeswax, carnauba wax, and white beeswax; esters such as cholesterol ester, ethylene glycol monoalkyl ester, propylene glycol monoalkyl ester, glyceryl monostearate, sorbitan esters of fatty acid, isopropyl myristate, and isopropyl palmitate. The example of the water-soluble substrate includes polyethylene glycol, etc. The hydrophilic substrate which is given by dispersing/homogenizing the above-mentioned oil substrate (or solvent) and water-soluble solvent (polyethylene glycol, glycerin, propylene glycol, ethanol, etc.) or aqueous solvent (sorbitol solution, water, etc.) together with a suitable surfactant includes hydrophilic ointment, vanishing cream, absorptive ointment, cold cream, hydrophilic petrolatum, etc. And furthermore, jelly-base substrate (e.g. aqueous gel of carboxyvinyl polymer), non-adipose ointment (e.g. polyethylene glycol ointment), etc. are exemplified.

The base of the cataplasm includes, for example, a higher molecular substrate such as polyvinyl pyrrolidone, polyisobutylene, vinyl acetate copolymer, acryl copolymer; and a plasticizer such as glycerin, propylene glycol, polyethylene glycol, triethyl citrate, acetyl triethyl citrate, diethyl phthalate, diethyl sebacate, dibutyl sebacate, and acetylated monoglyceride. The above-mentioned percutaneous-penetration enhancer may be any agent as far as it is pharmacologically acceptable, including for example, an alcohol such as ethanol and diethylene glycol; a polar solvent such as dodecylpyrrolidone; urea; ethyl laurate; azone; olive oil, etc.

Furthermore, an inorganic filler such as kaolin, bentonite, zinc oxide, and titanium oxide; a viscosity regulator such as agarose, carrageenan, alginic acid or a salt thereof, tragacanth, acacia gum, methylcellulose, carboxymethylcellulose, hydroxyethylcellulose, carboxyvinyl polymer, gelatin, corn starch, xanthan gum, dextrin, and a polymer such as polyvinyl alcohol, etc; an antioxidant; a pH regulator; a moisturizing agent such as glycerin, propylene glycol may be added thereto, as appropriate. In addition, a surfactant may be added thereto, and the example of the surfactant includes an ionic surfactant such as an alkaline salt of fatty acid (e.g. potassium laurate, potassium palmitate, and potassium myristate); and sulfate esters (e.g. sodium lauryl sulfate, sodium cetylsulfate, and sulfated castor oil), and a non-ionic surfactant such as a sorbitan esters of fatty acid (e.g. sorbitan stearate, sorbitan monooleate, sorbitan sesquioleate, and sorbitan trioleate, what is called "span"); polysorbate 20, polysorbate 40, polysorbate 60, polysorbate 65, polysorbate 80, polysorbate 85, polyoxyethylene sorbitan esters of fatty acid (what is called "Tween"); polyoxyethylene hydrogenated castor oil (what is called "HCO"); a polyoxyethylene alkyl ether (e.g. polyoxyethylene lauryl ether, polyoxyethylene cetyl ether, and polyoxyethylene oleyl ether); polyethylene glycol esters of fatty acid (e.g. polyethylene glycol monolaurate, polyethylene glycol monostearate); and poloxamer (what is called "Pluronic"). Furthermore, lecithin (including purified phospholipid isolated from lecithin such as phosphatidylcholine and phosphatidylserine) or its derivative such as a hydrogen-addition compound thereof may be added thereto.

The inhalant can be prepared by making the compound of the invention in the form of powder or liquid; adding the transformed compound in a spray-base for inhalant or a carrier; and charging the resulting mixture into an inhalant vessel such as a constant-shot spray inhaler and a dry powder inhaler. It may be a propellant, an aerosol, and a spray. As the above-mentioned inhalational propellant, a conventional known propellant can be used and includes, for example, a chlorofluorocarbon (CFC) gas such as CFC-11, CFC-12, CFC-21, CFC-22, CFC-113, CFC-114, CFC-123, CFC-142c, CFC-134a, CFC-227, CFC-C318, 1,1,1,2-tetrafluoroethane; a alternatives gas for CFC such as HFA-227 and HFA-134a; a hydrocarbon gas such as propane, isobutane, and butane; diethyl ether, nitrogen gas, carbon dioxide gas, etc. As the above-mentioned career, a conventional known carrier can be used and includes sugars, sugar alcohols, amino acids, etc.

The liquid for inhalant can be prepared with additives optionally selected from a preservative (e.g. benzalkonium chloride, paraben, etc.), a coloring agent, a buffer agent (e.g. sodium phosphate, sodium acetate, etc.), an isotonic agent (sodium chloride, concentrated glycerin, etc.), a viscosity agent (carboxyvinyl polymer, etc.), a preservative (e.g. benzalkonium chloride, paraben, etc.), an absorption enhancing agent, etc, as appropriate.

The powder for inhalant can be prepared with additives optionally selected from a lubricant (e.g. stearic acid, a salt thereof, etc.), a binding agent (e.g. starch, dextrin, etc.), an excipient (e.g. lactose, cellulose, etc.), a coloring agent, an absorption enhancing agent, etc, as appropriate.

The nasal drop can be formed in a variety of formulation such as drop type, paint type, and spray type. The spray-type formulation includes hand pump-type nasal drop which is sprayed by manually moving a pump head of the vessel; aerosol-type nasal drop which is sprayed automatically by moving a valve of the vessel wherein propellant of pressured gas (e.g. air, oxygen, nitrogen, carbon dioxide, mixed gas) is charged; etc.

The injection of the invention may be a solution prepared by adding the compound of the invention to a solution of distilled water for injection, further optionally including a solubilizer, a buffer agent, a pH regulator, an isotonic agent, an analgesic, a preservative, etc.; and a suspension prepared by suspending the compound of the invention in distilled water for injection or plant oil, optionally including other substrates, suspending agent, thickening agent, etc. as appropriate. In addition, an extemporaneous injection preparation using powdered or lyophilized formulation can be also used, optionally including an excipient, etc.

The amount of the compound of the invention in the pharmaceutical composition is varied depending its formulation and generally it is 0.0025-20% (w/w) per total amount of the composition. The pharmaceutical composition of the invention may include other therapeutically active ingredient.

EXAMPLE

Hereinafter, the present invention is further illustrated by Examples, but should not be construed to be limited thereto. The identification of the compounds was carried out using NMR spectrum (300 MHz or 400 MHz) on so on. The determination of ratio of isomers or cis/trans forms was given by the calculation based on the area ratio thereof using HPLC.

Example 1

Preparation of N-(4-butyl-3-cyclohexenyl)-2-(4-hydroxy-3-methoxyphenyl)acetamide

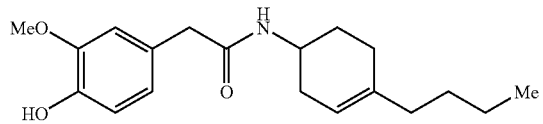

(1) Under nitrogen atmosphere, anhydrous cerium chloride (4.63 g) was added to anhydrous tetrahydrofuran (50 ml), and the mixture was stirred at room temperature for 2 hours. After the suspension was cooled to −78° C., 1.6 M butyl lithium in hexane (6.40 ml) was added to the suspension and then the mixture was stirred for 1 hour. A solution of t-butyl 4-oxocyclohexylcarbamate (2.36 g) in anhydrous tetrahydrofuran (50 ml) was added to the reaction mixture over 10 minutes, and the mixture was gradually warmed to about 25° C. and then stirred overnight. After a saturated aqueous ammonium chloride was added to the reaction mixture, the mixture was filtrated through Celite. The filtrate was extracted with ethyl acetate, and the organic layer was washed with brine, dried over sodium sulfate, and the solvent was removed in vacuo. The residue was purified by a silica gel chromatography (eluent: chloroform/methanol=100/1) to give 2.53 g of t-butyl 4-butyl-4-hydroxycyclohexylcarbamate.

(2) The above product (1) (900 mg) was dissolved in toluene (15 ml), p-toluenesulfonic acid monohydrate (1.27 g) was added to the solution, and the mixture was heated at 100° C. for 2 hours. Aqueous potassium carbonate was added to the reaction mixture, and the mixture was extracted with ethyl acetate. The organic layer was washed with brine, then dried over sodium sulfate, and the solvent was evaporated under reduced pressure from the solution to give 432 mg of 4-butyl-3-cyclohexenylamine.

(3) To a mixture of the above product (2) (430 mg), 4-hydroxy-3-methoxyphenyacetic acid (486 mg), and benzotriazol-1-yloxy-tris(pyrrolidino)phosphonium hexafluorophosphate (1.53 g) in dichloromethane (30 ml) under ice-cooling was added triethylamine (0.41 ml). The reaction mixture was stirred at room temperature for 1 hour, and then washed with saturated aqueous ammonium chloride and subsequently brine. The organic layer was dried over sodium sulfate, and the solvent was removed in vacuo. The residue was purified by a silica gel chromatography (eluent: chloroform) to give 670 mg of the desired compound.

$^1$H-NMR (CDCl$_3$, δ): 0.88 (3H, t), 1.00-1.40 (4H, m), 1.80-2.15 (7H, m), 2.22-2.35 (1H, m), 3.48 (2H, s), 3.88 (3H, s), 4.00-4.10 (1H, m), 5.19-5.26 (1H, m), 5.39 (1H, d), 5.57 (1H, s), 6.71 (1H, dd), 6.75 (1H, d), 6.88 (1H, d).

Example 2

Preparation of N-(4-butylcyclohexyl)-2-(4-hydroxy-3-methoxyphenyl)acetamide

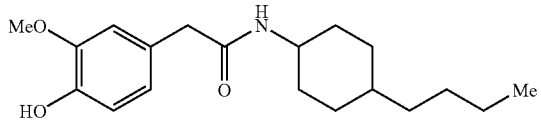

The compound (180 mg) of Example 1 was dissolved in ethanol (7 ml), 10% palladium/carbon (50 mg) was added to the solution, and the mixture was hydrogenated at 25° C. The catalyst was removed by filtration from the reaction mixture, and the solvent was evaporated under reduced pressure. The residue was purified by a silica gel chromatography (eluent: chloroform) to give 146 mg of the desired compound (cis:trans=1:4).

$^1$H-NMR (CDCl$_3$, δ): 0.84-1.05 (6H, m), 1.12-1.40 (6H, m), 1.48-1.59 (2H, m), 1.61-1.77 (2H, m), 1.83-1.95 (2H, m), 3.46 (2H×⅘, s), 3.49 (2H×⅕, s), 3.62-3.74 (1H×⅘, m), 3.88 (3H, s), 3.92-4.04 (1H×⅕, m), 5.18 (1H×⅘, d), 5.44-5.54 (1H×⅕, m), 5.58 (1H, s), 6.71 (1H, dd), 6.75 (1H, d), 6.88 (1H, d).

Example 3

Preparation of 2-(4-hydroxy-3-methoxyphenyl)-N-(4-pentyl-cyclohexyl)acetamide

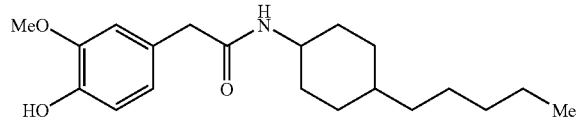

(1) To a mixture of 4-pentylcyclohexanol (3.03 g), triethylamine (3.73 ml), and dichloromethane (60 ml), a solution of methanesulfonyl chloride (2.45 g) in dichloromethane (15 ml) was added under ice-cooling over 10 minutes, and the mixture was stirred at room temperature for 3 hours. Consequently, water was added to the reaction mixture, and the mixture was extracted with chloroform. The organic layer was washed with brine, dried over sodium sulfate, and then the solvent was removed in vacuo. To the residue, sodium azide (2.81 g) and N,N-dimethylformamide (50 ml) were added, and then the mixture was stirred with heating at 120° C. for 3 hours. Water was added to the reaction mixture, and the mixture was extracted with toluene. The organic layer was washed with brine and dried over sodium sulfate, and then the solution was purified by silica gel chromatography (eluent: hexane/ethyl acetate=5/1) to give 3.19 g of 4-pentylcyclohexyl azide.

(2) The above compound (1) (3.10 g) was dissolved in ethanol (30 ml), 10% palladium/carbon (300 mg) was added to the solution, and the mixture was hydrogenated at 25° C. The catalyst was removed by filtration from the reaction mixture, and the solvent was evaporated under reduced pressure. The residual solvent in the residue was removed by azeotropic distillation with toluene to give 2.55 g of 4-pentylcyclohexylamine.

(3) To a mixture of the above product (2) (500 mg), 4-hydroxy-3-methoxyphenylacetic acid (430 mg), and benzotriazol-1-yloxy-tris(pyrrolidino)phosphonium hexafluorophosphate (1.22 g) in dichloromethane (35 ml) under ice-cooling was added triethylamine (0.33 ml), and the mixture was stirred at room temperature for 2 hours. Consequently, the reaction mixture was washed with saturated aqueous ammonium chloride and then brine. The organic layer was dried over sodium sulfate, and the solvent was removed in vacuo. The residue was purified by a silica gel chromatography (eluent:chloroform) to give 530 mg of the desired compound (cis:trans=2:1).
$^1$H-NMR (CDCl$_3$, δ): 0.84-1.00 (6H, m), 1.12-1.60 (10H, m), 1.61-1.77 (2H, m), 1.83-1.95 (2H, m), 3.46 (2H×⅓, s), 3.49 (2H×⅔, s), 3.63-3.74 (1H×⅓, m), 3.89 (3H, s), 3.91-4.03 (1H×⅔, m), 5.18 (1H×⅓, d), 5.45-5.54 (1H×⅔, m), 5.59 (1H, s), 6.72 (1H, dd), 6.76 (1H, d), 6.91 (1H, d).

Example 4-8

Instead of 4-pentylcyclohexanol in Example 3, various 4-substituted cyclohexanols are treated in a similar manner to Example 3 to give the compounds as listed in Table 1.

Example 9

Preparation of N-(4,4-dipropylcyclohexyl)-2-(4-hydroxy-3-methoxyphenyl)acetamide

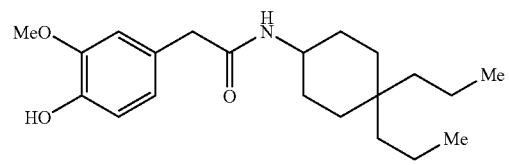

4,4-Dipropyl-2-cyclohexenone (2.0 g) was dissolved in ethanol (20 ml), 10% palladium/carbon (200 mg) was added to the solution, and the mixture was hydrogenated at 25° C. The catalyst was removed by filtration from the reaction mixture, and the solvent was removed in vacuo to give 4,4-

TABLE 1

| | Structure | $^1$H-NMR (CDCl$_3$, δ) |
|---|---|---|
| Example 4 | MeO, HO-phenyl-CH$_2$-C(O)-NH-cyclohexyl-C(Me)$_2$-Me | 0.67-0.89 (11H, m), 0.91-1.53 (5H, m), 1.61-1.79 (2H, m), 1.88-2.19 (2H, m), 3.47 (2H × 1/3, s), 3.51 (2H × 2/3, s), 3.64-3.74 (1H × 1/3, m), 3.89 (3H, s), 3.97-4.08 (1H × 2/3, m), 5.14-5.21 (1H × 1/3, m), 5.46-5.56 (1H × 2/3, m), 5.59 (1H, s), 6.72 (1H, dd), 6.76 (1H, d), 6.91 (1H, d). |
| Example 5 | MeO, HO-phenyl-CH$_2$-C(O)-NH-cyclohexyl-cyclohexyl | 0.84-1.30 (12H, m), 1.41-1.97 (8H, m), 3.46 (2H × 1/2, s), 3.50 (2H × 1/2, s), 3.62-3.73 (1H × 1/2, m), 3.89 (3H, s), 3.92-4.05 (1H × 1/2, m), 5.18 (1H × 1/2, d), 5.46-5.56 (1H × 1/2, m), 5.59 (1H, s), 6.72 (1H, dd), 6.76 (1H, d), 6.91 (1H, d). |
| Example 6 | MeO, HO-phenyl-CH$_2$-C(O)-NH-cyclohexyl-phenyl | 1.12-1.40 (2H, m), 1.51-1.95 (6H, m), 3.54 (2H, s), 3.63-3.74 (1H, m), 3.89 (3H, s), 4.10-4.20 (1H, m), 5.45-5.60 (1H, m), 5.64 (1H, s), 6.72 (1H, dd), 6.76 (1H, d), 6.91 (1H, d) 7.15-7.32 (5H, m). |
| Example 7 | MeO, HO-phenyl-CH$_2$-C(O)-NH-cyclohexyl-(CH$_2$)$_3$-Me | 0.84-1.00 (6H, m), 1.12-1.60 (8H, m), 1.61-1.77 (2H, m), 1.83-1.95 (2H, m), 3.49 (2H, s), 3.89 (3H, s), 3.92-4.04 (1H, m), 5.44-5.54 (1H, m), 5.59 (1H, s), 6.72 (1H, dd), 6.76 (1H, d), 6.91 (1H, d). |
| Example 8 | MeO, HO-phenyl-CH$_2$-C(O)-NH-cyclohexyl-(CH$_2$)$_4$-Me | 0.84-1.00 (6H, m), 1.12-1.60 (10H, m), 1.61-1.77 (2H, m), 1.83-1.95 (2H, m), 3.49 (2H, s), 3.89 (3H, s), 3.91-4.03 (1H, m), 5.45-5.54 (1H, m), 5.59 (1H, s), 6.72 (1H, dd), 6.76 (1H, d), 6.91 (1H, d). | dipropylcyclohexanone. The product was dissolved in methanol/water=1/1 (20 ml). Hydroxylamine hydrochloride (1.55 g) and sodium acetate (1.83 g) were added to the solution, and the mixture was stirred with heating at 50° C. for 12 hours. After removing the methanol in vacuo, the residue was extracted with ethyl acetate. The organic layer was washed with water, and the solvent was removed in vacuo. The residue was purified by a silica gel chromatography (eluent: gradient from 100% hexane/0% ethyl acetate to 0% hexane/100% ethyl acetate) to give 1.4 g of 4,4-dipropylcyclohexanone oxime. A solution of the product in tetrahydrofuran (10 ml) was added dropwise to a solution of lithium aluminium hydride (420 mg) in tetrahydrofuran (10 ml) under ice-cooling, and the mixture was stirred. After 3 hours, the reaction was quenched by adding water (0.42 ml), 15% aqueous sodium hydroxide (0.42 ml), and then water (1.26 ml) dropwise to the reaction mixture. The precipitate was filtered off and then the solvent was removed in vacuo. The residue was dissolved in 2 mol/l aqueous hydrochloric acid, washed with diethyl ether, basified with 2 mol/l aqueous sodium hydroxide, and then extracted with chloroform. The organic layer was concentrated under reduced pressure to give 165 mg of 4,4-dipropylcyclohexylamine. The product (100 mg) was dissolved in ethyl acetate (5 ml), and 4-hydroxy-3-methoxyphenylacetic acid (100 mg) and 1-ethyl-3-(3-dimethylaminopropyl)carbodiimide hydrochloride (110 mg) were added to the solution, and the mixture was stirred at 25° C. for 12 hours. The reaction mixture was washed with water and then the solvent was removed in vacuo. The residue was purified by a silica gel chromatography (eluent: gradient from 100% hexane/0% ethyl acetate to 0% hexane/100% ethyl acetate) to give 120 mg of the desired compound.

$^1$H-NMR (CDCl$_3$, δ): 0.80-0.95 (6H, m), 1.05-1.25 (12H, m), 1.30-1.45 (2H, m), 1.57-1.73 (2H, m), 3.47 (2H, s), 3.63-3.78 (1H, m), 3.88 (3H, s), 5.22-5.40 (1H, m), 5.73 (1H, s), 6.72 (1H, d), 6.76 (1H, s), 6.90 (1H, d).

Example 10

Preparation of N-(4-butylidenecyclohexyl)-2-(4-hydroxy-3-methoxyphenyl)acetamide

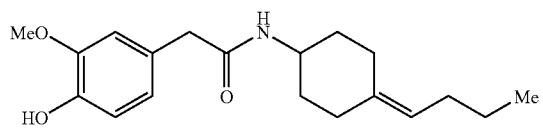

(1) To a mixture of potassium t-butoxide (2.05 g) and anhydrous N,N-dimethylformamide (60 ml) was added butyltriphenylphosphonium bromide (7.30 g) at room temperature. The mixture was stirred for 15 minutes and then a solution of t-butyl 4-oxocyclohexylcarbamate (1.30 g) in N,N-dimethylformamide (10 ml) was added to the mixture. The reaction mixture was stirred at room temperature overnight and then saturated aqueous ammonium chloride was added to the mixture. The mixture was extracted with toluene, and the organic layer was washed with brine, dried over sodium sulfate, and then the solvent was removed in vacuo. After diethyl ether was added to the residue, the precipitate was filtered off and then the filtrate was concentrated under reduced pressure. The residue was purified by a silica gel chromatography (eluent: gradient from 100% hexane/0% ethyl acetate to 0% hexane/100% ethyl acetate) to give 1.40 g of t-butyl (4-butylidenecyclohexyl)carbamate.

(2) To a solution of the above product (1) (711 mg) in ethyl acetate (10 ml) was added 4 mol/l hydrogen chloride solution (in ethyl acetate, 10 ml), and the mixture was stirred for 1 hour. Hexane (20 ml) was added to the reaction mixture, and the precipitated crystal was collected by filtration to give 470 mg of 4-butylidenecyclohexylamine hydrochloride.

(3) To a mixture of the above product (2) (470 mg), 4-hydroxy-3-methoxyphenyacetic acid (410 mg), and benzotriazol-1-yloxy-tris(pyrrolidino)phosphonium hexafluorophosphate (1.17 g) in dichloromethane (35 ml) under ice-cooling was added triethylamine (0.94 ml). The reaction mixture was stirred at room temperature for 1 hour, and then washed with saturated aqueous ammonium chloride and then brine. The organic layer was dried over sodium sulfate, and then the solvent was removed in vacuo. The residue was purified by a silica gel chromatography (eluent:chloroform) to give 590 mg of the desired compound.

$^1$H-NMR (CDCl$_3$, δ): 0.86 (3H, t), 1.00-1.40 (4H, m), 1.80-2.15 (7H, m), 2.32-2.47 (1H, m), 3.47 (2H, s), 3.85-3.90 (1H, m), 3.88 (3H, s), 5.10 (1H, t), 5.24 (1H, d), 5.57 (1H, s), 6.71 (1H, dd), 6.75 (1H, d), 6.88 (1H, d).

Example 11-13

Instead of butyltriphenylphosphonium bromide of Example 10, various phosphonium halides or phosphonic acids diester are treated in a similar manner of Example 10 to give the compounds as listed in Table 2.

TABLE 2

| | Structure | $^1$H-NMR (CDCl$_3$, δ) |
|---|---|---|
| Example 11 | 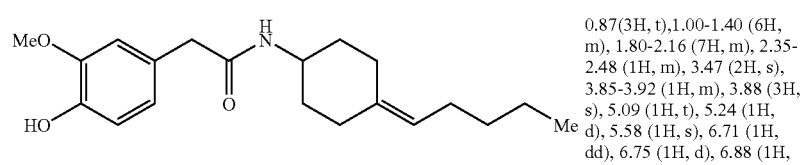 | 0.87(3H, t),1.00-1.40 (6H, m), 1.80-2.16 (7H, m), 2.35-2.48 (1H, m), 3.47 (2H, s), 3.85-3.92 (1H, m), 3.88 (3H, s), 5.09 (1H, t), 5.24 (1H, d), 5.58 (1H, s), 6.71 (1H, dd), 6.75 (1H, d), 6.88 (1H, d). |

TABLE 2-continued

| | Structure | $^1$H-NMR (CDCl$_3$, δ) |
|---|---|---|
| Example 12 | MeO, HO— phenyl-CH$_2$-C(O)-NH-cyclohexylidene-CH$_2$-CH(Me)$_2$ | 0.85 (6H, d), 1.00-1.60 (4H, m), 1.80-2.15 (6H, m), 2.34-2.47 (1H, m), 3.48 (2H, s), 3.85-3.92 (1H, m), 3.88 (3H, s), 5.10 (1H, t), 5.24 (1H, d), 5.57 (1H, s), 6.71 (1H, dd), 6.75 (1H, d), 6.88 (1H, d). |
| Example 13 | MeO, HO— phenyl-CH$_2$-C(O)-NH-cyclohexylidene-CH$_2$-CH=CH$_2$ | 1.00-1.22 (2H, m), 1.82-2.15 (9H, m), 2.32-2.47 (1H, m), 3.48 (2H, s), 3.84-3.92 (1H, m), 3.88 (3H, s), 4.91-5.03 (2H, m), 5.10 (1H, t), 5.24 (1H, d), 5.58 (1H, s), 5.70-5.84 (1H, m), 6.71 (1H, dd), 6.75 (1H, d), 6.88 (1H, d). |

Example 14

Preparation of 2-(4-hydroxy-3-methoxyphenyl)-N-{trans-4-[(Z)-3-methyl-1-butenyl]cyclohexyl}acetamide

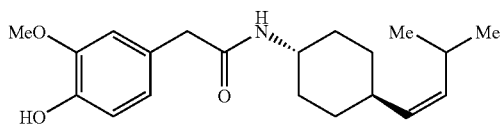

(1) To a mixture of potassium t-butoxide (379 mg) and anhydrous N,N-dimethylformamide (20 ml) was added isobutyltriphenylphosphonium bromide (1.35 g) at room temperature. The mixture was stirred for 10 minutes, and then a solution of t-butyl trans-4-formylcyclohexyl-carbamate (700 mg) in N,N-dimethylformamide (3 ml) was added to the mixture. After the reaction mixture was stirred overnight, saturated aqueous ammonium chloride was added thereto. The mixture was extracted with toluene, and the organic layer was washed with brine, dried over sodium sulfate, and then the solvent was removed in vacuo. After diethyl ether was added to the residue, the precipitate was filtered off and then the filtrate was concentrated under reduced pressure. The residue was purified by a silica gel chromatography (eluent: gradient from 100% hexane/0% ethyl acetate to 0% hexane/100% ethyl acetate) to give 380 mg of t-butyl trans-{4-[(Z)-3-methyl-1-butenyl]cyclohexyl}-carbamate.

(2) To a solution of the above product (1) (370 mg) in ethyl acetate (5 ml) was added 4 mol/l hydrogen chloride solution (in ethyl acetate, 5 ml). The mixture was stirred for 1 hour, and then hexane (10 ml) was added to the mixture. The precipitated crystal was removed by filtration to give 230 mg of trans-4-[(Z)-3-methyl-1-butenyl]cyclohexylamine hydrochloride.

(3) To a mixture of the above product (2) (230 mg), 4-hydroxy-3-methoxyphenyacetic acid (202 mg) and benzotriazol-1-yloxy-tris(pyrrolidino)phosphonium hexafluorophosphate (634 mg) in dichloromethane (25 ml) under ice-cooling was added triethylamine (0.43 ml). The reaction mixture was stirred at room temperature for 1 hour, and then washed with saturated aqueous ammonium chloride and then brine. The organic layer was dried over sodium sulfate, and then the solvent was removed in vacuo. The residue was purified by a silica gel chromatography (eluent: chloroform) to give 345 mg of the desired compound.

$^1$H-NMR (CDCl$_3$, δ): 0.92 (6H, d), 0.99-1.26 (4H, m), 1.49-1.65 (2H, m), 1.85-1.95 (2H, m), 2.10-2.21 (1H, m), 2.46-2.58 (1H, m), 3.47 (2H, s), 3.63-3.77 (1H, m), 3.88 (3H, s), 4.99 (1H, dd), 5.10 (1H, dd), 5.18 (1H, d), 5.58 (1H, s), 6.71 (1H, dd), 6.75 (1H, d), 6.88 (1H, d).

Examples 15-25

Instead of isobutyltriphenylphosphonium bromide of Example 14, various phosphonium halides or phosphonic acid diesters are treated in a similar manner of Example 14 to give the compounds listed in Table 3.

TABLE 3

| | Structure | $^1$H-NMR (CDCl$_3$, δ) |
|---|---|---|
| Example 15 | MeO, HO— phenyl-CH$_2$-C(O)-NH-cyclohexyl-CH=CH-CH$_2$-CH(Me)$_2$ | 0.87 (6H, d), 0.98-1.26 (4H, m), 1.49-1.64 (4H, m), 1.82-1.96 (3H, m), 2.11-2.22 (1H, m), 3.47 (2H, s), 3.64-3.78 (1H, m), 3.88 (3H, s), 5.15 (1H, dd), 5.18 (1H, d), 5.28 (1H, dt), 5.58 (1H, s), 6.71 (1H, dd), 6.75 (1H, d), 6.88 (1H, d). |

TABLE 3-continued

| | Structure | $^1$H-NMR (CDCl$_3$, δ) |
|---|---|---|
| Example 16 | 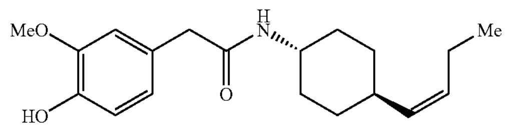 | 0.94 (3H, t), 1.00-1.27 (4H, m), 1.52-1.64 (2H, m), 1.85-2.05 (4H, m), 2.12-2.22 (1H, m), 3.47 (2H, s), 3.63-3.77 (1H, m), 3.89 (3H, s), 5.13 (1H, dd), 5.17 (1H, d), 5.28 (1H, dt), 5.58 (1H, s), 6.71 (1H, dd), 6.75 (1H, d), 6.88 (1H, d). |
| Example 17 | 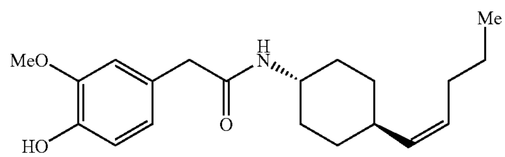 | 0.87 (3H, t), 0.98-1.38 (6H, m), 1.51-1.64 (2H, m), 1.82-2.02 (4H, m), 2.10-2.23 (1H, m), 3.47 (2H, s), 3.65-3.77 (1H, m), 3.89 (3H, s), 5.16 (1H, dd), 5.18 (1H, d), 5.27 (1H, dt), 5.59 (1H, s), 6.72 (1H, dd), 6.75 (1H, d), 6.88 (1H, d). |
| Example 18 | 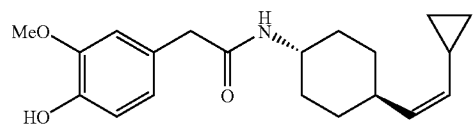 | 0.27-0.31 (2H, m), 0.62-0.75 (2H, m), 0.90-1.92 (9H, m), 2.20-2.41 (1H, m), 3.47 (2H, s), 3.63-3.77 (1H, m), 3.88 (3H, s), 4.64 (1H, dd), 5.08 (1H, dd), 5.12-5.25 (1H, m), 5.59 (1H, s), 6.71 (1H, dd), 6.75 (1H, d), 6.88 (1H, d). |
| Example 19 | 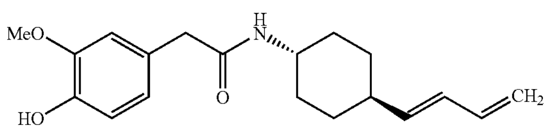 | 0.98-1.36 (4H, m), 1.62-2.01 (5H, m), 3.47 (2H, s), 3.63-3.78 (1H, m), 3.89 (3H, s), 4.96 (1H, d), 5.09 (1H, d), 5.16 (1H, d), 5.58 (1H, s), 5.99 (1H, dd), 6.00 (1H, dd), 6.27 (1H, ddd), 6.71 (1H, dd), 6.75 (1H, d), 6.88 (1H, d). |
| Example 20 | 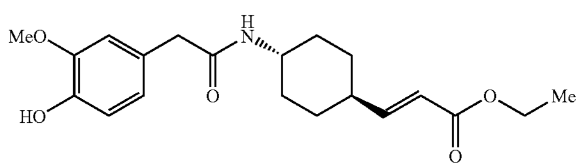 | 1.00-1.37 (4H, m), 1.28 (3H, t), 1.52-2.10 (5H, m), 3.47 (2H, s), 3.65-3.79 (1H, m), 3.89 (3H, s), 4.08-4.23 (1H, m), 4.17 (1H, q), 5.20 (1H, d), 5.60 (1H, s), 5.75 (1H, d), 6.71 (1H, dd), 6.75 (1H, d), 6.85 (1H, dd), 6.88 (1H, d). |
| Example 21 | 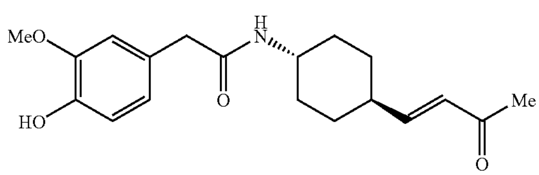 | 1.00-1.38 (4H, m), 1.55-2.10 (5H, m), 2.23 (3H, s), 3.48 (2H, s), 3.65-3.79 (1H, m), 3.89 (3H, s), 5.21 (1H, d), 5.61 (1H, s), 6.01 (1H, d), 6.67 (1H, dd), 6.71 (1H, dd), 6.75 (1H, d), 6.88 (1H, d). |
| Example 22 | 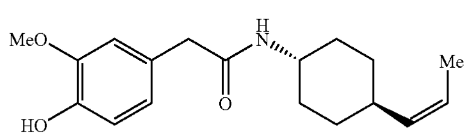 | 0.99-1.27 (4H, m), 1.51-1.65 (2H, m), 1.58 (3H, d), 1.82-1.98 (2H, m), 2.13-2.23 (1H, m), 3.47 (2H, s), 3.64-3.77 (1H, m), 3.89 (3H, s), 5.16 (1H, dd), 5.19 (1H, d), 5.36 (1H, dq), 5.58 (1H, s), 6.72 (1H, dd), 6.76 (1H, d), 6.89 (1H, d). |
| Example 23 | 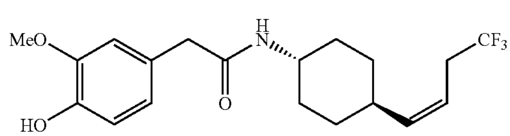 | 0.98-1.30 (4H, m), 1.53-1.68 (2H, m), 1.88-2.18 (3H, m), 2.70-2.89 (2H, m), 3.48 (2H, s), 3.63-3.77 (1H, m), 3.89 (3H, s), 5.17 (1H, dd), 5.30 (1H, dt), 5.50 (1H, dd), 5.58 (1H, s), 6.72 (1H, dd), 6.75 (1H, d), 6.89 (1H, d). |

TABLE 3-continued

| | Structure | $^1$H-NMR (CDCl$_3$, δ) |
|---|---|---|
| Example 24 | MeO, HO-phenyl-CH$_2$-C(O)-NH-cyclohexyl-CH=C(Me)Me | 0.92-1.27 (4H, m), 1.52-1.68 (2H, m), 1.57 (6H, s), 1.86-2.10 (3H, m), 3.47 (2H, s), 3.63-3.76 (1H, m), 3.89 (3H, s), 4.89 (1H, d), 5.18 (1H, d), 5.59 (1H, s), 6.72 (1H, dd), 6.76 (1H, d), 6.88 (1H, d). |
| Example 25 | MeO, HO-phenyl-CH$_2$-C(O)-NH-cyclohexyl-CH=cyclopentyl | 0.92-1.27 (4H, m), 1.52-1.68 (8H, m), 1.80-2.20 (5H, m), 3.47 (2H, s), 3.63-3.77 (1H, m), 3.89 (3H, s), 5.03 (1H, d), 5.17 (1H, d), 5.59 (1H, s), 6.72 (1H, dd), 6.76 (1H, d), 6.88 (1H, d). |

Example 26

Preparation of 2-(4-hydroxy-3-methoxyphenyl)-N-[trans-4-(3-methylbutyl)cyclohexyl]acetamide

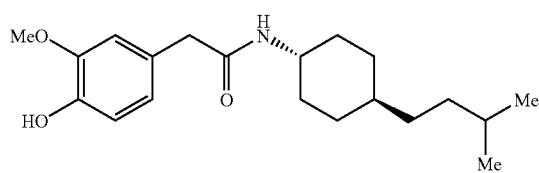

The compound (200 mg) of Example 14 was dissolved in ethanol (10 ml), 10% palladium/carbon (50 mg) was added to the mixture, and the mixture was hydrogenated at 25° C. The catalyst was removed by filtration from the reaction mixture, and the solvent was evaporated under reduced pressure. The residue was purified by a silica gel chromatography (eluent: chloroform) to give 145 mg of the desired compound.

$^1$H-NMR (CDCl$_3$, δ): 0.85 (6H, d), 0.90-1.20 (6H, m), 1.40-1.57 (4H, m), 1.59-1.76 (2H, m), 1.80-1.99 (2H, m), 3.46 (2H, s), 3.62-3.75 (1H, m), 3.88 (3H, s), 5.18 (1H, d), 5.59 (1H, s), 6.71 (1H, dd), 6.75 (1H, d), 6.88 (1H, d).

Example 27-34

Instead of the compound of Example 14 in Example 26, the compounds of Examples 15, 16, 20, 17, 22, 18, 24, and 25 are treated in a similar manner of Example 26 to give the compounds listed in Table 4.

TABLE 4

| | Structure | $^1$H-NMR (CDCl$_3$, δ) |
|---|---|---|
| Example 27 | MeO, HO-phenyl-CH$_2$-C(O)-NH-cyclohexyl-(CH$_2$)$_3$-CH(Me)Me | 0.85 (6H, d), 0.90-1.35 (8H, m), 1.40-1.57 (4H, m), 1.59-1.76 (2H, m), 1.80-1.98 (2H, m), 3.46 (2H, s), 3.63-3.75 (1H, m), 3.88 (3H, s), 5.18 (1H, d), 5.60 (1H, s), 6.71 (1H, dd), 6.75 (1H, d), 6.88 (1H, d). |
| Example 28 | MeO, HO-phenyl-CH$_2$-C(O)-NH-cyclohexyl-(CH$_2$)$_2$-Me | 0.84-1.05 (6H, m), 1.12-1.40 (6H, m), 1.48-1.59 (2H, m), 1.61-1.77 (2H, m), 1.83-1.95 (2H, m), 3.46 (2H, s), 3.62-3.74 (1H, m), 3.88 (3H, s), 5.18 (1H, d), 5.58 (1H, s), 6.71 (1H, dd), 6.75 (1H, d), 6.88 (1H, d). |
| Example 29 | MeO, HO-phenyl-CH$_2$-C(O)-NH-cyclohexyl-CH$_2$CH$_2$C(O)OCH$_2$Me | 0.84-1.29 (6H, m), 1.42-1.59 (4H, m), 1.69-1.77 (2H, m), 1.80-1.95 (2H, m), 2.27 (2H, t), 3.46 (2H, s), 3.63-3.75 (1H, m), 3.88 (3H, s), 4.17 (2H, q), 5.17 (1H, d), 5.59 (1H, s), 6.70 (1H, dd), 6.75 (1H, d), 6.88 (1H, d). |

TABLE 4-continued

| | Structure | $^1$H-NMR (CDCl$_3$, δ) |
|---|---|---|
| Example 30 | MeO, HO-phenyl-CH$_2$-C(O)-NH-cyclohexyl-(CH$_2$)$_4$-Me | 0.84-1.05 (6H, m), 1.12-1.42 (8H, m), 1.47-1.59 (2H, m), 1.61-1.76 (2H, m), 1.84-1.93 (2H, m), 3.46 (2H, s), 3.63-3.74 (1H, m), 3.88 (3H, s), 5.18 (1H, d), 5.58 (1H, s), 6.71 (1H, dd), 6.75 (1H, d), 6.88 (1H, d). |
| Example 31 | MeO, HO-phenyl-CH$_2$-C(O)-NH-cyclohexyl-CH$_2$-Me | 0.85 (3H, t), 0.92-1.53 (9H, m), 1.61-1.76 (2H, m), 1.83-1.94 (2H, m), 3.46 (2H, s), 3.62-3.74 (1H, m), 3.88 (3H, s), 5.17 (1H, d), 5.58 (1H, s), 6.71 (1H, dd), 6.75 (1H, d), 6.88 (1H, d). |
| Example 32 | MeO, HO-phenyl-CH$_2$-C(O)-NH-cyclohexyl-CH$_2$-cyclopropyl | −0.02-0.07 (2H, m), 0.35-0.45 (2H, m), 0.58-0.65 (1H, m), 0.80-1.36 (9H, m), 1.62-1.95 (4H, m), 3.47 (2H, s), 3.62-3.74 (1H, m), 3.89 (3H, s), 5.19 (1H, d), 5.60 (1H, s), 6.71 (1H, dd), 6.75 (1H, d), 6.88 (1H, d). |
| Example 33 | MeO, HO-phenyl-CH$_2$-C(O)-NH-cyclohexyl-CH$_2$-CH(Me)-Me | 0.82 (6H, d), 0.90-1.31 (6H, m), 1.51-1.96 (6H, m), 3.47 (2H, s), 3.62-3.74 (1H, m), 3.89 (3H, s), 5.18 (1H, d), 5.60 (1H, brs), 6.71 (1H, dd), 6.75 (1H, d), 6.88 (1H, d). |
| Example 34 | MeO, HO-phenyl-CH$_2$-C(O)-NH-cyclohexyl-CH$_2$-cyclopentyl | 0.91-1.22 (6H, m), 1.42-1.95 (14H, m), 3.46 (2H, s), 3.62-3.74 (1H, m), 3.88 (3H, s), 5.19 (1H, d), 5.59 (1H, s), 6.71 (1H, dd), 6.75 (1H, d), 6.88 (1H, d). |

Example 35

Preparation of N-(trans-4-butoxycyclohexyl)-2-(4-hydroxy-3-methoxyphenyl)acetamide

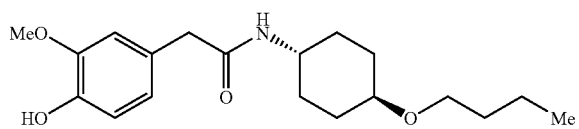

(1) To a suspension of 60% sodium hydride (168 mg) and anhydrous N,N-dimethylformamide (25 ml) under ice-cooling was added t-butyl trans-4-hydroxycyclohexyl-carbamate (600 mg). The mixture was stirred for 5 minutes, then butyl iodide (821 mg) was added thereto and the mixture was stirred for 3 hours under heating at 80° C. Saturated aqueous ammonium chloride was added to the reaction mixture. The mixture was extracted with toluene, and the organic layer was washed with brine, dried over sodium sulfate, and then the solvent was removed in vacuo. The residue was purified by a silica gel chromatography (eluent: gradient from 100% hexane/0% ethyl acetate to 0% hexane/100% ethyl acetate) to give 630 mg of t-butyl (trans-4-butoxycyclohexyl)carbamate.

(2) To a solution of the above product (1) (600 mg) in ethyl acetate (9 ml) was added 4 mol/l hydrogen chloride solution (in ethyl acetate, 9 ml). The mixture was stirred for 1 hour, and then hexane (18 ml) was added thereto. The precipitated crystal was collected by filtration to give 300 mg of trans-4-butoxycyclohexylamine hydrochloride.

(3) To a mixture of the above product (2) (300 mg), 4-hydroxy-3-methoxyphenyacetic acid (322 mg), and benzotriazol-1-yloxy-tris(pyrrolidino)phosphonium hexafluorophosphate (920 mg) in dichloromethane (35 ml) under ice-cooling was added triethylamine (0.74 ml). The reaction mixture was stirred at room temperature for 1 hour, and then washed with saturated aqueous ammonium chloride and then brine. The organic layer was dried over sodium sulfate, and then the solvent was removed in vacuo. The residue was purified by a silica gel chromatography (eluent: chloroform) to give 110 mg of the desired compound.

$^1$H-NMR (CDCl$_3$, δ): 0.90 (3H, t), 1.00-1.53 (8H, m), 1.88-2.02 (4H, m), 3.06-3.17 (1H, m), 3.40 (2H, t), 3.46 (2H, s), 3.64-3.74 (1H, m), 3.88 (3H, s), 5.17 (1H, d), 5.58 (1H, s), 6.71 (1H, dd), 6.75 (1H, d), 6.88 (1H, d).

Example 36-39

Instead of butyl iodide of Example 35, various alkyl halides are treated in a similar manner of Example 35 to give the compounds listed in Table 5.

TABLE 5

| | Structure | $^1$HNMR (CDCl$_3$, δ) |
|---|---|---|
| Example 36 | 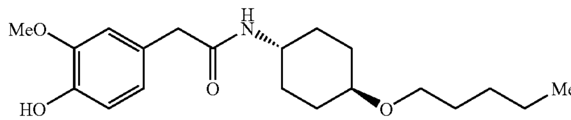 | 0.88 (3H, t), 1.00-1.53 (10H, m), 1.88-2.02 (4H, m), 3.06-3.17 (1H, m), 3.39 (2H, t), 3.47 (2H, s), 3.64-3.74 (1H, m), 3.88 (3H, s), 5.17 (1H, d), 5.60 (1H, s), 6.71 (1H, dd), 6.75 (1H, d), 6.88 (1H, d). |
| Example 37 | 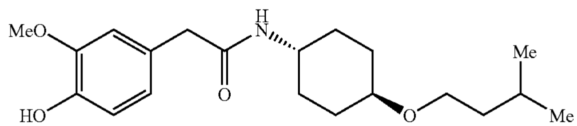 | 0.88 (6H, d), 0.99-1.12 (2H, m), 1.21-1.69 (5H, m), 1.88-2.03 (4H, m), 3.06-3.16 (1H, m), 3.42 (2H, t), 3.46 (2H, s), 365-3.76 (1H, m), 3.88 (3H, s), 5.17 (1H, d), 5.58 (1H, s), 6.71 (1H, dd), 6.75 (1H, d), 6.88 (1H, d). |
| Example 38 | 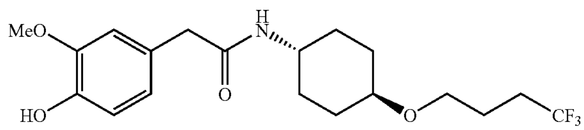 | 0.98-1.46 (6H, m), 1.72-2.22 (6H, m), 3.12-3.20 (1H, m), 3.45 (2H, t), 3.47 (2H, s), 3.65-3.76 (1H, m), 3.89 (3H, s), 5.18 (1H, d), 5.58 (1H, s), 6.71 (1H, dd), 6.75 (1H, d), 6.88 (1H, d). |
| Example 39 | 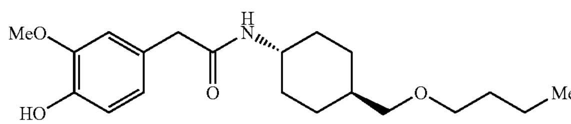 | 0.90 (3H, t), 0.91-1.49 (9H, m), 1.80-2.01 (4H, m), 3.17 (2H, d), 3.37 (2H, t), 3.46 (2H, s), 3.61-3.77 (1H, m), 3.88 (3H, s), 5.19 (1H, d), 5.63 (1H, s), 6.71 (1H, dd), 6.75 (1H, d), 6.88 (1H, d). |

Example 40

Preparation of 2-(4-hydroxy-3-methoxyphenyl)-N-[trans-4-(4-methylphenylcarbonyloxy)cyclohexyl]acetamide

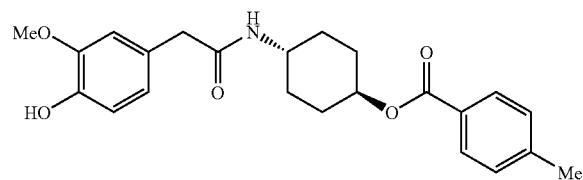

(1) To a mixture of t-butyl trans-4-hydroxycyclohexylcarbamate (1.00 g) and pyridine (773 mg) in dichloromethane (40 ml) under ice-cooling was added a solution of 4-methylbenzoylchloride (754 mg) in dichloromethane (10 ml) over 10 minutes. The mixture was stirred overnight at room temperature, and then saturated aqueous ammonium chloride was added thereto. The mixture was extracted with chloroform, and the organic layer was washed with brine, dried over sodium sulfate, and then the solvent was removed in vacuo. The residue was purified by a silica gel chromatography (eluent: gradient from 100% hexane/0% ethyl acetate to 0% hexane/100% ethyl acetate) to give 1.30 g of t-butyl trans-[4-(4-methylphenylcarbonyloxy)cyclohexyl]-carbamate.

(2) To a solution of the above product (1) (670 mg) in dichloromethane (30 ml) under ice-cooling was added trifluoroacetic acid (3 ml). The reaction mixture was stirred at room temperature for 15 hours, and then saturated aqueous ammonium chloride was added thereto. The mixture was extracted with chloroform, and the organic layer was washed with brine, dried over sodium sulfate, and the solvent was removed in vacuo to give 600 mg of trans-4-(4-methylphenylcarbonyloxy)cyclohexylamine trifluoroacetic acid.

(3) To a mixture of the above product (2) (600 mg), 4-hydroxy-3-methoxyphenyacetic acid (293 mg), and benzotriazol-1-yloxy-tris(pyrrolidino)phosphonium hexafluorophosphate (837 mg) in dichloromethane (60 ml) under ice-cooling was added triethylamine (0.56 ml). The reaction mixture was stirred at room temperature for 1 hour, and then washed with saturated aqueous ammonium chloride and then brine. The organic layer was dried over sodium sulfate, and then the solvent was removed in vacuo. The residue was purified by a silica gel chromatography (eluent: chloroform) to give 285 mg of the desired compound.

$^1$H-NMR (CDCl$_3$, δ): 1.12-1.62 (4H, m), 1.98-2.12 (4H, m), 2.40 (3H, s), 3.49 (2H, s), 3.73-3.88 (1H, m), 3.89 (3H, s), 4.82-4.90 (1H, m), 5.20 (1H, d), 5.60 (1H, s), 6.72 (1H, dd), 6.76 (1H, d), 6.89 (1H, d), 7.22 (2H, d), 7.90 (2H, d).

Example 41

Preparation of N-[trans-4-(benzylcarbonyloxy)cyclohexyl]-2-(4-hydroxy-3-methoxyphenyl)acetamide

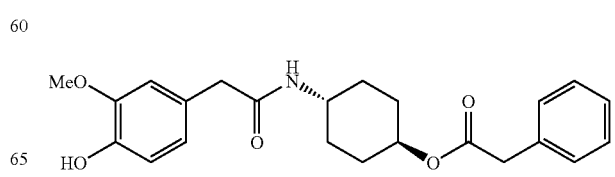

The above desired compound was prepared in a similar manner of Example 40 using 2-phenylacetyl chloride instead of 4-methylbenzoyl chloride in Example 40.

¹H-NMR (CDCl₃, δ): 1.10-1.53 (4H, m), 1.88-2.02 (4H, m), 3.46 (2H, s), 3.57 (2H, s), 3.72-3.86 (1H, m), 3.88 (3H, s), 4.60-4.74 (1H, m), 5.21 (1H, d), 5.61 (1H, s), 6.71 (1H, dd), 6.75 (1H, d), 6.88 (1H, d), 7.21-7.33 (5H, m).

Example 42

Preparation of 2-(4-hydroxy-3-methoxyphenyl)-N-[trans-4-(3-methyl-2-butenyl)cyclohexyl]acetamide

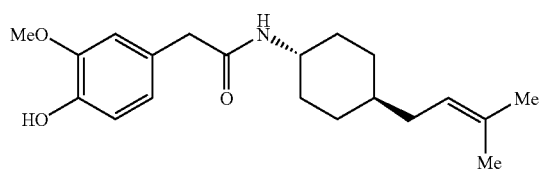

(1) To a suspension of 60% sodium hydride (366 mg) and anhydrous tetrahydrofuran (50 ml) under ice-cooling was added diethyl 2-oxopropylphosphonate (1.78 g). The mixture was stirred for 15 minutes and then a solution of t-butyl trans-4-formylcyclohexylcarbamate (1.38 g) in anhydrous tetrahydrofuran (10 ml) was added thereto under the same condition. The mixture was stirred at room temperature for 3 hours, and then saturated aqueous ammonium chloride was added to the reaction mixture. The mixture was extracted with toluene, and the organic layer was washed with brine, dried over sodium sulfate, and then the solvent was removed in vacuo. The residue was purified by a silica gel chromatography (eluent: gradient from 100% hexane/0% ethyl acetate to 0% hexane/100% ethyl acetate) to give 1.32 g of t-butyl trans-4-[(E)-3-oxo-1-butenyl]cyclohexylcarbamate.

(2) The above compound (1) (850 mg) was dissolved in ethanol (15 ml), 10% palladium/carbon (100 mg) was added to the solution, and the mixture was hydrogenated at 25° C. The catalyst was removed by filtration from the reaction mixture, and the solvent was evaporated under reduced pressure. The residual solvent was removed by azeotropic distillation with toluene to give 845 mg of t-butyl trans-4-(3-oxobutyl)cyclohexylcarbamate.

(3) Under nitrogen atmosphere, anhydrous cerium chloride (1.28 g) was added to anhydrous tetrahydrofuran (15 ml), and the mixture was stirred at room temperature for 2 hours. After cooling the suspension to −78° C., 0.98 M methyl lithium solution (in hexane, 4.81 ml) was added thereto and the mixture was stirred for 1 hour. A solution of the above product (2) (845 mg) in anhydrous tetrahydrofuran (10 ml) was added thereto over 10 minutes, and the mixture was gradually warmed to room temperature and stirred overnight. Saturated aqueous ammonium chloride was added to the reaction mixture, and then the mixture was filtrated through Celite. The filtrate was extracted with ethyl acetate, and the organic layer was washed with brine, dried over sodium sulfate, and then the solvent was removed in vacuo. The residue was purified by a silica gel chromatography (eluent: chloroform/methanol=100/1) to give 510 mg of t-butyl trans-4-(3-hydroxy-3-methylbutyl)-cyclohexylcarbamate.

(4) To a solution of the above product (3) (500 mg) in toluene (10 ml) was added p-toluenesulfonic acid monohydrate (668 mg), the mixture was stirred for 2 hours under heating at 100° C. Aqueous potassium carbonate was added to the reaction mixture, and the mixture was extracted with ethyl acetate, and the organic layer was washed with brine, dried over sodium sulfate, and then the solvent was removed in vacuo to give 300 mg of trans-4-(3-methyl-2-butenyl)cyclohexylamine.

(5) To a mixture of the above product (4) (300 mg), 4-hydroxy-3-methoxyphenyacetic acid (255 mg), and benzotriazol-1-yloxy-tris(pyrrolidino)phosphonium hexafluorophosphate (728 mg) in dichloromethane (20 ml) under ice-cooling was added triethylamine (0.39 ml). The reaction mixture was stirred at room temperature for 1 hour, and then washed with saturated aqueous ammonium chloride and then brine. The organic layer was dried over sodium sulfate, and then the solvent was removed in vacuo. The residue was purified by a silica gel chromatography (eluent: chloroform) to give 210 mg of the desired compound.

¹H-NMR (CDCl₃, δ): 0.90-1.21 (4H, m), 1.49-1.95 (7H, m), 1.68 (6H, s), 3.46 (2H, s), 3.62-3.74 (1H, m), 3.88 (3H, s), 5.08 (1H, t), 5.18 (1H, d), 5.63 (1H, s), 6.71 (1H, dd), 6.75 (1H, d), 6.88 (1H, d).

Examples 43 and 44

Preparation of (+)- and (−)-N-(4-butyl-3-cyclohexenyl)-2-(4-hydroxy-3-methoxyphenyl)acetamides

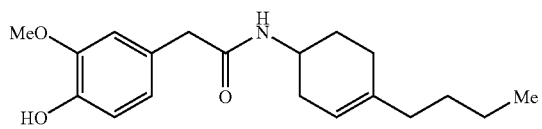

The compound of Example 1 was divided and purified with the chiral column [CHIRALPAK AD-H, DAICEL CHEMICAL INDUSTRIES, LTD.] to give both of the desired compounds (not less than 98% ee by HPLC).

The compound of Example 43: $[\alpha]_D^{22}$+11.8° (c=0.50, MeOH)

The compound of Example 44: $[\alpha]_D^{22}$−12.1° (c=0.52, MeOH)

Examples 45 and 46

Preparation of (+)- and (−)-N-(4-butylidenecyclohexyl)-2-(4-hydroxy-3-methoxyphenyl)acetamides

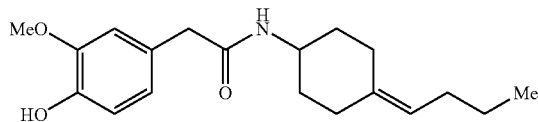

The compound of Example 10 was divided and purified with the chiral column [CHIRALCEL OJ-H, DAICEL CHEMICAL INDUSTRIES, LTD.] to give both of the desired compounds (not less than 98% ee by HPLC).

The compound of Example 45: $[\alpha]_D^{25}$+4.0° (c=0.50, MeOH)

Example 47

Preparation of 2-(4-hydroxy-3-methoxyphenyl)-N-[cis-4-(3-methyl-2-butenyl)cyclohexyl]acetamide

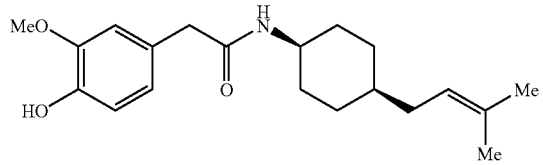

The above desired compound was prepared in a similar manner of Example 42 using t-butyl cis-4-formylcyclohexylcarbamate instead of t-butyl trans-4-formylcyclohexylcarbamate in Example 42.

$^1$H-NMR (CDCl$_3$, δ): 0.78-0.92 (4H, m), 1.25-1.60 (5H, m), 1.58 (6H, s), 1.79-1.85 (2H, m), 3.50 (2H, s), 3.90 (3H, s), 3.92-4.02 (1H, m), 5.05 (1H, t), 5.50 (1H, d), 5.59 (1H, s), 6.75 (1H, dd), 6.76 (1H, d), 6.91 (1H, d).

Example 48

Preparation of 2-(4-hydroxy-3-methoxyphenyl)-N-[cis-4-(3-methylbutyl)cyclohexyl]acetamide

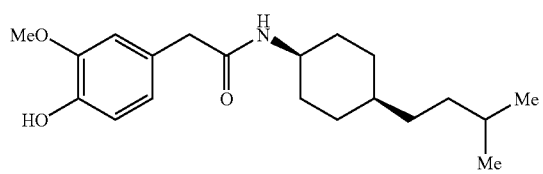

To a solution of the compound (315 mg) of Example 47 in ethanol (10 ml) was added platinum oxide (30 mg), and the mixture was hydrogenated at 25° C. The catalyst was removed by filtration from the reaction mixture, and the solvent was evaporated under reduced pressure. The residue was purified by a silica gel chromatography (eluent: gradient from 100% hexane/0% ethyl acetate to 0% hexane/100% ethyl acetate) to give 275 mg of the desired compound.

$^1$H-NMR (CDCl$_3$, δ): 0.79-0.92 (4H, m), 0.85 (6H, d), 1.05-1.30 (4H, m), 1.40-1.62 (6H, m), 3.49 (2H, s), 3.89 (3H, s), 3.91-4.02 (1H, m), 5.40-5.65 (2H, m), 6.74 (1H, dd), 6.78 (1H, d), 6.91 (1H, d).

Example 49

Preparation of N-{cis-4-[(Z)-1-butenyl]cyclohexyl}-2-(4-hydroxy-3-methoxyphenyl)acetamide

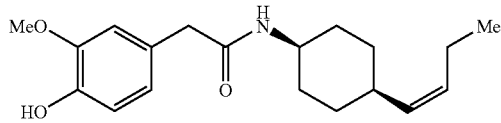

(1) To a mixture of 1.9 M sodium hexamethyldisilazane solution (in tetrahydrofuran, 2.1 ml) and anhydrous tetrahydrofuran (10 ml) was added n-propyltriphenyl-phosphonium bromide (1.52 g) at room temperature, and the mixture was stirred for 30 minutes. The reaction mixture was cooled to −78° C., and then a solution of t-butyl cis-4-formylcyclohexylcarbamate (900 mg) in anhydrous tetrahydrofuran (5 ml) was added thereto. The reaction mixture was gradually warmed to 25° C. and stirred overnight. To the reaction mixture was added saturated aqueous ammonium chloride, and the mixture was extracted with ethyl acetate, the organic layer was washed with brine, dried over sodium sulfate, and then the solvent was removed in vacuo. After diethyl ether was added to the residue, the precipitate was filtered off and then the filtrate was concentrated under reduced pressure. The residue was purified by a silica gel chromatography (eluent: gradient from 100% hexane/0% ethyl acetate to 0% hexane/100% ethyl acetate) to give 405 mg of t-butyl cis-4-[(Z)-1-butenyl]cyclohexylcarbamate.

(2) To a solution of the above product (1) (400 mg) in ethyl acetate (6 ml) was added toluenesulfonic acid monohydrate (300 mg), and the mixture was stirred at 60° C. for 1 hour. And the reaction mixture was stirred at room temperature for another 1 hour, and then the precipitated crystal was filtrated to give 295 mg of cis-4-[(Z)-1-butenyl]cyclohexylamine p-toluenesulfonate.

(3) To a mixture of the above product (2) (295 mg), 4-hydroxy-3-methoxyphenylacetic acid (182 mg), and benzotriazol-1-yloxy-tris(pyrrolidino)phosphonium hexafluorophosphate (520 mg) in dichloromethane (10 ml) under ice-cooling was added triethylamine (0.38 ml). The mixture was stirred at room temperature for 1 hour, and then washed with brine, and the organic layer was dried over sodium sulfate, then the solvent was removed in vacuo. The residue was purified by a silica gel chromatography (eluent: gradient from 100% hexane/0% ethyl acetate to 0% hexane/100% ethyl acetate) and recrystallized from hexane-ethyl acetate to give 160 mg of the desired compound.

$^1$H-NMR (CDCl$_3$, δ): 0.94 (3H, d), 1.01-1.15 (2H, m), 1.55-1.75 (6H, m), 1.97-2.08 (2H, m), 2.30-2.48 (1H, m), 3.50 (2H, s), 3.89 (3H, s), 3.92-4.05 (1H, m), 5.15 (1H, dd), 5.28 (1H, dt), 5.50 (1H, d), 5.62 (1H, s), 6.74 (1H, dd), 6.77 (1H, d), 6.91 (1H, d).

Examples 50-51

Instead of n-propyltriphenylphosphonium bromide of Example 49, various phosphonium halides are treated in a similar manner of Example 49 to give the compounds listed in Table 6.

The compound of Example 46: [α]$_D^{25}$ −4.0° (c=0.50, MeOH)

TABLE 6

| | Structure | $^1$H-NMR (CDCl$_3$, δ) |
|---|---|---|
| Example 50 | MeO, HO-phenyl-CH$_2$-C(O)-NH-cyclohexyl-CH=CH-Me | 1.01-1.15 (2H, m), 1.50-1.78 (9H, m), 2.30-2.46 (1H, m), 3.50 (2H, s), 3.89 (3H, s), 3.92-4.05 (1H, m), 5.21 (1H, dd), 5.36 (1H, dt), 5.50 (1H, d), 5.61 (1H, s), 6.75 (1H, dd), 6.78 (1H, d), 6.91 (1H, d) |
| Example 51 | MeO, HO-phenyl-CH$_2$-C(O)-NH-cyclohexyl-CH$_2$-CH=CH-CH$_2$-CH(Me)$_2$ | 0.87 (6H, d), 1.04 (2H, m), 1.45-1.60 (7H, m), 1.89 (2H, t), 2.34 (1H, m), 3.50 (2H, s), 3.89 (3H, s), 3.98 (1H, m), 5.19-5.33 (2H, m), 5.51 (1H, brs), 5.65 (1H, s), 6.75 (1H, dd), 6.78 (1H, d), 6.91 (1H, d). |

Example 52

Preparation of N-{trans-4-[(E)-1-butenyl]cyclohexyl}-2-(4-hydroxy-3-methoxyphenyl)acetamide

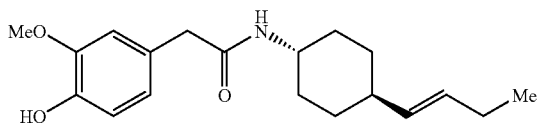

(1) To a mixture of 1-phenyl-5-propylsulfonyl-1H-tetrazole (3.34 g) and anhydrous ethylene glycol dimethyl ether (60 ml) at −60° C. was added 0.5 M hexamethyldisilazane potassium solution (in toluene, 26.6 ml), and the mixture was stirred for 30 minutes. Under the same condition, a solution of t-butyl trans-4-formylcyclohexylcarbamate (3.02 g) in anhydrous ethylene glycol dimethyl ether (15 ml) was added thereto and the reaction mixture was gradually warmed to 25° C. and stirred overnight. To the reaction mixture was added water, and the mixture was stirred for 1 hour, then extracted with diethyl ether, and the organic layer was washed with brine, dried over sodium sulfate, and then the solvent was removed in vacuo. The residue was purified by a silica gel chromatography (eluent: gradient from 100% hexane/0% ethyl acetate to 0% hexane/100% ethyl acetate) to give 1.31 g of t-butyl trans-4-[(E)-1-butenyl]cyclohexyl-carbamate.

(2) To a solution of the above product (1) (1.30 g) in ethyl acetate (20 ml) was added p-toluenesulfonic acid monohydrate (977 mg), and the mixture was stirred at 60° C. for 1 hour. To the reaction mixture was added hexane (10 ml), and the precipitated crystal was collected by filtration to give 1.32 g of trans-4-[(E)-1-butenyl]cyclohexylamine p-toluenesulfonate.

(3) To a mixture of the above product (2) (1.32 g), 4-hydroxy-3-methoxyphenyacetic acid (739 mg), and benzotriazol-1-yloxy-tris(pyrrolidino)phosphonium hexafluorophosphate (2.11 g) in dichloromethane (30 ml) under ice-cooling was added triethylamine (1.7 ml). The reaction mixture was stirred at room temperature for 1 hour, and then washed with saturated aqueous ammonium chloride and then brine. The organic layer was dried over sodium sulfate, and then the solvent was removed in vacuo. The residue was purified by a silica gel chromatography (eluent: gradient from 100% hexane/0% ethyl acetate to 0% hexane/100% ethyl acetate) to give 710 mg of the desired compound.

$^1$H-NMR (CDCl$_3$, δ): 0.90-1.30 (4H, m), 0.94 (3H, t), 1.56-2.05 (7H, m), 3.47 (2H, s), 3.61-3.78 (1H, m), 3.89 (3H, s), 5.18 (1H, d), 5.31 (1H, dd), 5.41 (1H, dt), 5.61 (1H, s), 6.71 (1H, dd), 6.75 (1H, d), 6.88 (1H, d).

Examples 53-58

Instead of 1-phenyl-5-propylsulfonyl-1H-tetrazole of Example 52, various 5-alkylsulfonyl-1-phenyl-1H-tetrazoles are treated in a similar manner of Example 52 to give the compounds listed in Table 7.

TABLE 7

| | Structure | $^1$HNMR (CDCl$_3$, δ) |
|---|---|---|
| Example 53 | MeO, HO-phenyl-CH$_2$-C(O)-NH-cyclohexyl-CH=CH-Me | 0.96-1.26 (4H, m), 1.50-1.95 (5H, m), 1.63 (3H, d), 3.47 (2H, s), 3.64-3.75 (1H, m), 3.89 (3H, s), 5.18 (1H, dd), 5.33 (1H, d), 5.39 (1H, dt), 5.58 (1H, s), 6.71 (1H, dd), 6.75 (1H, d), 6.88 (1H, d). |

TABLE 7-continued

| | Structure | ¹HNMR (CDCl₃, δ) |
|---|---|---|
| Example 54 | (structure) | 0.86 (3H, t), 0.97-1.40 (6H, m), 1.50-2.02 (7H, m), 3.47 (2H, s), 3.63-3.78 (1H, m), 3.89 (3H, s), 5.20 (1H, dd), 5.27 (1H, d), 5.35 (1H, dt), 5.59 (1H, s), 6.71 (1H, dd), 6.75 (1H, d), 6.88 (1H, d). |
| Example 55 | (structure) | 0.25-0.34 (2H, m), 0.61-0.72 (2H, m), 0.91-1.40 (4H, m), 1.55-2.00 (5H, m), 2.10-2.23 (1H, m), 3.47 (2H, s), 3.67-3.77 (1H, m), 3.88 (3H, s), 4.89 (1H, dd), 5.18 (1H, d), 5.41 (1H, dd), 5.59 (1H, s), 6.71 (1H, dd), 6.75 (1H, d), 6.88 (1H, d). |
| Example 56 | (structure) | 0.84 (6H, d), 0.94-1.30 (5H, m), 1.50-1.96 (7H, m), 3.47 (2H, s), 3.62-03.76 (1H, m), 3.89 (3H, s), 5.18 (1H, d), 5.27 (1H, dd), 5.33 (1H, dt), 5.59 (1H, s), 6.71 (1H, dd), 6.75 (1H, d), 6.88 (1H, d). |
| Example 57 | (structure) | 0.98-1.27 (6H, m), 1.61-2.11 (9H, m), 2.78-3.90 (1H, m), 3.47 (2H, s), 3.63-3.78 (1H, m), 3.89 (3H, s), 5.18 (1H, d), 5.21 (1H, dt), 5.49 (1H, dd), 5.59 (1H, s), 6.71 (1H, dd), 6.75 (1H, d), 6.89 (1H, d). |
| Example 58 | (structure) | 0.01-0.11 (2H, m), 0.38-0.46 (2H, m), 0.91-1.30 (5H, m), 1.50-2.10 (7H, m), 3.47 (2H, s), 3.65-3.79 (1H, m), 3.89 (3H, s), 5.18 (1H, d), 5.34 (1H, dt), 5.42 (1H, dd), 5.59 (1H, s), 6.71 (1H, dd), 6.75 (1H, d), 6.88 (1H, d). |

Example 59

Preparation of N-[trans-4-(2-cyclobutylethyl)cyclohexyl]-2-(4-hydroxy-3-methoxyphenyl)acetamide

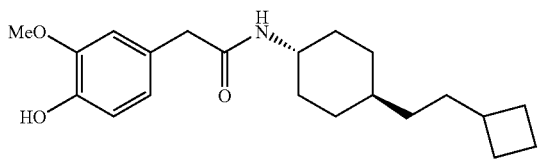

The compound (180 mg) of Example 57 was dissolved in ethanol (12 ml), platinum oxide (18 mg) was added to the solution, and the mixture was hydrogenated at 25° C. The catalyst was removed by filtration from the reaction mixture, and the solvent was evaporated under reduced pressure. The residue was purified by a silica gel chromatography (eluent: gradient from 100% hexane/0% ethyl acetate to 0% hexane/100% ethyl acetate) to give 96 mg of the desired compound.

¹H-NMR (CDCl₃, δ): 0.91-1.12 (8H, m), 1.23-1.36 (2H, m), 1.49-2.20 (10H, m), 3.46 (2H, s), 3.60-3.79 (1H, m), 3.89 (3H, s), 5.18 (1H, d), 5.60 (1H, s), 6.71 (1H, dd), 6.75 (1H, d), 6.88 (1H, d).

Example 60

Preparation of 2-(4-hydroxy-3-methoxyphenyl)-N-{cis-4-[(E)-1-pentenyl]cyclohexyl}acetamide

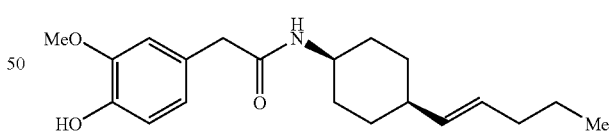

(1) To a mixture of 5-butylsulfonyl-1-phenyl-1H-tetrazole (3.54 g) and anhydrous ethylene glycol dimethyl ether (60 ml) at −60° C. was added 0.5 M hexamethyldisilazane potassium solution (in toluene, 26.6 ml), and the mixture was stirred for 20 minutes. Under the same condition, a solution of t-butyl cis-4-formylcyclohexylcarbamate (3.02 g) in anhydrous ethylene glycol dimethyl ether (15 ml) was added to the mixture. And the reaction mixture was gradually warmed to 25° C. and stirred overnight. To the reaction mixture was added water, and the mixture was stirred for 1 hour, then extracted with diethyl ether, and the organic layer was washed with brine, dried over sodium sulfate, and then the solvent was removed in vacuo. The residue was purified by a silica gel chromatography (eluent: gradient from 100% hexane/0% ethyl acetate to 0% hexane/100% ethyl acetate) to give 2.38 g of t-butyl cis-{4-[(E)-1-pentenyl]cyclohexyl}carbamate.

(2) To a solution of the above product (1) (2.35 g) in ethyl acetate (25 ml) was added p-toluenesulfonic acid monohydrate (1.67 g), and then the mixture was stirred at 60° C. for 1 hour. To the reaction mixture was added hexane (25 ml), and the precipitated crystal was filtrated to give 2.17 g of cis-4-[(E)-1-pentenyl]cyclohexylamine p-toluenesulfonate.

(3) To a mixture of the above product (2) (2.17 g), 4-hydroxy-3-methoxyphenyacetic acid (1.16 g), benzotriazol-1-yloxy-tris(pyrrolidino)phosphonium hexafluorophosphate (3.33 g) and dichloromethane (50 ml) under ice-cooling was added triethylamine (2.68 ml). The reaction mixture was stirred at room temperature for 1 hour, and then washed with saturated aqueous ammonium chloride and then brine. The organic layer was dried over sodium sulfate, and then the solvent was removed in vacuo. The residue was purified by a silica gel chromatography (eluent: gradient from 100% hexane/0% ethyl acetate to 0% hexane/100% ethyl acetate) and the recrystallized from hexane-ethyl acetate to give 770 mg of the desired compound.

$^1$H-NMR (CDCl$_3$, δ): 0.87 (3H, t), 1.00-1.18 (2H, m), 1.30-1.65 (8H, m), 1.90-2.18 (3H, m), 3.49 (2H, s), 3.89 (3H, s), 3.89-3.99 (1H, m), 5.28 (1H, dd), 5.34 (1H, dt), 5.45 (1H, d), 5.63 (1H, s), 6.74 (1H, dd), 6.77 (1H, d), 6.90 (1H, d).

Examples 61-67

Instead of 5-butylsulfonyl-1-phenyl-1H-tetrazole of Example 60, various 5-alkylsulfonyl-1-phenyl-1H-tetrazoles are treated in a similar manner of Example 60 to give the compounds listed in Table 8.

TABLE 8

| | Structure | $^1$H-NMR (CDCl$_3$, δ) |
|---|---|---|
| Example 61 | 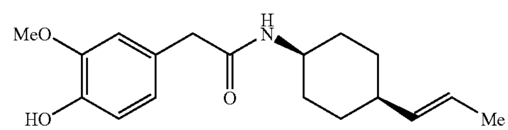 | 1.00-1.17 (2H, m), 1.50-1.61 (6H, m), 1.64 (3H, d), 1.96-2.08 (1H, m), 3.49 (2H, s), 3.89 (3H, s), 3.89-3.98 (1H, m), 5.31 (1H, dd), 5.37 (1H, dt), 5.45 (1H, d), 5.59 (1H, s), 6.74 (1H, dd), 6.77 (1H, d), 6.90 (1H, d). |
| Example 62 | 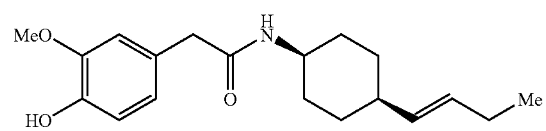 | 0.96 (3H, t), 1.00-1.20 (2H, m), 1.30-1.65 (6H, m), 1.90-2.10 (3H, m), 3.49 (2H, s), 3.89 (3H, s), 3.89-4.01 (1H, m), 5.27 (1H, dd), 5.39 (1H, dt), 5.48 (1H, d), 5.61 (1H, s), 6.74 (1H, dd), 6.77 (1H, d), 6.91 (1H, d). |
| Example 63 | 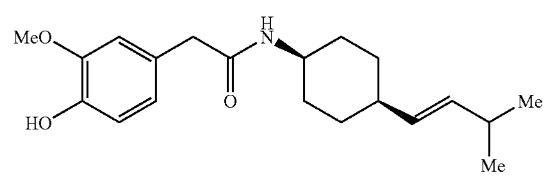 | 0.95 (6H, d), 1.00-1.16 (2H, m), 1.45-1.63 (6H, m), 1.90-2.07 (1H, m), 2.12-2.24 (1H, m), 3.49 (2H, s), 3.89 (3H, s), 3.89-4.01 (1H, m), 5.23 (1H, dd), 5.31 (1H, dd), 5.46 (1H, d), 5.59 (1H, s), 6.75 (1H, dd), 6.77 (1H, d), 6.91 (1H, d). |
| Example 64 | 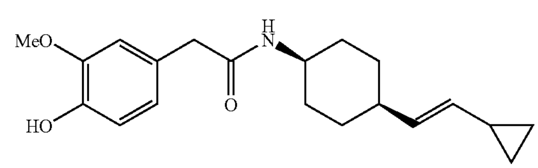 | 0.22-0.33 (2H, m), 0.60-0.71 (2H, m), 1.01-1.41 (4H, m), 1.40-1.67 (5H, m), 1.92-2.07 (1H, m), 3.49 (2H, s), 3.89 (3H, s), 3.87-4.01 (1H, m), 4.86 (1H, dd), 5.41 (1H, dd), 5.46 (1H, d), 5.62 (1H, s), 6.74 (1H, dd), 6.77 (1H, d), 6.91 (1H, d). |
| Example 65 | 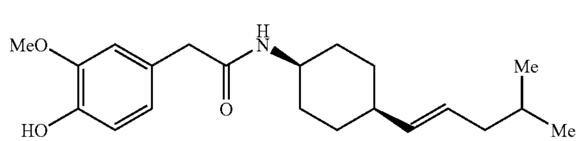 | 0.86 (6H, d), 1.00-1.16 (2H, m), 1.45-1.63 (7H, m), 1.85 (2H, dd), 1.97-2.09 (1H, m), 3.49 (2H, s), 3.89 (3H, s), 3.89-4.39 (1H, m), 5.26 (1H, dd), 5.33 (1H, dt), 5.46 (1H, d), 5.59 (1H, s), 6.74 (1H, dd), 6.77 (1H, d), 6.90 (1H, d). |

TABLE 8-continued

| | Structure | $^1$H-NMR (CDCl$_3$, δ) |
|---|---|---|
| Example 66 | 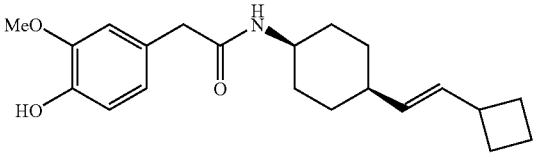 | 0.99-1.12 (2H, m), 1.01-1.41 (6H, m), 1.70-2.11 (7H, m), 2.78-2.90 (1H, m), 3.49 (2H, s), 3.89 (3H, s), 3.87-4.01 (1H, m), 5.23 (1H, dd), 5.45 (1H, dd), 5.48 (1H, d), 5.61 (1H, s), 6.74 (1H, dd), 6.77 (1H, d), 6.91 (1H, d). |
| Example 67 | 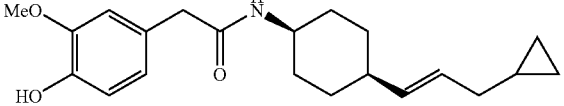 | 0.01-0.10 (2H, m), 0.37-0.46 (2H, m), 0.61-1.71 (1H, m), 1.01-1.19 (2H, m), 1.49-1.67 (6H, m), 1.89 (2H, dd), 1.98-2.09 (1H, m), 3.49 (2H, s), 3.89 (3H, s), 3.87-4.01 (1H, m), 5.34 (1H, dd), 5.41 (1H, dt), 5.48 (1H, d), 5.61 (1H, s), 6.74 (1H, dd), 6.77 (1H, d), 6.91 (1H, d). |

Example 68

Preparation of 2-(4-hydroxy-3-methoxyphenyl)-N-(cis-4-propylcyclohexyl)acetamide

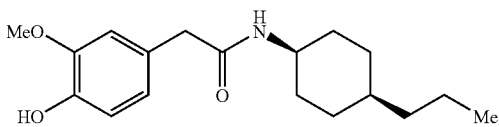

The compound (150 mg) of Example 61 was dissolved in ethanol (6 ml), platinum oxide (20 mg) was added to the solution, and the mixture was hydrogenated at 25° C. The catalyst was removed by filtration from the reaction mixture, and the solvent was evaporated under reduced pressure. The residue was purified by a silica gel chromatography (eluent: gradient from 100% hexane/0% ethyl acetate to 0% hexane/100% ethyl acetate) to give 88 mg of the desired compound.

$^1$H-NMR (CDCl$_3$, δ): 0.86 (3H, t), 1.08-1.36 (5H, m), 1.40-1.60 (8H, m), 3.49 (2H, s), 3.89 (3H, s), 3.90-4.01 (1H, m), 5.50 (1H, d), 5.60 (1H, brs), 6.74 (1H, dd), 6.77 (1H, d), 6.91 (1H, d).

Examples 69-71

Instead of the compound of Example 61 in Example 68, the compounds of Examples 51, 66, and 67 are treated in a similar manner of Example 68 to give the compounds listed in Table 9.

TABLE 9

| | Structure | $^1$H-NMR (CDCl$_3$, δ) |
|---|---|---|
| Example 69 | 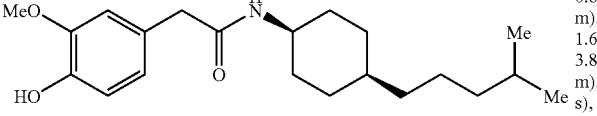 | 0.87 (6H, d), 1.40-1.57 (4H, m), 1.01-1.34 (6H, m), 1.45-1.60 (6H, m), 3.49 (2H, s), 3.88 (3H, s), 3.90-4.02 (1H, m), 5.50 (1H, d), 5.62 (1H, s), 6.74 (1H, dd), 6.77 (1H, d), 6.91 (1H, d). |
| Example 70 | 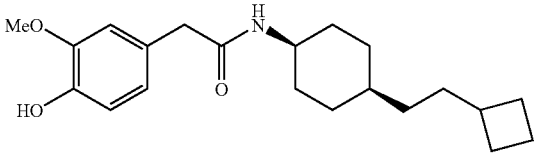 | 0.80-1.09 (4H, m), 1.20-1.51 (11H, m),1.71-2.08 (4H, m), 2.10-2.21 (1H, m), 3.49 (2H, s), 3.89 (3H, s), 3.90-4.02 (1H, m), 5.49 (1H, d), 5.60 (1H, s), 6.74 (1H, dd), 6.77 (1H, d), 6.91 (1H, d). |
| Example 71 | 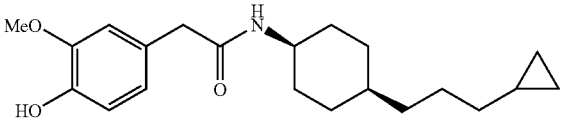 | −0.07-0.06 (2H, m), 0.32-0.42 (2H, m), 0.65-0.76 (1H, m), 0.80-0.92 (2H, m), 1.11-1.38 (6H, m), 1.40-1.71 (7H, m), 3.49 (2H, s), 3.89 (3H, s), 3.90-4.02 (1H, m), 5.49 (1H, d), 5.61 (1H, s), 6.74 (1H, dd), 6.77 (1H, d), 6.91 (1H, d). |

Example 72

Preparation of 2-(4-hydroxy-3-methoxyphenyl)-N-{trans-4-[(E)-3-methyl-1,3-butadienyl]cyclohexyl}acetamide

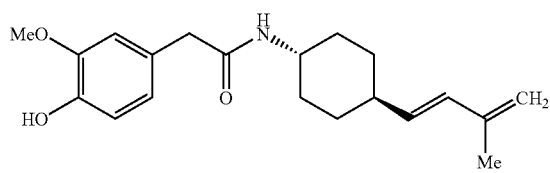

(1) To a mixture of sodium hydride (793 mg) and anhydrous tetrahydrofuran (80 ml) under ice-cooling was added diethyl 2-oxopropylphosphonate (3.85 g). The mixture was stirred for 15 minutes and then a solution of t-butyl trans-4-formylcyclohexylcarbamate (3.00 g) in anhydrous tetrahydrofuran (30 ml) was added thereto. The mixture was warmed to 25° C. and stirred for 3 hours. To the reaction mixture was added saturated aqueous ammonium chloride, the mixture was extracted with ethyl acetate, and the organic layer was washed with brine, dried over sodium sulfate, and then the solvent was removed in vacuo. The residue was purified by a silica gel chromatography (eluent: gradient from 100% hexane/0% ethyl acetate to 0% hexane/100% ethyl acetate) to give 3.46 g of t-butyl trans-4-[(E)-3-oxo-1-butenyl]cyclohexylcarbamate.

(2) To a mixture of 1.9 M sodium hexamethyldisilazane solution (in tetrahydrofuran, 4.7 ml) and anhydrous tetrahydrofuran (20 ml) was added methyltriphenyl phosphonium bromide (3.21 g) at room temperature, and the mixture was stirred for 10 minutes. The reaction mixture was cooled to −78° C., and then a solution of the above product (1) (1.20 g) in anhydrous tetrahydrofuran (10 ml) was added thereto. And then the reaction mixture was gradually warmed to 0° C. To the reaction mixture was added saturated aqueous ammonium chloride, the mixture was extracted with ethyl acetate, washed with brine. The organic layer was dried over sodium sulfate, and then concentrated in vacuo. After diethyl ether was added to the residue, the precipitate was filtered off and then the filtrate was concentrated under reduced pressure. The residue was purified by a silica gel chromatography (eluent: gradient from 100% hexane/0% ethyl acetate to 0% hexane/100% ethyl acetate) to give 975 mg of t-butyl trans-4-[(E)-3-methyl-1,3-butadienyl]cyclohexylcarbamate.

(3) To a solution of the above product (2) (975 mg) in ethyl acetate (12 ml) was added p-toluenesulfonic acid monohydrate (695 mg), and the mixture was stirred at 60° C. for 1 hour. To the reaction mixture was added hexane (10 ml), and the precipitated crystal was collected by filtration to give 560 mg of trans-4-[(E)-3-methyl-1,3-butadienyl]cyclohexylamine p-toluenesulfonate.

(4) To a mixture of the above product (3) (560 mg), 4-hydroxy-3-methoxyphenylacetic acid (302 mg), and benzotriazol-1-yloxy-tris (pyrrolidino) phosphonium hexafluorophosphate (863 mg) in dichloromethane (20 ml) under ice-cooling was added triethylamine (0.69 ml). The reaction mixture was stirred at room temperature for 1 hour, and then washed with saturated aqueous ammonium chloride and then brine. The organic layer was dried over sodium sulfate, and then the solvent was removed in vacuo. The residue was purified by a silica gel chromatography (eluent: chloroform) and recrystallized from hexane-ethyl acetate to give 295 mg of the desired compound.

$^1$H-NMR (CDCl$_3$, δ): 0.89-1.35 (7H, m), 1.70-1.83 (2H, m), 1.81 (3H, s), 1.89-2.00 (2H, m), 3.47 (2H, s), 3.62-3.80 (1H, m), 3.89 (3H, s), 5.20 (1H, d), 5.53 (1H, dd), 5.60 (1H, s), 6.09 (1H, d), 6.72 (1H, dd), 6.76 (1H, d), 6.89 (1H, d).

Example 73

Preparation of 2-(4-hydroxy-3-methoxyphenyl)-N-{trans-4-[(Z)-3-pentenyl]cyclohexyl}acetamide

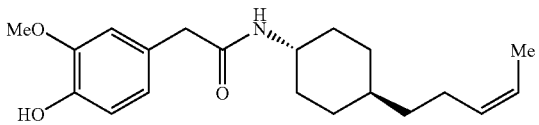

(1) To a mixture of sodium hydride (1.07 g) and anhydrous tetrahydrofuran (120 ml) under ice-cooling was added diethyl N-methoxy-N-methylcarbamoylmethylphosphonate (6.40 g). The mixture was stirred for 15 minutes, and then a solution of t-butyl trans-4-formylcyclohexylcarbamate (5.00 g) in anhydrous tetrahydrofuran (20 ml) was added thereto, and the mixture was stirred for 2 hours under the same condition. To the reaction mixture was added saturated aqueous ammonium chloride, the mixture was extracted with ethyl acetate, the organic layer was washed with brine, dried over sodium sulfate, and then the solvent was removed in vacuo. The residue was purified by a silica gel chromatography (eluent: gradient from 100% hexane/0% ethyl acetate to 0% hexane/100% ethyl acetate) to give 4.30 g of t-butyl trans-4-[(E)-2-(N-methoxy-N-methylcarbamoyl)-vinyl]cyclohexylcarbamate.

(2) To a mixture of lithium aluminium hydride (524 mg) and anhydrous tetrahydrofuran (70 ml) at −78° C. was added a solution of the above product (1) (4.30 g) in anhydrous tetrahydrofuran (40 ml). The mixture was gradually warmed to 0° C., and saturated aqueous ammonium chloride was added to the reaction mixture, and the mixture was extracted with ethyl acetate. The organic layer was washed with brine, dried over sodium sulfate, and then the solvent was removed in vacuo. The residue was purified by a silica gel chromatography (eluent: gradient from 100% hexane/0% ethyl acetate to 0% hexane/100% ethyl acetate) to give 2.65 g of t-butyl trans-4-[(E)-2-formylvinyl]cyclohexylcarbamate.

(3) The above product (2) (2.0 g) was dissolved in ethanol (25 ml), 5% palladium/carbon (100 mg) was added to the solution, and the mixture was hydrogenated at 25° C. The catalyst was removed by filtration from the reaction mixture, and the solvent was evaporated under reduced pressure to give 1.68 g of t-butyl trans-4-(2-formylethyl)cyclohexylcarbamate.

(4) To a mixture of 1.9 M sodium hexamethyldisilazane solution (in tetrahydrofuran, 3.03 ml) and anhydrous tetrahydrofuran (15 ml) was added ethyltriphenylphosphonium bromide (2.33 g) at room temperature, and the mixture was stirred for 30 minutes. To the reaction mixture at −78° C. was added a solution of the above product (3) (800 mg) in anhydrous tetrahydrofuran (5 ml). The reaction mixture was gradually warmed to 25° C. and stirred overnight. To the reaction mixture was added saturated aqueous ammonium chloride, and the mixture was extracted with ethyl acetate, the organic layer was washed with brine, dried over sodium sulfate, and then the solvent was removed in vacuo. After diethyl ether was added to the residue, the precipitate was filtered off and then the filtrate was concentrated under reduced pressure. The residue was purified by a silica gel chromatography (eluent: gradient from 100% hexane/0% ethyl acetate to 0% hexane/100% ethyl acetate) to give 610 mg of t-butyl trans-4-[(Z)-3-pentenyl]cyclohexylcarbamate.

(5) To a solution of the above product (4) (600 mg) in ethyl acetate (7 ml) was added p-toluenesulfonic acid monohydrate (428 mg), and the mixture was stirred at 60° C. for 1 hour. The reaction mixture was cooled in ice-water bath, and then the precipitated crystal was collected by filtration to give 480 mg of trans-4-[(Z)-3-pentenyl]cyclohexylamine p-toluenesulfonate.

(6) To a mixture of the above product (5) (480 mg), 4-hydroxy-3-methoxyphenyacetic acid (258 mg), and benzotriazol-1-yloxy-tris(pyrrolidino)phosphonium hexafluorophosphate (738 mg) in dichloromethane (9 ml) under ice-cooling was added triethylamine (0.59 ml). The reaction mixture was stirred at room temperature for 1 hour, and then washed with saturated aqueous ammonium chloride and then brine. The organic layer was dried over sodium sulfate, and then the solvent was removed in vacuo. The residue was purified by a silica gel chromatography (eluent: gradient from 100% hexane/0% ethyl acetate to 0% hexane/100% ethyl acetate) and then recrystallized from hexane-ethyl acetate to give 260 mg of the desired compound.

$^1$H-NMR (CDCl$_3$, δ): 0.91-1.28 (5H, m), 1.52-1.76 (9H, m), 1.86-2.08 (2H, m), 3.46 (2H, s), 3.63-3.73 (1H, m), 3.88 (3H, s), 5.19 (1H, d), 5.32 (1H, dt), 5.42 (1H, dq), 5.58 (1H, s), 6.71 (1H, dd), 6.76 (1H, d), 6.88 (1H, d).

Example 74

Preparation of N-[trans-4-(3-butenyl)cyclohexyl]-2-(4-hydroxy-3-methoxyphenyl)acetamide

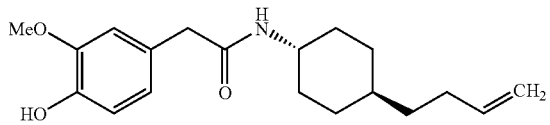

The above desired compound was prepared in a similar manner of Example 73 using methyltriphenylphosphonium bromide instead of ethyltriphenylphosphonium bromide of Example 73 (4).

$^1$H-NMR (CDCl$_3$, δ): 0.91-1.31 (5H, m), 1.56-2.07 (8H, m), 3.47 (2H, s), 3.63-3.73 (1H, m), 3.89 (3H, s), 4.83-5.02 (2H, m), 5.19 (1H, d), 5.60 (1H, s), 5.71 (1H, ddt), 6.71 (1H, dd), 6.76 (1H, d), 6.89 (1H, d).

Example 75

Preparation of 2-(4-hydroxy-3-methoxyphenyl)-N-{trans-4-[(E)-3-pentenyl]cyclohexyl}acetamide

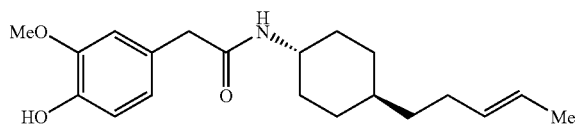

(1) To a mixture of 5-ethylsulfonyl-1-phenyl-1H-tetrazole (5.0 g) and anhydrous ethylene glycol dimethyl ether (50 ml) at −60° C. was added 0.5 M potassium hexamethyldisilazane solution (in toluene, 19.7 ml), and the mixture was stirred for 20 minutes. Under the same condition, a solution of t-butyl trans-4-(2-formylethyl)cyclohexylcarbamate (2.65 g) (Example 73 (3)) in anhydrous ethylene glycol dimethyl ether (20 ml) was added thereto. The reaction mixture was gradually warmed to 25° C. and stirred overnight. To the reaction mixture was added water, and the mixture was stirred for 1 hour, then extracted with diethyl ether. The organic layer was washed with brine, dried over sodium sulfate, and then the solvent was removed in vacuo. The residue was purified by a silica gel chromatography (eluent: gradient from 100% hexane/0% ethyl acetate to 0% hexane/100% ethyl acetate) to give 252 mg of t-butyl trans-4-[(E)-3-pentenyl]cyclohexylcarbamate.

(2) To a solution of the above product (1) (240 mg) in ethyl acetate (4 ml) was added p-toluenesulfonic acid monohydrate (171 mg), and the mixture was stirred at 60° C. for 1 hour. To the reaction mixture was added hexane (12 ml), and the precipitated crystal was collected by filtration to give 259 mg of trans-4-[(E)-3-pentenyl]cyclohexylamine p-toluenesulfonate.

(3) To a mixture of the above product (2) (259 mg), 4-hydroxy-3-methoxyphenylacetic acid (139 mg), and benzotriazol-1-yloxy-tris(pyrrolidino)phosphonium hexafluorophosphate (397 mg) in dichloromethane (6 ml) under ice-cooling was added triethylamine (0.59 ml). The reaction mixture was stirred at room temperature for 1 hour, and then washed with saturated aqueous ammonium chloride and then brine. The organic layer was dried over sodium sulfate, and then the solvent was removed in vacuo. The residue was purified by a silica gel chromatography (eluent: gradient from 100% hexane/0% ethyl acetate to 0% hexane/100% ethyl acetate) to give 95 mg of the desired compound.

$^1$H-NMR (CDCl$_3$, δ): 0.91-1.28 (8H, m), 1.56-2.00 (8H, m), 3.47 (2H, s), 3.63-3.74 (1H, m), 3.88 (3H, s), 5.18 (1H, d), 5.36 (1H, dt), 5.39 (1H, dq), 5.59 (1H, s), 6.71 (1H, dd), 6.75 (1H, d), 6.88 (1H, d).

Example 76

Preparation of N-(4-cyclohexylidenecyclohexyl)-2-(4-hydroxy-3-methoxyphenyl)acetamide

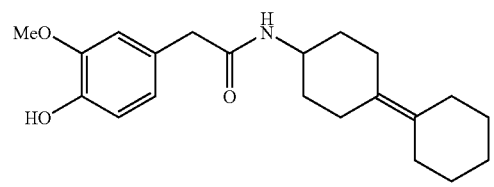

(1) Under nitrogen atmosphere, to a mixture of 2 M lithium diisopropylamide solution (in heptane/tetrahydro-furan/ethylbenzene, 50 ml) and anhydrous tetrahydrofuran (50 ml) under ice-cooling was added cyclohexanecarboxylic acid (5.58 ml) dropwise. After stirring the mixture at room temperature for 5 hours, the mixture was cooled again. A solution of 1,4-cyclohexadione monoethyleneketal (7.03 g) in anhydrous tetrahydrofuran (50 ml) was added dropwise to the reaction mixture, and then the resulting mixture was stirred overnight at room temperature. To the reaction mixture was added ice-water (250 ml), and the mixture was extracted with diisopropyl ether (250 ml×2). To the aqueous layer was added 1M aqueous citric acid (50 ml) to acidify the solution. The solution was extracted with a mixture of chloroform:methanol (9:1, 300 ml×2), and the organic layer was dried over sodium sulfate, and then the solvent was removed in vacuo. The resulting brown crystal (12 g) was dissolved in acetonitrile (500 ml), and thereto was added N,N-dimethylformamide dineopentylacetal (19 g), and the mixture was stirred at room temperature for 1 hour, then heated under reflux overnight. The acetonitrile was removed in vacuo, and to the residue was added diisopropyl ether and water. The mixture was separated with a separating funnel, and the organic layer was washed with brine, dried over magnesium sulfate. The solvent was removed in vacuo. The residue was purified by a silica gel chromatography (eluent: hexane/ethyl acetate=100/0 to 15/1) to give 7.1 g of 8-cyclohexylidene-1,4-dioxaspiro[4.5]decane.

(2) 2 M hydrochloric acid (10 ml) and tetrahydrofuran (30 ml) were added to the above product (1) (1.7 g), and the mixture was stirred at 45° C. for 3 hours. To the reaction mixture was added diisopropyl ether and water. The mixture was separated with a separating funnel, and then the organic layer was washed with brine, dried over magnesium sulfate. The solvent was removed in vacuo. The resulting crystal (1.3 g) was stirred at 65° C. for 3 hours with hydroxylamine hydrochloride (1.0 g), sodium acetate (1.2 g), methanol (30 ml), and water (15 ml). The methanol was removed in vacuo from the reaction mixture, and ethyl acetate and water was added to the residue. The mixture was separated with a separating funnel, and then the organic layer was washed with brine, dried over magnesium sulfate. The solvent was removed in vacuo. The residue was purified by a silica gel chromatography (eluent: hexane/ethyl acetate=6/1 to 4/1) to give 1.2 g of 4-cyclohexylidenecyclohexanone oxime.

(3) Under nitrogen atmosphere, to a suspension of lithium aluminium hydride (0.69 g) in anhydrous tetrahydrofuran (25 ml) under ice-cooling was added dropwise a solution of the above product (2) (1.2 g) in anhydrous tetrahydrofuran (25 ml), and then the mixture was heated under reflux for 3 hours. The reaction mixture was cooled in an ice-water bath, and ethyl acetate, 1M aqueous potassium sodium tartrate were added dropwise thereto to quench an excess of lithium aluminium hydride. The mixture was filtrated through Celite. The filtrate was dried over magnesium sulfate, and then the solvent was removed in vacuo. The mixture of resulting product (0.8 g), 4-hydroxy-3-methoxyphenyacetic acid (0.74 g), 1-ethyl-3-(3-dimethylaminopropyl)carbodiimide hydrochloride (0.95 g), 1-hydroxybenzotriazole (0.07 g) and dichloromethane (50 ml) was stirred overnight at room temperature. The reaction mixture was washed with water and then brine. The organic layer was dried over magnesium sulfate, and the solvent was removed in vacuo. The residue was purified by a silica gel chromatography (eluent: hexane/ethyl acetate=2/1) to give 0.42 g of the desired compound.

$^{1}$H-NMR (CDCl$_{3}$, δ): 0.98-1.11 (2H, m), 1.41-1.56 (6H, m), 1.80-1.94 (4H, m), 2.11-2.15 (4H, m), 2.50-2.58 (2H, m), 3.48 (2H, s), 3.88 (3H, s), 3.94 (1H, m), 5.26 (1H, d), 5.61 (1H, s), 6.71 (1H, dd), 6.75 (1H, d), 6.88 (1H, d).

Examples 77-81

Instead of cyclohexanecarboxylic acid of Example 76, various carboxylic compounds are treated in a similar manner of Example 76 to give the compounds listed in Table 10.

TABLE 10

| | Structure | $^{1}$HNMR (CDCl$_{3}$, δ) |
|---|---|---|
| Example 77 | 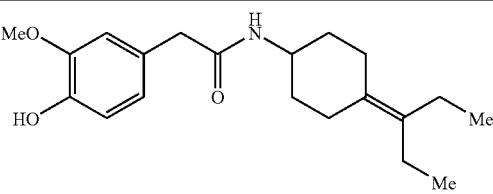 | 0.90 (6H, t), 0.98-1.11 (2H, m), 1.80-1.93 (4H, m), 1.98 (4H, q), 2.38-2.47 (2H, m), 3.48 (2H, s), 3.88 (3H, s), 3.93 (1H, m), 5.25 (1H, d), 5.62 (1H, br), 6.71 (1H, dd), 6.75 (1H, d), 6.88 (1H, d) |
| Example 78 | 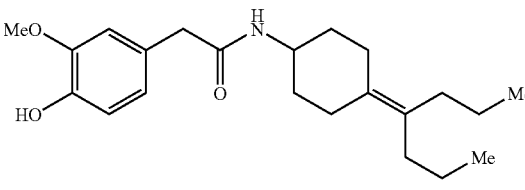 | 0.86 (6H, t), 0.97-1.10 (2H, m), 1.25-1.37 (4H, m), 1.80-1.96 (8H, m), 2.40-2.49 (2H, m), 3.48 (2H, s), 3.88 (3H, s), 3.93 (1H, m), 5.25 (1H, d), 5.62 (1H, br), 6.71 (1H, dd), 6.75 (1H, d), 6.88 (1H, d) |
| Example 79 | 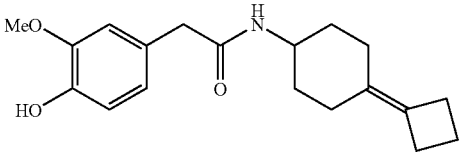 | 0.99-1.12 (2H, m), 1.74-1.92 (6H, m), 2.08-2.16 (2H, m), 2.57 (4H, m), 3.48 (2H, s), 3.88 (3H, s), 3.89 (1H, m), 5.26 (1H, d), 5.63 (1H, s), 6.71 (1H, dd), 6.75 (1H, d), 6.88 (1H, d) |
| Example 80 | 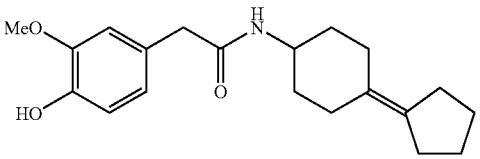 | 1.02-1.15 (2H, m), 1.58-1.62 (4H, m), 1.83-1.98 (4H, m), 2.11-2.18 (4H, m), 2.24-2.34 (2H, m), 3.48 (2H, s), 3.88 (3H, s), 3.90 (1H, m), 5.25 (1H, br), 5.63 (1H, s), 6.71 (1H, dd), 6.75 (1H, d), 6.88 (1H, d) |

TABLE 10-continued

| | Structure | $^1$HNMR (CDCl$_3$, δ) |
|---|---|---|
| Example 81 | 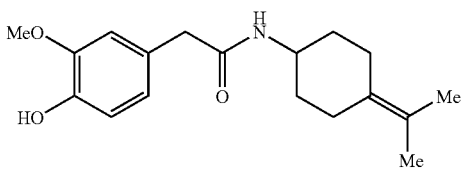 | 0.99-1.12 (2H, m), 1.40-1.55 (8H m), 1.81-1.94 (4H, m), 2.11-2.26 (4H, m), 2.45-2.52 (2H, m), 3.48 (2H, s), 3.88 (3H, s), 3.93 (1H, m), 5.27 (1H, d), 5.631 (1H, s), 6.71 (1H, dd), 6.75 (1H, d), 6.88 (1H, d) |

Example 82

Preparation of 2-(4-hydroxy-3-methoxyphenyl)-N-(4-isopropylidenecyclohexyl)acetamide (1) Under nitrogen atmosphere, to a suspension of isopropyltriphenylphosphonium iodide (16.2 g) in anhydrous tetrahydrofuran (70 ml) was added 2.7 M butyl lithium solution (in hexane, 14.5 ml) dropwise under ice-cooling. After stirring the mixture at room temperature for 30 minutes, a solution of 1,4-cyclohexadione monoethyleneketal (5.58 g) in anhydrous tetrahydrofuran (30 ml) was added dropwise thereto, and the mixture was stirred at the same temperature for 1 hour. To the reaction mixture was added water (20 ml), and the insoluble precipitate was filtrated off through Celite. The filtrate was concentrated under reduced pressure, and the residue was separated with a separating funnel between ethyl acetate and water. The organic layer was washed with brine, dried over magnesium sulfate, and then the solvent was removed in vacuo. The residue was purified by a silica gel chromatography (eluent: hexane/ethyl acetate=50/1 to 20/1) to give 1.2 g of 8-isopropylidene-1,4-dioxaspiro[4.5]decane.

(2) A silica gel (70-230 mesh, 6.4 g) was suspended in dichloromethane (19 ml), and 15% aqueous sulfuric acid (1.13 ml) was added dropwise thereto at room temperature, and then the mixture was stirred at room temperature for 2 minutes. The above product (1) (3.0 g) was added to the mixture, and the mixture was stirred at room temperature for 6 hours. The silica gel was filtrated off, and the filtrate was concentrated under reduced pressure. The resulting crude product was stirred with hydroxylamine hydrochloride (0.8 g)., sodium acetate (0.95 g), methanol (20 ml), and water (10 ml) at 65° C. for 3 hours. The methanol was evaporated under reduced pressure, and ethyl acetate and water were added to the residue. The mixture was separated with a separating funnel, the organic layer was washed with brine, dried over magnesium sulfate, and then the solvent was removed in vacuo. The residue was purified by a silica gel chromatography (eluent: hexane/ethyl acetate=6/1 to 4/1) to give 0.6 g of 4-isopropylidenecyclohexanone oxime.

(3) Under nitrogen atmosphere, to a suspension of lithium aluminium hydride (0.45 g) in anhydrous tetrahydrofuran (10 ml) under ice-cooling was added dropwise a solution of the above product (2) (0.6 g) in anhydrous tetrahydrofuran (10 ml), and the mixture was heated under reflux for 3 hours. The reaction mixture was cooled in an ice-water bath, and ethyl acetate and 1 M aqueous potassium sodium tartrate were added dropwise thereto to quench an excess of lithium aluminium hydride. The mixture was filtrated through Celite. The filtrate was dried over magnesium sulfate, and then the solvent was removed in vacuo. The mixture of resulting product (0.51 g), 4-hydroxy-3-methoxyphenyacetic acid (0.55 g), 1-ethyl-3-(3-dimethylaminopropyl)carbodiimide hydrochloride (0.69 g), 1-hydroxybenzotriazole (0.05 g) and dichloromethane (15 ml) was stirred overnight at room temperature. The reaction mixture was washed with water and then brine. The organic layer was dried over magnesium sulfate, and the solvent was removed in vacuo. The residue was purified by a silica gel chromatography (eluent: hexane/ethyl acetate=2/1) to give 0.09 g of the desired compound.

$^1$H-NMR (CDCl$_3$, δ): 0.99-1.12 (2H, m), 1.62 (6H, s), 1.80-1.92 (4H, m), 2.44-2.52 (2H, m), 3.48 (2H, s), 3.88 (3H, s), 3.92 (1H, m), 5.27 (1H, br), 5.67 (1H, s), 6.71 (1H, dd), 6.75 (1H, d), 6.88 (1H, d).

Example 83

Preparation of N-(trans-4-cyclohexylcyclohexyl)-2-(4-hydroxy-3-methoxyphenyl)acetamide

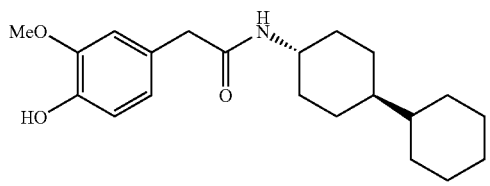

The compound (0.5 g) of Example 76 was dissolved in ethanol (20 ml), and 20% palladium hydroxide/carbon (150 mg) was added to the solution, and the mixture was hydrogenated at room temperature. After 2 hours, the catalyst was removed by filtration from the reaction mixture, and the solvent of the mixture was evaporated under reduced pressure. The residue was recrystallized from hexane-ethyl acetate to give 36 mg of the desired compound.

¹H-NMR (CDCl₃, δ): 0.84-1.27 (11H, m), 1.60-1.73 (7H, m), 1.91 (2H, m), 3.46 (2H, s), 3.66 (1H, m), 3.88 (3H, s), 5.18 (1H, d), 5.60 (1H, s), 6.71 (1H, dd), 6.75 (1H, d), 6.88 (1H, d).

Examples 84-87

Instead of the compound of Example 76 in Example 83, the compounds of Examples 77, 78, 79, and 81 are treated in a similar manner of Example 83 to give the compounds listed in Table 11.

were added water (300 ml) and then 28% aqueous ammonia to alkalize the solution. The mixture was extracted with dichloromethane, the organic layer was washed with brine, dried over magnesium sulfate, and then the solvent was evaporated under reduced pressure. To a mixture of the residual colorless oil (8.0 g) and triethylamine (8.5 ml) in dichloromethane (100 ml) was added dropwise a solution of triphenylmethyl chloride (15.6 g) in dichloromethane (80 ml), and the mixture was stirred at room temperature over-

TABLE 11

| | Structure | ¹H-NMR (CDCl₃, δ) |
|---|---|---|
| Example 84 | [structure: 2-(4-hydroxy-3-methoxyphenyl)-N-[4-(2-methylpropyl)cyclohexyl]acetamide] | 0.82 (6H, t), 0.90-1.02 (3H, m), 1.07-1.35 (7H, m), 1.60 (2H, m), 1.92 (2H, m), 3.47 (2H, s), 3.66 (1H, m), 3.88 (3H, s), 5.20 (1H, br), 5.66 (1H, s), 6.71 (1H, dd), 6.75 (1H, d), 6.88 (1H, d) |
| Example 85 | [structure: 2-(4-hydroxy-3-methoxyphenyl)-N-[4-(3-pentyl)cyclohexyl]acetamide] | 0.86 (6H, t), 0.95-1.34 (14H, m), 1.53-1.60 (2H, m), 1.88-1.96 (2H, m), 3.47 (2H, s), 3.67 (1H, m), 3.87 (3H, s), 5.29 (1H, d), 5.95 (1H, d), 6.70 (1H, dd), 6.75 (1H, d), 6.88 (1H, d) |
| Example 86 | [structure: 2-(4-hydroxy-3-methoxyphenyl)-N-(4-cyclobutylcyclohexyl)acetamide] | 0.77-1.10 (5H, m), 1.55-1.99 (11H, m), 3.46 (2H, s), 3.66 (1H, m), 3.88 (3H, s), 5.19 (1H, d), 5.64 (1H, s), 6.71 (1H, dd), 6.75 (1H, d), 6.88 (1H, d) |
| Example 87 | [structure: 2-(4-hydroxy-3-methoxyphenyl)-N-(4-cycloheptylcyclohexyl)acetamide] | 0.87-1.67 (20H, m), 1.91 (2H, m), 3.46 (2H, s), 3.66 (1H, m), 3.88 (3H, s), 5.18 (1H, d), 5.61 (1H, s), 6.71 (1H, dd), 6.75 (1H, d), 6.88 (1H, d) |

Example 88

Preparation of 2-(4-hydroxy-3-methoxyphenyl)-N-[4-(3-pentyl)-3-cyclohexenyl]acetamide

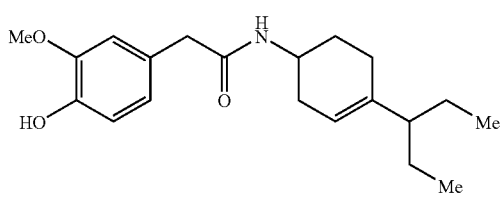

(1) To a solution of 4-amino-cyclohexanecarboxylic acid (9.2 g) in methanol (250 ml) was added concentrated sulfuric acid (11 ml) dropwise, and the mixture was heated under reflux for 48 hours. The methanol was evaporated under reduced pressure from the reaction mixture. To the residue night. The reaction mixture was washed with water and then brine. The organic layer was dried over magnesium sulfate, and the solvent was removed in vacuo. The residue was purified by a silica gel chromatography (eluent:hexane/ethyl acetate=10/1) to give 22 g of methyl 4-(triphenylmethylamino)cyclohexane-carbonate.

(2) Under nitrogen atmosphere, to a solution of the above product (1) (6.0 g) in anhydrous tetrahydrofuran (100 ml) under ice-cooling was added 0.91 M ethyl magnesium bromide solution (in tetrahydrofuran, 50 ml) dropwise, and then the mixture was stirred overnight at room temperature. The reaction mixture was cooled in an ice-water bath, and saturated aqueous ammonium chloride was added thereto dropwise. Ethyl acetate and water were added thereto and the resulting mixture was separated with a separating funnel. The organic layer was washed with saturated aqueous sodium hydrogen carbonate and then brine. The organic layer was dried over magnesium sulfate, and the solvent was removed in vacuo. The residue was purified by a silica gel chromatography (eluent: hexane/ethyl acetate=20/1 to 10/1) to give 3.2 g of 3-(4-triphenylmethyl-aminocyclohexyl)pentan-3-ol.

(3) To a solution of the above product (2) (3.2 g) in toluene (80 ml) was added p-toluenesulfonic acid monohydrate (2.9 g), and the mixture was stirred at 120° C. for 3 hours. The reaction mixture was cooled to ambient temperature and then washed with 1 M aqueous potassium carbonate and then brine. The organic layer was dried over magnesium sulfate, and the solvent was removed in vacuo. The mixture of resulting product, 4-hydroxy-3-methoxyphenylacetic acid (0.91 g), 1-ethyl-3-(3-dimethyl-aminopropyl)carbodiimide hydrochloride (1.2 g), 1-hydroxybenzotriazole (0.08 g) and dichloromethane (40 ml) was stirred overnight at room temperature. The reaction mixture was washed with water and then brine. The organic layer was dried over magnesium sulfate, and the solvent was removed in vacuo. The residue was purified by a silica gel chromatography (eluent: hexane/ethyl acetate=2/1) to give 0.69 g of the desired compound.

$^1$H-NMR (CDCl$_3$, δ): 0.67 (3H, t), 0.73 (3H, t), 1.08-1.38 (4H, m), 1.48-1.93 (6H, m), 2.33 (1H, d), 3.49 (2H, s), 3.88 (3H, s), 4.11 (1H, m), 5.23 (1H, s), 5.42 (1H, br), 5.70 (1H, s), 6.71 (1H, dd), 6.75 (1H, d), 6.87 (1H, d).

Example 89

Preparation of N-[4-(4-heptyl)-3-cyclohexenyl]-2-(4-hydroxy-3-methoxyphenyl)acetamide

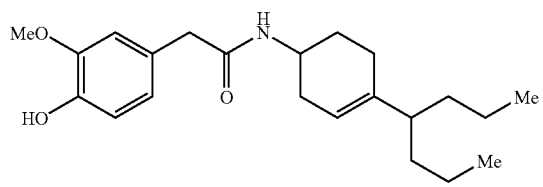

The above desired compound was prepared in a similar manner of Example 88 using propyl magnesium bromide instead of ethyl magnesium bromidein Example 88.

$^1$H-NMR (CDCl$_3$, δ): 0.81-0.85 (6H, m), 1.02-1.28 (9H, m), 1.50 (1H, m), 1.68-1.82 (2H, m), 1.83-1.95 (2H, m), 2.31 (1H, m), 3.49 (2H, s), 3.88 (3H, s), 4.07 (1H, m), 5.22 (1H, s), 5.40 (1H, d), 5.65 (1H, s), 6.69-6.75 (2H, m), 6.88 (1H, d).

Example 90

Preparation of N-[trans-4-(2-ethyl-1-butenyl)cyclohexyl]-2-(4-hydroxy-3-methoxyphenyl)acetamide

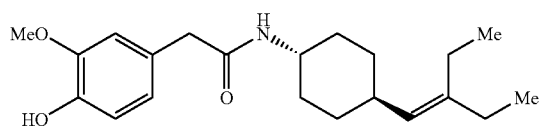

The above compound was prepared by the following procedure.

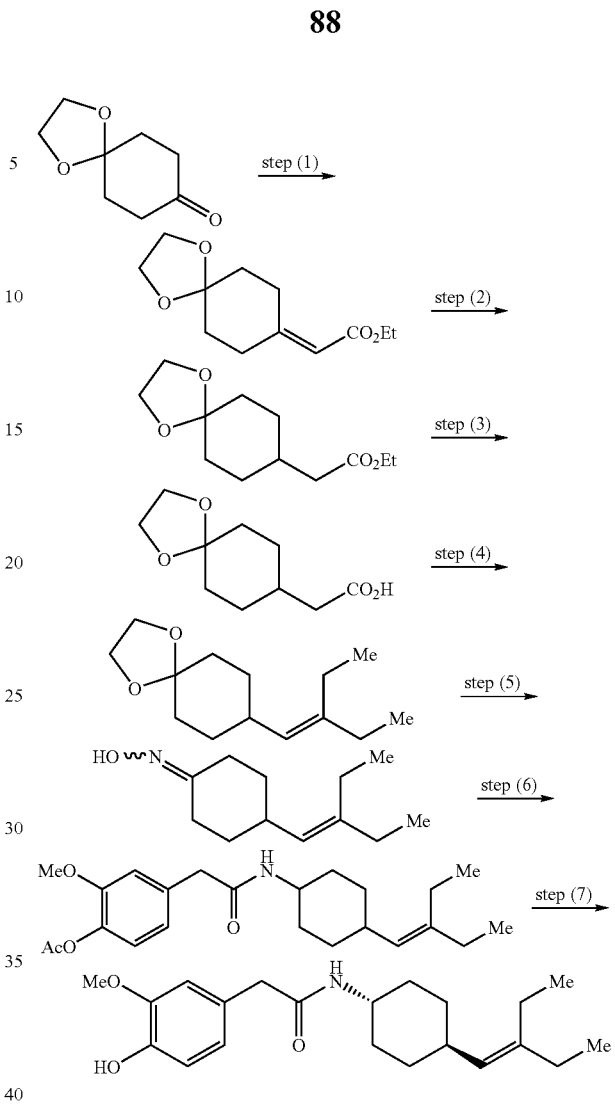

(1) To a suspension of sodium hydride (60% in oil, 9.0 g) in ethylene glycol dimethyl ether (100 ml) under ice-cooling was added dropwise a solution of ethyl diethylphosphonoacetate (45 ml) in ethylene glycol dimethyl ether (100 ml). After the reaction mixture was stirred at room temperature for 30 minutes, a solution of 1,4-cyclohexadione monoethyleneketal (5.58 g) in ethylene glycol dimethyl ether (50 ml) was added dropwise thereto, and the mixture was stirred overnight at room temperature. To the reaction mixture was added water, and the mixture was extracted with diisopropyl ether. The organic layer was washed with brine, then dried over magnesium sulfate, and the solvent was removed in vacuo. The residue was purified by a silica gel chromatography (eluent: hexane/ethyl acetate=20/1 to 4/1) to give 37 g of 8-ethoxycarbonylmethylidene-1,4-dioxaspiro[4.5]decane.

(2) The above product (1) (37 g) was dissolved in ethyl acetate (500 ml), 20% palladium hydroxide/carbon (4.0 g) was added to the mixture, and the mixture was hydrogenated at 40° C. under hydrogen atmosphere. After 6 hours, the catalyst was removed by filtration from the reaction mixture, and the filtrate was washed with brine, dried over magnesium sulfate. Then the solvent was removed in vacuo to give 36 g of ethyl 1,4-dioxaspiro[4.5]decane-8-acetate.

(3) To a solution of the above product (2) (16 g) in methanol (200 ml) was added 2M aqueous sodium hydroxide (100 ml), and the mixture was stirred overnight at room temperature.

The methanol was removed in vacuo from the reaction mixture, and then diisopropyl ether and 1M aqueous citric acid were added to the residue. The organic layer was washed with brine, dried over magnesium sulfate, and then the solvent was removed in vacuo. The resulting crude product was washed with diisopropyl ether to give 10.2 g of 1,4-dioxaspiro[4.5]decane-8-acetic acid.

(4) Under nitrogen atmosphere, a solution of the above product (3) (5.1 g) in anhydrous tetrahydrofuran (50 ml) was added to 2 M lithium diisopropylamide solution (in heptane/tetrahydrofuran/ethylbenzene, 28 ml) dropwise under ice-cooling. The mixture was stirred at room temperature for 5 hours, then cooled in an ice-water bath again. To the mixture was added dropwise a solution of 3-pentanone (2.15 g) in anhydrous tetrahydrofuran (30 ml), and then the reaction mixture was stirred overnight at room temperature. To the reaction mixture was added ice-water (250 ml), the mixture was extracted with diisopropyl ether (200 ml×2). The aqueous layer was acidified with 1M aqueous citric acid (60 ml), extracted with a mixture of chloroform and methanol (9:1, 250 ml×2). The organic layer was dried over sodium sulfate, and then the solvent was removed in vacuo. The resulting brown solid (7.2 g) was dissolved in acetonitrile (300 ml), and N,N-dimethylformamide dineopentyl acetal (11.6 g) was added thereto. The mixture was stirred at room temperature for 1 hour, and then heated under reflux overnight. The acetonitrile was evaporated under reduced pressure, and then diisopropyl ether and water were added to the residue. The mixture was separated with a separating funnel, the organic layer was washed with brine, dried over magnesium sulfate, and then the solvent was removed in vacuo. The residue was purified by a silica gel chromatography (eluent: hexane/ethyl acetate=20/1 to 10/1) to give 4.4 g of 8-(2-ethyl-1-butenyl)-1,4-dioxaspiro[4.5]decane.

(5) To the above product (4) (1.7 g) were added 2 M hydrochloric acid (10 ml) and tetrahydrofuran (30 ml), and the mixture was stirred at 45° C. for 3 hours. Diisopropyl ether and water were added to the reaction mixture, and the mixture was separated with a separating funnel. And then the organic layer was washed with brine, dried over magnesium sulfate, and the solvent was removed in vacuo. A mixture of the resulting colorless oil (1.3 g), hydroxylamine hydrochloride (1.0 g), sodium acetate (1.2 g), methanol (30 ml), and water (15 ml) was stirred at 65° C. for 4 hours. The methanol was evaporated under reduced pressure from the reaction mixture, and ethyl acetate and water were added to the residue. The mixture was separated with a separating funnel, the organic layer was washed with brine, dried over magnesium sulfate, and then the solvent was removed in vacuo. The residue was purified by a silica gel chromatography (eluent: hexane/ethyl acetate=6/1 to 4/1) to give 1.3 g of 4-(2-ethyl-1-butenyl)cyclohexanone oxime.

(6) Under nitrogen atmosphere, to a suspension of lithium aluminium hydride (0.76 g) in anhydrous tetrahydrofuran (25 ml) under ice-cooling was added dropwise a solution of the above product (5) (1.3 g) in anhydrous tetrahydrofuran (25 ml), and then the mixture was heated under reflux for 3 hours. To the reaction mixture cooled in an ice-water bath were added dropwise ethyl acetate and 1 M aqueous potassium sodium tartrate to quench an excess of lithium aluminium hydride. The mixture was filtrated through Celite. The filtrate was dried over magnesium sulfate, and then the solvent was removed in vacuo. The mixture of resulting colorless oil (1.1 g, a mixture of cis and trans forms), 4-acetoxy-3-methoxyphenyacetic acid (1.3 g), 1-ethyl-3-(3-dimethyl-aminopropyl)carbodiimide hydrochloride (1.4 g), 1-hydroxybenzotriazole (0.09 g), and dichloromethane (40 ml) was stirred overnight at room temperature. The reaction mixture was washed with water and then brine. The organic layer was dried over magnesium sulfate, and the solvent was removed in vacuo. The residue was purified by a silica gel chromatography (eluent: hexane/ethyl acetate=3/1 to 3/2) to give 1.9 g of 2-(4-acetoxy-3-methoxyphenyl)-N-[4-(2-ethyl-1-butenyl)cyclohexyl]acetamide (1.9 g, a mixture of cis and trans forms).

(7) To a solution of the above product (6) (1.9 g) in methanol (20 ml) was added 2 M aqueous sodium hydroxide, and the mixture was stirred at room temperature for 3 hours. The reaction mixture was acidified with 1 M hydrochloric acid, and the methanol was evaporated under reduced pressure. The resulting mixture was extracted with ethyl acetate, the organic layer was washed with brine, dried over magnesium sulfate, and then the solvent was removed in vacuo. The residue was purified by a silica gel chromatography (eluent: hexane/ethyl acetate=3/1 to 3/2) and then recrystallized from diisopropyl ether to give 0.3 g of the desired compound.

$^1$H-NMR (CDCl$_3$, δ): 0.93 (3H, t), 0.95 (3H, t), 1.01-1.23 (4H, m), 1.52-1.63 (2H, m), 1.87-2.12 (7H, m), 3.47 (2H, s), 3.70 (1H, m), 3.89 (3H, s), 4.84 (1H, d), 5.19 (1H, d), 5.62 (1H, s), 6.71 (1H, dd), 6.75 (1H, d), 6.88 (1H, d).

Example 91

Preparation of N-[trans-4-(cyclobutylidenemethyl)-cyclohexyl]-2-(4-hydroxy-3-methoxyphenyl)acetamide

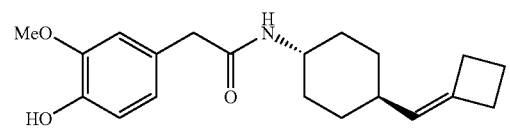

The above desired compound was prepared in a similar manner of Example 90 using cyclobutanone by which 3-pentanone of Example 90 (4) was replaced.

$^1$H-NMR (CDCl$_3$, δ): 0.93-1.23 (4H, m), 1.62 (2H, m), 1.75-1.96 (5H, m), 2.57-2.63 (4H, m), 3.47 (2H, s), 3.68 (1H, m), 3.88 (3H, s), 4.85 (1H, m), 5.20 (1H, d), 5.66 (1H, s), 6.71 (1H, dd), 6.75 (1H, d), 6.88 (1H, d).

Example 92

Preparation of N-[trans-4-(2-ethylbutyl)cyclohexyl]-2-(4-hydroxy-3-methoxyphenyl)acetamide

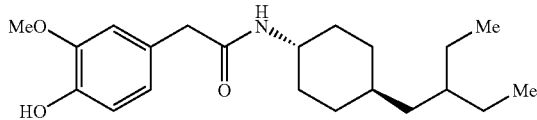

The compound (0.07 g) of Example 90 was dissolved in ethanol (10 ml), 10% palladium/carbon (10 mg) was added to the solution, and the mixture was hydrogenated at room temperature. After 3 hours, the catalyst was removed by filtration from the reaction mixture, and the solvent was evaporated under reduced pressure from the filtrate. The residue was crystallized from diisopropyl ether to give 46 mg of the desired compound as a crystal.

$^1$H-NMR (CDCl$_3$, δ): 0.80 (6H, t), 0.92-1.08 (6H, m), 1.18-1.27 (6H, m), 1.71 (2H, m), 1.87 (2H, m), 3.47 (2H, s), 3.69 (1H, m), 3.88 (3H, s), 5.20 (1H, d), 5.64 (1H, s), 6.71 (1H, dd), 6.75 (1H, d), 6.88 (1H, d).

Example 93

Preparation of N-[trans-4-(cyclobutylmethyl)cyclohexyl]-2-(4-hydroxy-3-methoxyphenyl)acetamide

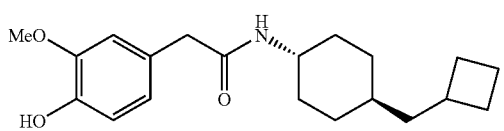

The above desired compound was prepared in a similar manner of Example 92 using the compound of Example 91 by which the compound of Example 90 in Example 92 was replaced.

$^1$H-NMR (CDCl$_3$, δ): 0.87-1.15 (5H, m), 1.26 (2H, t), 1.46-2.04 (10H, m), 2.30 (1H, m), 3.46 (2H, s), 3.66 (1H, m), 3.88 (3H, s), 5.19 (1H, d), 5.66 (1H, s), 6.71 (1H, dd), 6.75 (1H, d), 6.88 (1H, d).

Example 94

Preparation of N-{trans-4-[(Z)-2-butenyl]cyclohexyl}-2-(4-hydroxy-3-methoxyphenyl)acetamide

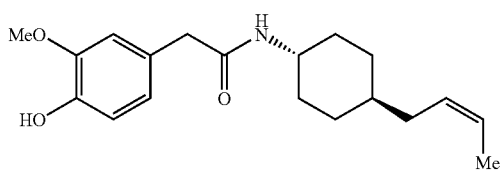

The above compound was prepared by the following procedure.

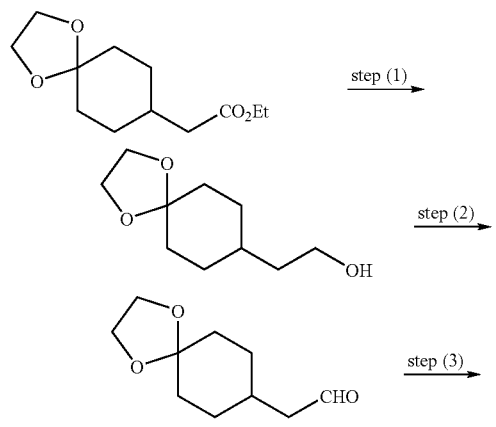

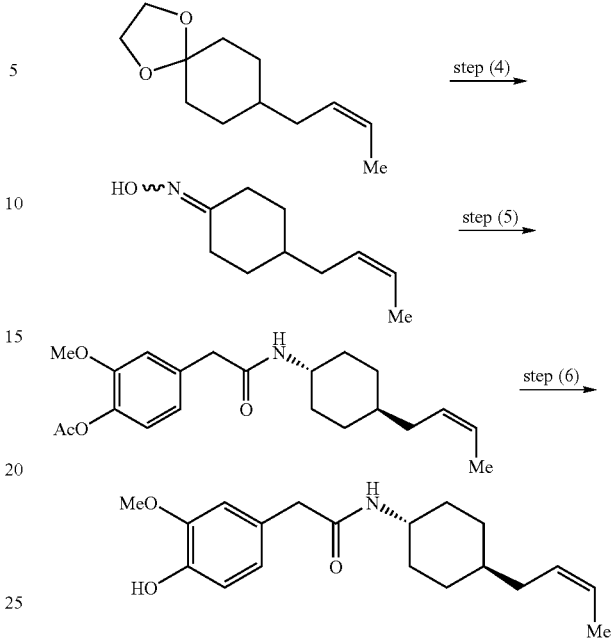

(1) To a mixture of lithium aluminium hydride (831 mg) and anhydrous tetrahydrofuran (70 ml) at 0° C. was added a solution of ethyl 1,4-dioxaspiro[4.5]decane-8-acetate of Example 90 (2) (5.0 g) in anhydrous tetrahydrofuran (30 ml). The mixture was gradually warmed to about 25° C., stirred for 3 hours, and then sodium fluoride, water and dichloromethane were added to the reaction mixture. The precipitate was filtrated off with Celite, the filtrated organic layer was dried over sodium sulfate. The solvent was removed in vacuo from the organic layer to give 4.18 g of 8-(2-hydroxyethyl)-1,4-dioxaspiro[4.5]decane.

(2) To a mixture of the above product (1) (4.18 g) and dimethyl sulfoxide (150 ml) at 25° C. was added triethylamine (31.2 ml) and sulfatrioxide-pyridine complex (14.3 g), and the mixture was stirred for 1 hour. To the reaction mixture was added saturated aqueous ammonium chloride, and the resulting mixture was extracted with chloroform. The organic layer was washed with brine, dried over sodium sulfate, and then the solvent was removed in vacuo. The residue was purified by a silica gel chromatography (eluent: gradient from 100% hexane/0% ethyl acetate to 0% hexane/100% ethyl acetate) to give 2.24 g of 1,4-dioxaspiro[4.5]decane-8-acetaldehyde.

(3) To a mixture of potassium t-butoxide (2.73 g) and anhydrous tetrahydrofuran (30 ml) at room temperature was added ethyltriphenylphosphonium bromide (9.03 g). The reaction mixture was stirred for 10 minutes, then a solution of the above product (2) (2.24 g) in anhydrous tetrahydrofuran (20 ml) was added thereto, and the mixture was stirred overnight. To the reaction mixture was added saturated aqueous ammonium chloride, and the mixture was extracted with ethyl acetate. The organic layer was washed with brine, dried over sodium sulfate, and then the solvent was removed in vacuo. After diethyl ether was added to the residue, the precipitate was filtered off and then the filtrate was concentrated under reduced pressure. The residue was purified by a silica gel chromatography (eluent: gradient from 100% hexane/0% ethyl acetate to 0% hexane/100% ethyl acetate) to give 2.27 g of 8-[(Z)-2-butenyl]-1,4-dioxaspiro[4.5]decane.

(4) To the above product (3) (2.27 g) were added 2 M hydrochloric acid (23 ml) and tetrahydrofuran (50 ml), and the mixture was stirred at 45° C. for 5 hours. To the reaction mixture were added diisopropyl ether and water. The mixture was separated with a separating funnel, the organic layer was washed with brine, dried over magnesium sulfate. The solvent was removed in vacuo, and hydroxylamine hydrochloride (1.61 g), sodium acetate (1.9 g), methanol (30 ml), and water (15 ml) were added to the residue, and then the reaction mixture was stirred at 65° C. for 3 hours. The methanol was evaporated under reduced pressure, and ethyl acetate and water were added to the residue. The mixture was separated with a separating funnel, the organic layer was washed with brine, dried over magnesium sulfate, and then the solvent was removed in vacuo. The residue was purified by a silica gel chromatography (eluent: hexane/ethyl acetate=6/1 to 4/1) to give 1.73 g of 4-[(Z)-2-butenyl]cyclohexanone oxime.

(5) Under nitrogen atmosphere, to a suspension of lithium aluminium hydride (1.18 g) in anhydrous tetrahydrofuran (30 ml) under ice-cooling was added dropwise a solution of the above product (4) (1.73 g) in anhydrous tetrahydrofuran (30 ml), and then the mixture was heated under reflux for 3 hours. The reaction mixture was cooled in an ice-water bath, and ethyl acetate and 1 M aqueous potassium sodium tartrate were added thereto dropwise to quench an excess of lithium aluminium hydride. The mixture was filtrated through Celite. The filtrate was dried over magnesium sulfate, and then the solvent was removed in vacuo. A mixture of the resulting colorless oil (1.0 g), 4-acetoxy-3-methoxyphenyacetic acid (1.22 g), benzotriazol-1-yloxy-tris(pyrrolidino)phosphonium hexafluorophosphate (2.83 g), triethylamine (1.52 ml), and dichloromethane (15 ml) was stirred overnight at room temperature. The reaction mixture was washed with water and then brine. The organic layer was dried over magnesium sulfate, and the solvent was removed in vacuo. The residue was purified by a silica gel chromatography (eluent: hexane/ethyl acetate=3/1 to 3/2) to give 405 mg of 2-(4-acetoxy-3-methoxyphenyl)-N-{trans-4-[(Z)-2-butenyl]cyclohexyl}acetamide as a colorless amorphous.

(6) To a solution of the above produce (5) (400 mg) in methanol (20 ml) was added 2 M aqueous sodium hydroxide (6 ml), and the mixture was stirred at room temperature for 3 hours. The reaction mixture was acidified with 1 M hydrochloric acid, and the methanol was evaporated under reduced pressure from the mixture. The resulting mixture was extracted with ethyl acetate, the organic layer was washed with brine, dried over magnesium sulfate, and then the solvent was removed in vacuo. The residue was purified by a silica gel chromatography (eluent: hexane/ethyl acetate=3/1 to 3/2) to give 152 mg of the desired compound.

$^1$H-NMR (CDCl$_3$, δ): 0.92-1.25 (4H, m), 1.59 (3H, d), 1.70-1.99 (7H, m), 3.47 (2H, s), 3.68 (1H, m), 3.88 (3H, s), 5.20 (1H, d), 5.35 (1H, dt), 5.46 (1H, dq), 5.63 (1H, brs), 6.71 (1H, dd), 6.75 (1H, d), 6.89 (1H, d).

Example 95

Preparation of 2-(4-hydroxy-3-methoxyphenyl)-N-[cis-4-(2-methyl-1-propenyl)cyclohexyl]acetamide

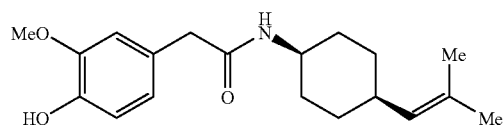

The above compound was prepared by the following procedure.

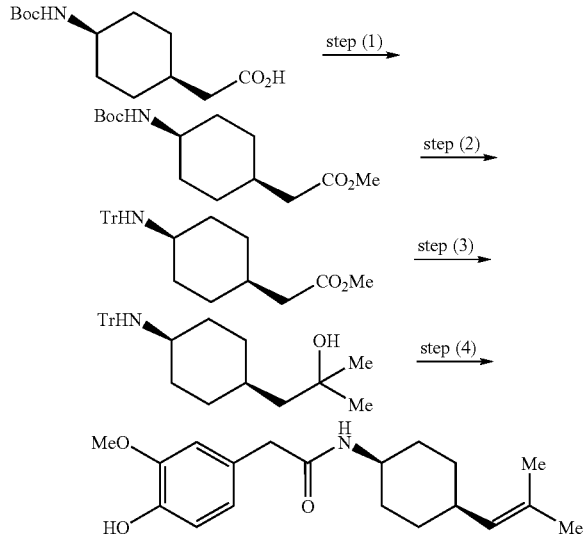

(1) Under nitrogen atmosphere, to a solution of cis-4-(t-butoxycarbonylaminocyclohexyl)acetic acid (2.0 g) in methanol (10 ml) and toluene (40 ml) was added 2 M trimethylsilyl diazomethane solution (in diethyl ether, 5.0 ml) dropwise. The reaction mixture was stirred at room temperature for 3 hours, and then ethyl acetate and brine were added to the reaction mixture. The mixture was separated with a separating funnel, the organic layer was dried over magnesium sulfate, and then the solvent was removed in vacuo to give 2.2 g of methyl cis-4-(t-butoxycarbonylaminocyclohexyl)acetate.

(2) To the above product (1) (2.2 g) was added 4 M hydrogen chloride solution (in ethyl acetate, 15 ml), and the mixture was stirred overnight at room temperature. The reaction mixture was concentrated under reduced pressure, and then chloroform and 1 M aqueous potassium carbonate were added to the residue. The mixture was separated with a separating funnel, the organic layer was washed with brine, dried over magnesium sulfate, and then the solvent was removed in vacuo. To a solution of the resulting oil (1.2 g) and triethylamine (1.2 ml) in dichloromethane (30 ml) was added dropwise a solution of triphenylmethyl chloride (2.0 g) in dichloromethane (10 ml), and the mixture was stirred overnight at room temperature. The reaction mixture was washed with water and then brine. The organic layer was dried over magnesium sulfate, and the solvent was removed in vacuo. The residue was purified by a silica gel chromatography (eluent:

hexane/ethyl acetate=20/1) to give 2.6 g of methyl cis-4-(triphenylmethyl-aminocyclohexane)acetate.

(3) Under nitrogen atmosphere, to a solution of the above product (2) (2.6 g) in anhydrous tetrahydrofuran (75 ml) under ice-cooling was added dropwise 0.96 M methyl magnesium bromide solution (in tetrahydrofuran, 26 ml), and then the mixture was stirred overnight at room temperature. The reaction mixture was cooled in an ice-water bath, and saturated aqueous ammonium chloride was added dropwise thereto. Ethyl acetate and water were added thereto and the mixture was separated with a separating funnel. The organic layer was washed with saturated aqueous sodium hydrogen carbonate and then brine. The organic layer was dried over magnesium sulfate, and the solvent was removed in vacuo. The residue was purified by a silica gel chromatography (eluent: hexane/ethyl acetate=4/1 to 3/1) to give 1.7 g of 2-(4-triphenylmethylaminocyclohexyl)-propan-2-ol.

(4) To a solution of the above product (3) (0.82 g) in toluene (30 ml) was added p-toluenesulfonic acid monohydrate (0.76 g), and the mixture was stirred at 65° C. for 3 hours. The reaction mixture was cooled to ambient temperature and washed with saturated aqueous sodium hydrogen carbonate and then brine. The organic layer was dried over magnesium sulfate, and the solvent was removed in vacuo. A mixture of the resulting product, 4-hydroxy-3-methoxyphenyacetic acid (0.27 g), 1-ethyl-3-(3-dimethylaminopropyl)carbodiimide hydrochloride (0.38 g), 1-hydroxybenzotriazole (0.03 g) and dichloromethane (20 ml) was stirred overnight at room temperature. The reaction mixture was washed with water and then brine. The organic layer was dried over magnesium sulfate, and the solvent was removed in vacuo. The residue was purified by a silica gel chromatography (eluent: hexane/ethyl acetate=2/1) and then recrystallized from hexane-ethyl acetate to give 0.05 g of the desired compound.

$^1$H-NMR (CDCl$_3$, δ): 1.04 (2H, m), 1.44-1.62 (6H, m), 1.59 (3H, s), 1.67 (3H, s), 2.25 (1H, m), 3.50 (2H, s), 3.90 (3H, s), 3.96 (1H, m), 4.95 (1H, d), 5.51 (1H, br), 5.63 (1H, s), 6.75 (1H, dd), 6.78 (1H, d), 6.92 (1H, d).

Example 96

Preparation of 2-(4-hydroxy-3-methoxyphenyl)-N-[cis-4-(2-methylpropyl)cyclohexyl]acetamide

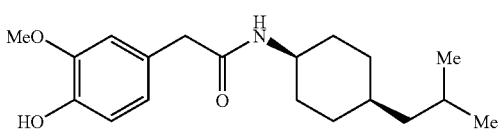

The compound (0.3 g) of Example 95 was dissolved in ethanol (15 ml), platinum oxide (50 mg) was added to the solution, and the mixture was hydrogenated at room temperature. After 3 hours, the catalyst was removed by filtration from the reaction mixture and then the solvent was evaporated under reduced pressure. The residue was crystallized from diisopropyl ether to give 0.21 g of the desired compound.

$^1$H-NMR (CDCl$_3$, δ): 0.76-0.90 (2H, m), 0.83 (6H, d), 0.99 (2H, t), 1.38 (1H, m), 1.45-1.65 (7H, m), 3.49 (2H, s), 3.89 (3H, s), 3.98 (1H, m), 5.52 (1H, br), 5.67 (1H, s), 6.74 (1H, dd), 6.77 (1H, d), 6.91 (1H, d).

Example 97

Preparation of N-{cis-4-[(E)-1-ethyl-1-propenyl]-cyclohexyl}-2-(4-hydroxy-3-methoxyphenyl)acetamide

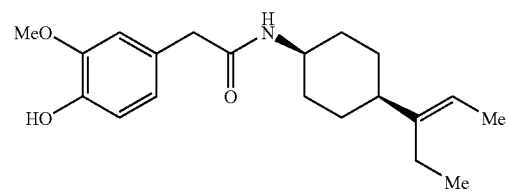

(1) 3-(4-triphenylmethylaminocyclohexyl)pentan-3-ol (2.5 g) prepared in Example 88 (2) was dissolved in ethanol (100 ml), 20% palladium hydroxide/carbon (1.0 g) was added to the solution, and the mixture was hydrogenated at 50° C. After 18 hours, the catalyst was filtrated off and then the solvent was evaporated under reduced pressure from the filtrate. A mixture of the resulting product, 4-acetoxy-3-methoxyphenyacetic acid (1.1 g), 1-ethyl-3-(3-dimethyl-aminopropyl)carbodiimide hydrochloride (1.2 g), 1-hydroxybenzotriazole (0.08 g), and dichloromethane (20 ml) was stirred overnight at room temperature. The reaction mixture was washed with water and then brine. The organic layer was dried over magnesium sulfate, and the solvent was removed in vacuo. The residue was purified by a silica gel chromatography (eluent: hexane/ethyl acetate=3/2 to ⅓) to give 1.6 g of 2-(4-acetoxy-3-methoxyphenyl)-N-[cis-4-(1-ethyl-1-hydroxypropyl)cyclohexyl]acetamide.

(2) To a solution of the above product (1) (1.5 g) in toluene (30 ml) was added p-toluenesulfonic acid monohydrate (0.75 g), and the mixture was stirred at 60° C. for 2 hours. After the reaction mixture was cooled to ambient temperature, saturated aqueous sodium hydrogen carbonate was added thereto. The mixture was separated with a separating funnel, the organic layer was washed with brine, dried over magnesium sulfate, and the solvent was removed in vacuo. The residue was purified by a silica gel chromatography (eluent: hexane/ethyl acetate=2/1), recrystallized from hexane-ethyl acetate and further recrystallized from aqueous isopropanol to give 0.09 g of the desired compound.

$^1$H-NMR (CDCl$_3$, δ): 0.90 (3H, t), 0.96 (2H, m), 1.42-1.97 (7H, m), 1.57 (3H, d), 1.92 (2H, q), 3.51 (2H, s), 3.89 (3H, s), 4.05 (1H, m), 5.03 (1H, q), 5.57-5.70 (2H, m), 6.75-6.78 (2H, m), 6.92 (1H, d).

Example 98

Preparation of 2-(4-hydroxy-3-methoxyphenyl)-N-[cis-4-(3-pentyl)cyclohexyl]acetamide

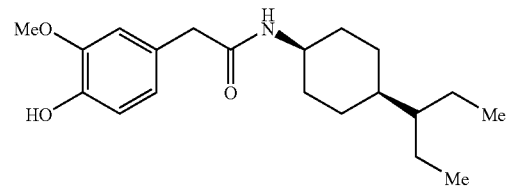

The compound (0.07 g) in Example 97 was dissolved in ethanol (10 ml), platinum oxide (15 mg) was added to the solution, and the mixture was hydrogenated at room temperature. After 18 hours, the catalyst was filtrated off and then the solvent was evaporated under reduced pressure from the filtrate. The residue was crystallized from diisopropyl ether to give 0.03 g of the desired compound.

$^1$H-NMR (CDCl$_3$, δ): 0.82 (6H, t), 0.80-0.90 (3H, m), 1.04-1.22 (4H, m), 1.26-1.72 (7H, m), 3.51 (2H, s), 3.89 (3H, s), 4.04 (1H, m), 5.56 (1H, br), 5.64 (1H, s), 6.74-6.77 (2H, m), 6.92 (1H, d).

Example 99

Preparation of N-[trans-4-(4-fluorobutyl)cyclohexyl]-2-(4-hydroxy-3-methoxyphenyl)acetamide

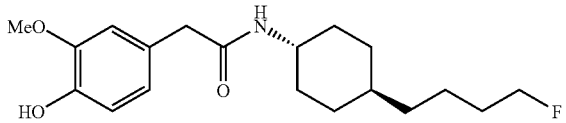

(1) To a mixture of potassium t-butoxide (0.54 g) and tetrahydrofuran (10 ml) at room temperature was added 4-fluorobutyltriphenylphosphonium bromide (2.0 g). After stirring for 30 minutes, a solution of t-butyl 4-oxocyclohexylcarbamate (0.50 g) in tetrahydrofuran (5 ml), and the mixture was stirred at room temperature. After 10 hours, saturated aqueous ammonium chloride was added to the reaction mixture, and the mixture was extracted with ethyl acetate. The organic layer was washed with brine, and then dried over sodium sulfate, and the solvent was evaporated under reduced pressure from the organic layer. The residue was suspended in hexane and the suspension was stirred at 40° C. After 20 minutes, the precipitate was filtrated off, and the filtrate was concentrated under reduced pressure to give 400 mg of t-butyl [4-(4-fluorobutylidene)cyclohexyl]-carbamate.

(2) To a solution of the above product (1) (400 mg) in ethyl acetate (5 ml) was added 4 mol/l hydrogen chloride solution (in ethyl acetate, 2 ml), and the mixture was stirred. After 20 minutes, the precipitated crystal was collected by filtration to give 225 mg of 4-(4-fluorobutylidene)cyclohexylamine hydrochloride.

(3) The above product (2) (225 mg), 4-acetoxy-3-methoxyphenyacetic acid (240 mg), 1-ethyl-3-(3-dimethylaminopropyl)carbodiimide hydrochloride (220 mg) and triethylamine (0.2 ml) were dissolved in ethyl acetate (10 ml), and the mixture was stirred at room temperature. After 10 hours, the reaction mixture was washed with water (10 ml), the organic layer was dried over sodium sulfate, and then the solvent was removed from the organic layer in vacuo. The residue was purified by a silica gel chromatography (eluent: gradient from 100% hexane/0% ethyl acetate to 0% hexane/100% ethyl acetate) to give 370 mg of 2-(4-acetoxy-3-methoxyphenyl)-N-[4-(4-fluorobutylidene)-cyclohexyl]acetamide.

(4) The above product (3) (370 mg) was dissolved in a mixture of ethanol (5 ml) and ethyl acetate (5 ml), 10% palladium/carbon (50 mg) was added to the solution, and the mixture was hydrogenated at 25° C. The catalyst was filtrated off, and the solvent was evaporated under reduced pressure from the filtrate to give 350 mg of a mixture of 2-(4-acetoxy-3-methoxyphenyl)-N-[trans-4-(4-fluorobutyl)cyclohexyl]acetamide and 2-(4-acetoxy-3-methoxyphenyl)-N-[cis-4-(4-fluorobutyl)cyclohexyl]acetamide (trans product:cis product ≈7:1).

(5) To a solution of the above product (4) (350 mg) in methanol was added 2 mol/l aqueous sodium hydroxide (2 ml), and the mixture was stirred at 40° C. After 30 minutes, the methanol was evaporated under reduced pressure. To the residue was added 2 mol/l hydrochloric acid (2.1 ml) and the mixture was extracted with ethyl acetate. The organic layer was washed with brine, then dried over sodium sulfate, and the solvent was removed in vacuo from the organic layer. The residue was purified by a silica gel chromatography (eluent: gradient from 100% hexane/0% ethyl acetate to 0% hexane/ 100% ethyl acetate) to give a crude crystal and then the crystal was recrystallized from hexane/ethyl acetate (1/1, 2 ml) to give 85 mg of the desired compound.

$^1$H-NMR (CDCl$_3$, δ): 0.88-1.05 (4H, m), 1.08-1.25 (3H, m), 1.30-1.45 (2H, m), 1.48-1.80 (4H, m), 1.83-1.98 (2H, m), 3.47 (2H, s), 3.69 (1H, m), 3.89 (3H, s), 4.34 (1H, t), 4.50 (1H, t), 5.18 (1H, d), 5.60 (1H, s), 6.71 (1H, dd), 6.75 (1H, d), 6.88 (1H, d).

Example 100

Preparation of N-(trans-4-cyclopropylmethylcyclohexyl)-2-(4-hydroxy-3-methoxyphenyl)acetamide

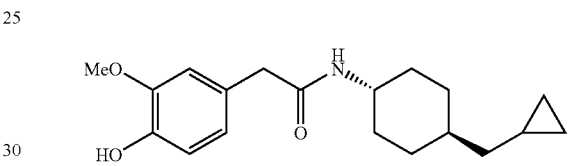

(1) To a mixture of sodium hydride (1.06 g) and anhydrous tetrahydrofuran (50 ml) was added cyclopropyl-triphenylphosphonium bromide (10.13 g), the mixture was heated under reflux for 1 hour. The reaction mixture was cooled to ambient temperature, and then thereto was added a mixture of t-butyl trans-4-formylcyclohexylcarbamate (3.00 g), tris[2-(2-methoxyethoxy)ethyl]amine (427 mg) and anhydrous tetrahydrofuran (15 ml). The resulting mixture was heated under reflux for 1 hour. The reaction mixture was cooled to ambient temperature, and then saturated aqueous ammonium chloride was added to the reaction mixture. The reaction mixture was extracted with ethyl acetate, the organic layer was washed with brine, dried over sodium sulfate, and then the solvent was removed in vacuo. The residue was purified by a silica gel chromatography (eluent: gradient from 100% hexane/0% ethyl acetate to 0% hexane/100% ethyl acetate) to give 1.43 g of t-butyl trans-4-cyclopropylidenemethylcyclohexylcarbamate.

(2) To a solution of the above product (1) (1.42 g) in ethyl acetate (20 ml) was added p-toluenesulfonic acid monohydrate (1.07 g), and the mixture was stirred at 60° C. for 1 hour. To the reaction mixture was added hexane (60 ml), and the precipitated crystal was collected by filtration to give 590 mg of trans-4-cyclopropylidene-methylcyclohexylamine p-toluenesulfonate.

(3) To a mixture of the above product (2) (590 mg), 4-hydroxy-3-methoxyphenyacetic acid (333 mg), and benzotriazol-1-yloxy-tris(pyrrolidino)phosphonium hexafluorophosphate (952 mg) in dichloromethane (20 ml) under ice-cooling was added triethylamine (0.77 ml). The reaction mixture was stirred at room temperature for 1 hour, and then washed with saturated aqueous ammonium chloride and then brine. The organic layer was dried over sodium sulfate, and then the solvent was removed in vacuo. The residue was purified by a silica gel chromatography (eluent: gradient from 100% hexane/0% ethyl acetate to 0% hexane/100% ethyl acetate) to give a crude crystal and then the crystal was recrystallized from hexane/ethyl acetate (4/1) to 310 mg of 2-(4-hydroxy-3-methoxyphenyl)-N-(trans-4-cyclopropylidenemethylcyclohexyl)acetamide.

(4) The above product (3) (145 mg) was dissolved in ethanol (7 ml), 5% palladium/carbon (20 mg) was added to the solution, and the mixture was hydrogenated at room temperature. After 3 hours, the catalyst was filtrated off, and the solvent was evaporated under reduced pressure from the filtrate. The residue was recrystallized from hexane/ethyl acetate (4/1) to give 50 mg of the desired compound.

$^1$H-NMR (CDCl$_3$, δ): −0.05-0.02 (2H, d), 0.35-0.42 (2H, m), 0.55-1.65 (1H, m), 0.90-1.29 (9H, m), 1.76-1.93 (2H, m), 3.47 (2H, s), 3.61-3.75 (1H, m), 3.89 (3H, s), 5.18 (1H, d), 5.57 (1H, s), 6.71 (1H, dd), 6.76 (1H, d), 6.88 (1H, d).

Examples 101-103

Instead of 1-phenyl-5-propylsulfonyl-1H-tetrazole of Example 52, various 5-alkylsulfonyl-1-phenyl-1H-tetrazoles are treated in a similar manner of Example 52 to give the compounds listed in Table 12.

$^1$H-NMR (CDCl$_3$, δ): 0.84 (9H, m), 0.91-1.19 (7H, m), 1.45-1.95 (6H, m), 3.46 (2H, s), 3.60-3.79 (1H, m), 3.89 (3H, s), 5.18 (1H, d), 5.59 (1H, s), 6.71 (1H, dd), 6.75 (1H, d), 6.88 (1H, d).

Example 105

Preparation of 2-(4-hydroxy-3-methoxyphenyl)-N-(spiro[5.5]undec-3-yl)acetamide

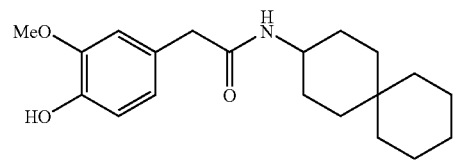

TABLE 12

| | Structure | $^1$HNMR (CDCl$_3$, δ) |
|---|---|---|
| Example 101 | MeO, HO, N, Me, Me, Me | 0.90-1.23 (6H, m), 0.96 (9H, s), 1.52-1.96 (5H, m), 3.47 (2H, s), 3.62-3.76 (1H, m), 3.89 (1H, s), 5.18 (1H, dd), 5.19 (1H, d), 5.38 (1H, d), 5.59 (1H, s), 6.71 (1H, dd), 6.75 (1H, d), 6.88 (1H, d). |
| Example 102 | MeO, HO, N, F, F, F | 0.95-1.10 (2H, m), 1.12-1.30 (2H, m), 1.70-1.80 (2H, m), 1.82-1.98 (3H, m), 2.74 (2H, m), 3.47 (2H, s), 3.70 (1H, m), 3.89 (3H, s), 5.20 (1H, d), 5.26-5.38 (1H, m), 5.54-5.66 (2H, m), 6.68-6.76 (2H, m), 6.88 (1H, d). |
| Example 103 | MeO, HO, N, F | 0.92-1.08 (2H, m), 1.10-1.28 (2H, m), 1.66-1.97 (5H, m), 2.32 (1H, dd), 2.41 (1H, dd), 3.47 (2H, s), 3.69 (1H, m), 3.89 (3H, s), 4.33 (1H, t), 4.49 (1H, t), 5.19 (1H, d), 5.28-5.50 (2H, m), 5.62 (1H, s), 6.71 (1H, dd), 6.75 (1H, d), 6.88 (1H, d). |

Example 104

Preparation of N-[trans-4-(3,3-dimethylbutyl)cyclohexyl]-2-(4-hydroxy-3-methoxyphenyl)acetamide

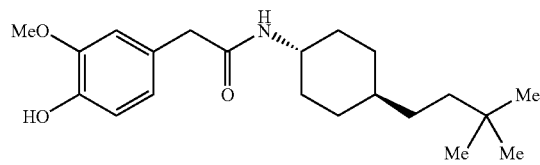

The above desired compound was prepared in a similar manner of Example 59 using the compound of Example 101 (DSR1379) by which the compound of Example 57 in Example 59 was replaced.

(1) Cyclohexanecarboxyaldehyde (23.2 g) and pyrrolidine (14.5 g) were dissolved in toluene (200 ml), and the mixture was heated under reflux using a Dean-Stark distillation apparatus. After 12 hours, the solvent was removed. The residue was distilled under reduced pressure (60° C., 1 mmHg) to give 22.6 g of 1-(cyclohexylidene-methyl)pyrrolidine.

(2) To a solution of the above product (1) (22.6 g) in toluene (100 ml) was added methylvinyl ketone (9.6 g), and the mixture was stirred at room temperature. After 3 hours, to the reaction mixture were added sodium acetate (10 g), acetic acid (40 ml) and water (40 ml), and the mixture was heated under reflux. After 4 hours, the reaction mixture was cooled to room temperature and then ethyl acetate (100 ml) was added thereto. The mixture was washed with water (100 ml), 2 mol/l hydrochloric acid (50 ml) and then brine (100 ml), and the organic layer was dried over sodium sulfate, and the solvent was removed in vacuo. The residue was distilled under reduced pressure (95° C., 1 mmHg) to give 4.3 g of spiro[5.5]undecen-3-one.

(3) Then the desired compound were prepared in a similar manner of Example 9 using the above product (2) instead of 4,4-dipropyl-2-cyclohexenone of Example 9.

$^1$H-NMR (CDCl$_3$, δ): 1.10-1.70 (18H, m), 3.47 (2H, s), 3.72 (1H, m), 3.89 (3H, s), 5.24 (1H, m), 5.60 (1H, s), 6.72 (1H, dd), 6.76 (1H, d), 6.89 (1H, d).

Examples 106-107

Instead of cyclohexanecarboxyaldehyde of Example 105, various aldehydes are treated in a similar manner of Example 105 to give the compounds listed in Table 13.

TABLE 13

| | Structure | $^1$H-NMR (CDCl$_3$, δ) |
|---|---|---|
| Example 106 | ![structure] | 0.69 (3H, t), 0.73 (3H, t), 1.12-1.30 (8H, m), 1.33-1.43 (2H, m), 1.57-1.72 (2H, m), 3.47 (2H, s), 3.70 (1H, m), 3.89 (3H, s), 5.20-5.33 (1H, m), 5.61 (1H, s), 6.72 (1H, dd), 6.76 (1H, d), 6.89 (1H, d). |
| Example 107 | ![structure] | 0.65-0.80 (3H, m), 0.85-0.93 (3H, m), 1.00-1.75 (16H, m), 3.47 (2H, s), 3.70 (1H, m), 3.89 (3H, s), 5.27 (1H, m), 5.60 (1H, s), 6.68-6.78 (2H, m), 6.89 (1H, d). |

Comparative Example 1

Preparation of 2-(4-hydroxy-3-methoxyphenyl)-N-(4-methyl-cyclohexyl)acetamide

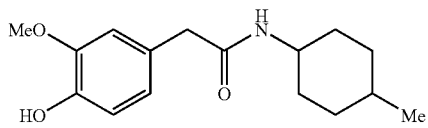

The above compound was prepared in a similar manner of Example 9.

Comparative Example 2

Preparation of N-cyclohexyl-2-(4-hydroxy-3-methoxyphenyl)-acetamide

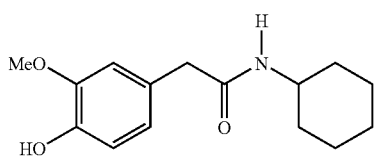

The above compound was prepared in a similar manner of Example 1 (3).

Experiment

The pharmacological activities of the present compounds are examined by the following pharmacological experiments using the representative compounds of the invention, but the present invention should not be construed to be limited to the pharmacological experiments.

Experiment 1: Pain Test by Plantar Thermal Stimuli (Plantar Test)

In the present experiment, the analgesic effect of the compounds of the invention was evaluated by the measurements of withdrawal latency to noxious thermal stimuli, according to the methods of Hargreaves, et al., [Pain, 32, 77-88 (1988)] and Field, et al., [J. Pharmacol. Exp. Ther., 282, 1242-1246 (1997)].

In detail, the experiment was carried out using male Std: Wistar rats (4 rats/group; body weight, 170-220 g) and a plantar test device (Model 7370, Ugo Basile) with infrared beam as a heat source. The rat was put into an experimental cage that is an acrylic box whose bottom is made of glass and was habituated therein. Then, the infrared beam was radiated to the plantar surface of right hind-paw thereof through the floor glass, and the withdrawal latency was measured every 5 minutes, 3 times. The intension of the infrared beam was adjusted so that the pre-drug administration latency was about 10 seconds. The cut-off time was set at 25 seconds in order to prevent a paw burn. The average of the latencies was calculated, and then it was defined as the value of the pre-drug administration latency of the test compound.

Next day, 50 μl of each solution of the test compounds [the compounds of the invention, the compounds of the comparative Examples and capsaicin (Sigma, U.S.A.)] or 50 μl of vehicle solvent (reference) was given to a right hind-paw of the rat by intraplantar injection (i. pl.) using a micro-syringe. The test compound was dissolved in a saline solution containing 10% Tween 80 (Sigma, U.S.A) and 10% ethanol to give a 0.03% (W/V) solution. The saline solution containing 10% Tween 80 and 10% ethanol was used as reference. Four hours after i.pl. administration of each the test compound or the reference to the rats, the experiment mentioned above was carried out, and then the post-drug administration latency was measured. The analgesic effects thereof were calculated with the following formula, which was known as a percent maximum possible effect (% MPE).

% MPE=[(the value of post-drug latency−the value of pre-drug latency)/(25*−the value of pre-drug latency)]×100 *: cut-off time The results are shown in the following Table 14.

TABLE 14

| Example | % MPE | Example | % MPE | Example | % MPE | Example | % MPE |
|---|---|---|---|---|---|---|---|
| 1 | 69.9 | 29 | 45.8 | 57 | 54.2 | 85 | 49.3 |
| 2 | 81.4 | 30 | 71.3 | 58 | 48.6 | 86 | 68.6 |
| 3 | 89.9 | 31 | 54.3 | 59 | 74.7 | 87 | 80.1 |
| 4 | 56.6 | 32 | 85.5 | 60 | 91.4 | 88 | 95.5 |
| 5 | 59.2 | 33 | 73.3 | 61 | 49.4 | 89 | 100 |
| 6 | 82.6 | 34 | 97.8 | 62 | 86.3 | 90 | — |
| 7 | 78.6 | 35 | 42.8 | 63 | 96.4 | 91 | 74.2 |
| 8 | 88.4 | 36 | 50.5 | 64 | 71.1 | 92 | — |
| 9 | 64.7 | 37 | 49.9 | 65 | 100 | 93 | 69.7 |
| 10 | 89.4 | 38 | 57.6 | 66 | 88.0 | 94 | 69.1 |
| 11 | 95.3 | 39 | 39.6 | 67 | 55.6 | 95 | 88.8 |
| 12 | 97.0 | 40 | 48.3 | 68 | 81.6 | 96 | 80.4 |
| 13 | 91.7 | 41 | 45.8 | 69 | 79.9 | 97 | 63.8 |
| 14 | 100 | 42 | 85 | 70 | 92.6 | 98 | 74.6 |
| 15 | 94.4 | 43 | 88.5 | 71 | 87.9 | 99 | 55.8 |
| 16 | 94.1 | 44 | 58.3 | 72 | 75.4 | 100 | 44.5 |
| 17 | 74.9 | 45 | 73.9 | 73 | 74.1 | 101 | — |
| 18 | 80.5 | 46 | 91.4 | 74 | 57.1 | 102 | 56.6 |
| 19 | 35.9 | 47 | 69.0 | 75 | 74.4 | 103 | 36.7 |
| 20 | 53.8 | 48 | 79.6 | 76 | 71.0 | 104 | — |
| 21 | 50.3 | 49 | 97.0 | 77 | 78.6 | 105 | 63.4 |
| 22 | 54.7 | 50 | 48.2 | 78 | 82.8 | 106 | 51.5 |
| 23 | 77.9 | 51 | 96.4 | 79 | 33.6 | 107 | 85.2 |
| 24 | 72.4 | 52 | 91.5 | 80 | 37.0 |  |  |
| 25 | 98.3 | 53 | 47.1 | 81 | 94.4 | Reference (vehicle solvent) | 5.4 |
| 26 | 96.3 | 54 | 82.5 | 82 | 68.4 | Comparative Example 1 | 23.3 |
| 27 | 89.5 | 55 | 55.4 | 83 | 77.4 | Comparative Example 2 | 30.6 |
| 28 | 87.1 | 56 | 70.2 | 84 | 76.9 | Capsaicin | 39.2 |

—: No test

As shown in Table 14, each of the compounds of the invention, when administered i.pl., exhibited the same or more potent analgesic effect as compared with that of capsaicin.

Experiment 2: Study for Irritancy (Eye-Wiping Test)

In this experiment, we examined the irritancy of the compounds of the invention. The experiment was carried out according to Jancso, et al., [Acta. Physiol. Acad. Sci. Hung., 19, 113-131 (1961)] and Szallasi, et al., [Brit. J. Pharmacol., 119, 283-290 (1996)]. In more detail, the compounds of the invention were dissolved in a physiological saline solution containing 5% Tween 80 and 5% ethanol to prepare each 2 different concentrations (2 concentrations: 10 and 30 μg/ml). One drop of each the solution was dropped into an eye of male Std:ddY mice (5 rats/group; body weight, 20-30 g). The protective wiping behaviors with its front paws were counted for every one minute from 0 to 5 minutes after the administration. Then, the average counts in each one minute were calculated, and the maximum value among the averages was defined as the representative value. Using the saline solution containing % Tween 80 and 5% ethanol as a vehicle solvent, the test mentioned above was also carried out.

The results are shown in Table 15.

TABLE 15

| | Representative value of counts of protective wiping behaviors (max. counts, counts/min) | | | Representative value of counts of protective wiping behaviors (max. counts, counts/min) | |
|---|---|---|---|---|---|
| Example | 10 μg/ml | 30 μg/ml | Example | 10 μg/ml | 30 μg/ml |
| 1 |  | 10.0 | 42 | 11.0 | 15.2 |
| 2 |  | 16.8 | 43 | 8.2 | 9.4 |
| 3 |  | 21.2 | 44 | 6.0 | 12.6 |
| 4 |  | 7.2 | 45 | 7.0 | 11.0 |
| 5 |  | 22.8 | 46 | 8.8 | 9.8 |
| 6 | 14.8 | 21.2 | 49 |  | 21.8 |
| 7 | 7.0 | 12.8 | 51 |  | 23.6 |
| 8 |  | 18.0 | 52 | 8.4 | 10.4 |
| 9 |  | 24.0 | 54 | 6.4 | 9.8 |
| 10 | 10.2 | 14.2 | 56 |  | 11.6 |
| 11 |  | 18.8 | 59 |  | 18.0 |
| 12 |  | 18.2 | 60 |  | 18.6 |

TABLE 15-continued

| | Representative value of counts of protective wiping behaviors (max. counts, counts/min) | | | Representative value of counts of protective wiping behaviors (max. counts, counts/min) | |
|---|---|---|---|---|---|
| Example | 10 μg/ml | 30 μg/ml | Example | 10 μg/ml | 30 μg/ml |
| 13 | | 18.6 | 62 | | 15.8 |
| 14 | 17.8 | 21.2 | 65 | | 21.8 |
| 15 | 16.2 | 23.0 | 66 | | 21.8 |
| 16 | 5.2 | 19.2 | 68 | | 18.8 |
| 17 | | 18.2 | 69 | | 22.4 |
| 18 | | 22.0 | 70 | | 22.4 |
| 22 | 6.2 | 10.4 | 72 | 6.6 | 10.2 |
| 24 | 15.8 | 18.6 | 78 | | 22.8 |
| 25 | | 18.8 | 81 | | 18.6 |
| 26 | | 8.8 | 83 | | 9.4 |
| 27 | 10.6 | 9.4 | 84 | 9.2 | 13.0 |
| 28 | | 17.0 | 88 | | 9.0 |
| 30 | | 17.0 | 98 | | 18.6 |
| 31 | | 11.2 | | | |
| 32 | 8.4 | 14.4 | Capsaicin | 20.0 | |
| 34 | | 14.6 | Reference (solvent) | | 1.6 |
| 36 | | 12.8 | | | |

As shown in Table 15, frequent protective wiping behaviors were observed in the mice treated with 10 μg/ml capsaicin solution. On the other hand, it has been found that all the Example compounds shown in Table 15, which exhibited potent analgesic effect, exhibit weak irritancy since the counts of protective wiping behaviors following administration of the Example compounds were less even in case of the Example compounds in 30 μg/ml.

Experiment 3. Skin Sensitization Test (Evaluation of Allergenic Potency)

The purpose of the present experiment is to investigate if each administered compound of the invention may induce allergic contact dermatitis. In detail, the test was carried out using Freund's complete adjuvant (FCA) according to the Adjuvant and Patch Test [Sato, et al., Contact Dermatitis, 7, 225-237 (1981)], which is described in "Description of Guideline on Nonclinical Studies of Drugs (Iyakuhin Hirinshou-shiken Guideline Kaisetsu), Chapter 8, P.72-76, *Skin sensitization test*" [edited by the Ministry of Health and Welfare, Pharmaceutical Affairs Bureau, Yakuji-Nippou-sha (1997)]. Slc: Hartley male guinea-pigs were used for the test. As a test compound, each compound of the invention and DNCB (1-chloro-2,4-dinitrobenzene) as a positive control drug were dissolved in 70% ethanol/water solution and were administered to the animals. The 70% ethanol/water solution was used as vehicle solvent (reference).

In detail, after FCA emulsion was intradermally administered around the shaved back part of the guinea-pig as a pre-treatment, each patch containing 1% test compound solution or reference (solvent) solution was closedly attached once a day for consecutive 3 days in total (Primary Sensitization). On 7th day after the Primary Sensitization, 10% sodium lauryl sulfate ointment was openly applied at the same part for 24 hours, and then each patch containing 1% test compound solution or reference (solvent) solution was closedly attached again for 48 hours (Second Sensitization). 14 days after the Second Sensitization treatment, each test compound (maximum concentration: 1%) was applied for 24 hours using patch in the same manner (initiation). 24 and 48 hours after the application, the reaction (erythema, edema) on the applied skin part was observed and was scored (0-3) based on the criteria of Magnusson and Kligman [J. Invest. Dermatol., 52, 268-276 (1969)], and then the degree of skin sensitization induced by each of compound was evaluated. As the result, it has been found that the compounds of Examples 1, 2, 16, 22, 27, 43, 44, 45, and 46 have no skin sensitization and hence are acceptable to topical formulation.

Experiment 4: Skin Sensitization Test (Local Lymph Node Assay)

The purpose of the present experiment is to investigate if each administered compound of the invention can induce allergic contact dermatitis. In detail, the skin sensitization effect of the compounds of the invention was examined using BrdU (bromodeoxyuridine) by LLNA (Local Lymph Node Assay).

In more detail, the test was carried out according to the method by Suda, A. et al. (Local lymph node assay with non-radioisotope alternative endpoints. J. Toxicol. Sci., 27(3):205-218, 2002). Namely, the compounds of the invention were dissolved in DMF (N,N-dimethylformamide) to prepare 1 and 3% solutions, which were applied to both auricles of female CBA/JN mice aged 9 weeks for consecutive 3 days (1st day to 3rd day)(25 μl/one-side ear, once a day)

As positive control drugs, DNCB (dinitrochlorobenzene, a potently sensitizing drug) and HCA (α-hexylcinnamaldehyde, a weakly sensitizing drug) were used. After the final application was finished (on 3rd day), ALZET Osmotic Pump containing 100 μl of 200 mg/mL BrdU (releasing rate: 0.5 μl/hour) was implanted into the ventral skin under pentobarbital anesthesia, and BrdU was exposed sustainedly. On 9th day from starting day to apply the compounds of the invention, the animals were euthanized by cervical dislocation, and parotid lymph nodes of both their ears were taken out. The nodes were weighed and homogenized in PBS to prepare a single cell suspension which was measured by a blood test device: ADVIA (Bayer) to count the number of the cells. Next, the cells were immunofluorescently stained with FITC-labeled anti-BrdU antibody using a BrdU Flow Kit (BD Biosciences), which were measured and analyzed using a flow cytometer: FACS Calibur (Becton Dickinson) to give BrdU-positive cell percentage. And then, the BrdU-positive cell percentage was multiplied by the number of the node cells to give the number of the BrdU-positive cells. Additionally, on each parameter, the average value for the test compound group was divided by the average value for the reference (solvent) group to give a stimulation Index (SI). We judged that the compound had skin sensitization activity when the SI of BrdU-positive cell number was 2 or more, in principle.

As the result, among the compounds of the invention, it has been found that the compounds of Examples 1, 2, 8, 10, 16, 22, 26, 27, 36, and 42 exhibit weak skin sensitization.

INDUSTRIAL APPLICABILITY

The compounds of the invention and the physiologically acceptable salts thereof exhibit a potent analgesic effect but a weak irritancy, and hence they are useful as an analgesic agent and an anti-inflammatory agent, as well as a medicament for treating neuropathic pain such as diabetic neuropathic pain, postherpetic neuralgia, trigeminal neuralgia, and HIV-multiple neuropathic pain; and pain caused by rheumatoid arthritis, osteoarthritis and so on, for which existing analgesic agents are not sufficiently effective. Furthermore, the compounds are also useful as a medicament for treating and/or preventing migraine or cluster headache, pruritus, allergic and nonallergic rhinitis, overactive bladder, stroke, irritable bowel syndrome, respiratory disease such as asthma and chronic obstructive pulmonary disease, dermatitis, mucositis, gastric/duodenal ulcer, inflammatory bowel syndrome, diabetes, and obesity.

What is claimed is:

1. A N-substituted phenylacetamide derivative of the formula (I):

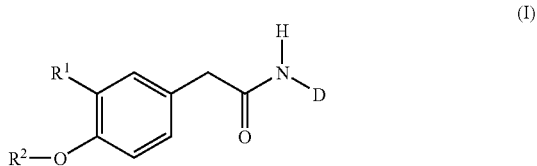

wherein
  $R^1$ is a methoxy group, a hydroxyl group, or a hydrogen atom;
  $R^2$ is a hydrogen atom, a $C_{1-4}$ alkyl group, a $C_{1-4}$ alkylcarbonyl group, or an arylcarbonyl group; and
  D is a group of the following formula (A), (B), or (C):

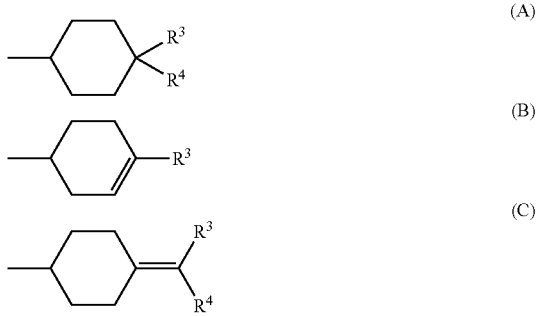

wherein
  $R^3$ is defined as a group of —X—Y—Z, wherein
  X is a single bond, a $C_{1-10}$ alkylene group, a $C_{2-10}$ alkenylene group or a $C_{2-10}$ alkynylene group;
  Y is a single bond, —O—, —O—C(=O)—, or —C(=O)—O—;
  Z is a straight or branched hydrocarbon group selected from the group consisting of a $C_{1-10}$ alkyl group, a $C_{2-10}$ alkenyl group, a $C_{2-10}$ alkynyl group, and a $C_{4-10}$ alkenyl-alkynyl group, in which the hydrocarbon may be optionally substituted with a $C_{3-8}$ cycloalkyl or an aryl; or a cyclic group selected from the group consisting of a $C_{3-8}$ cycloalkyl group, a $C_{3-8}$ cycloalkylidene-$C_{1-3}$ alkyl group, and an aryl group;
  the alkylene group, the alkenylene group, the alkynylene group, the alkyl group, the alkenyl group, the alkynyl group, and the alkenylalkynyl group in the above X and Z may be optionally substituted with 1-5 substituents selected from the group consisting of fluorine atoms and hydroxyl groups;
  the cycloalkyl group and the cycloalkyl moiety in the above Z may be optionally substituted with 1-5 substituents selected from the group consisting of fluorine atoms, hydroxyl groups, and $C_{1-6}$ alkyl groups;
  the aryl group and the aryl moiety in the above Z may be optionally substituted with 1-5 substituents selected from the group consisting of fluorine atoms, hydroxyl groups, $C_{1-6}$ alkyl groups optionally substituted with 1-5 fluorine atoms, $C_{1-6}$ alkoxy groups optionally substituted with 1-5 fluorine atoms, nitro groups, amino groups, cyano groups, $C_{1-4}$ alkyloxycarbonyl groups, $C_{1-4}$ alkylcarbonyloxy groups, carboxyl groups, and methylenedioxy groups;
  provided that X is a single bond and Z is not an aryl group when Y is a single bond; both X and Y are a single bond when Z is a $C_{3-8}$ cycloalkylidene-$C_{1-3}$ alkyl group; or X is a $C_{1-10}$ alkylene group when Y in the formula (B) or (C) is —O—;
  $R^4$ is a hydrogen atom, a hydroxyl group, a $C_{1-4}$ alkyl group, a $C_{2-4}$ alkenyl group, or a $C_{2-4}$ alkynyl group, provided that $R^4$ in formula (C) is not a hydroxyl group; alternatively
  $R^3$ and $R^4$ are taken together to form a $C_{3-8}$ cycloalkyl group or a saturated $C_{3-8}$ heteromonocyclyl group containing 1 or 2 oxygen atoms, each of which may be optionally substituted with 1-5 $C_{1-6}$ alkyl groups;
  further provided that $R^3$ and $R^4$ in formula (A) contain at least 3 carbon atoms in total; $R^3$ in formula (B) contains at least 3 carbon atoms; and $R^3$ and $R^4$ in formula (C) contain at least 2 carbon atoms in total,
  or a physiologically acceptable salt thereof.

2. The N-substituted phenylacetamide derivative of claim 1 wherein
  $R^1$ is a methoxy group, a hydroxyl group, or a hydrogen atom;
  $R^2$ is a hydrogen atom, a $C_{1-4}$ alkyl group, a $C_{1-4}$ alkylcarbonyl group, or an arylcarbonyl group; and
  D is a group of the following formula (A), (B), or (C):

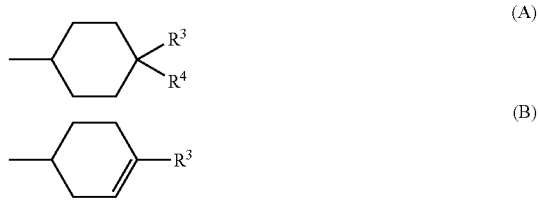

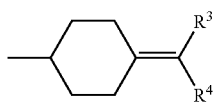

wherein
R³ is defined as a group of —X—Y—Z, wherein
X is a single bond, a $C_{1-10}$ alkylene group, or a $C_{2-10}$ alkenylene group;
Y is a single bond, —O—, —O—C(=O)—, —C(=O)—, or —C(=O)—O—;
Z is a straight or branched hydrocarbon group selected from the group consisting of a $C_{1-10}$ alkyl group, a $C_{2-10}$ alkenyl group, a $C_{2-10}$ alkynyl group, and a $C_{4-10}$ alkenyl-alkynyl group, in which the hydrocarbon may be optionally substituted with a $C_{3-8}$ cycloalkyl or an aryl; or a cyclic group selected from the group consisting of a $C_{3-8}$ cycloalkyl group, a $C_{3-8}$ tycloalkylidene-$C_{1-3}$ alkyl group, and an aryl group;
the alkylene group, the alkenylene group, the alkyl group, the alkenyl group, the alkynyl group, and the alkenylalkynyl group in the above X and Z may be optionally substituted with 1-5 substituents selected from the group consisting of fluorine atoms and hydroxyl groups;
the cycloalkyl group and the cycloalkyl moiety in the above Z may be optionally substituted with 1-5 substituents selected from the group consisting of fluorine atoms, hydroxyl groups, and $C_{1-6}$ alkyl groups;
the aryl group and the aryl moiety in the above Z may be optionally substituted with 1-5 substituents selected from the group consisting of fluorine atoms, hydroxyl groups, $C_{1-6}$ alkyl groups optionally substituted with 1-5 fluorine atoms, $C_{1-6}$ alkoxy groups optionally substituted with 1-5 fluorine atoms, nitro groups, amino groups, cyano groups, $C_{1-4}$ alkyloxycarbonyl groups, $C_{1-4}$ alkylcarbonyloxy groups, carboxyl groups, and methylenedioxy groups;
provided that X is a single bond and Z is not an aryl group when Y is a single bond; both X and Y are a single bond when Z is a $C_{3-8}$ cycloalkylidene-$C_{1-3}$ alkyl group; or X is a $C_{1-10}$ alkylene group when Y in the formula (B) or (C) is —O—;
R⁴ is a hydrogen atom, a hydroxyl group, a $C_{1-4}$ alkyl group, a $C_{2-4}$ alkenyl group, or a $C_{2-4}$ alkynyl group, provided that R⁴ in formula (C) is not a hydroxyl group;
alternatively
R³ and R⁴ are taken together to form a $C_{3-8}$ cycloalkyl group or a saturated $C_{3-8}$ heteromonocyclyl group containing 1 or 2 oxygen atoms, each of which may be optionally substituted with 1-5 $C_{1-6}$ alkyl groups;
further provided that R³ and R⁴ in formula (A) contain at least 3 carbon atoms in total; R³ in formula (B) contains at least 3 carbon atoms; and R³ and R⁴ in formula (C) contain at least 2 carbon atoms in total,
or a physiologically acceptable salt thereof.

3. The N-substituted phenylacetamide derivative of claim 1 wherein
R¹ is a methoxy group, a hydroxyl group, or a hydrogen atom;
R² is a hydrogen atom, a $C_{1-4}$ alkyl group, a $C_{1-4}$ alkylcarbonyl group, or an arylcarbonyl group; and D is a group of the following formula (A), (B), or (C):

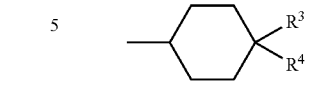

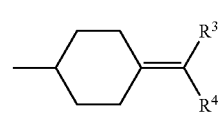

wherein
R³ is defined as a group of —X—Y—Z, wherein
X is a single bond, a $C_{1-10}$ alkylene group, or a $C_{2-10}$ alkenylene group;
Y is a single bond, —O—, —O—C(=O)—, —C(=O)—, or —C(=O)—O—;
Z is a straight or branched hydrocarbon group selected from the group consisting of a $C_{1-10}$ alkyl group and a $C_{2-10}$ alkenyl group, in which the hydrocarbon may be optionally substituted with a $C_{3-8}$ cycloalkyl or an aryl; or a cyclic group selected from the group consisting of a $C_{3-8}$ cycloalkyl group, a $C_{3-8}$ cycloalkylidene-$C_{1-3}$ alkyl group, and an aryl group;
the alkylene group, the alkenylene group, the alkyl group, and the alkenyl group in the above X and Z may be optionally substituted with 1-5 substituents selected from the group consisting of fluorine atoms and hydroxyl groups;
the cycloalkyl group and the cycloalkyl moiety in the above Z may be optionally substituted with 1-5 substituents selected from the group consisting of fluorine atoms, hydroxyl groups, and $C_{1-6}$ alkyl groups;
the aryl group and the aryl moiety in the above Z may be optionally substituted with 1-5 substituents selected from the group consisting of fluorine atoms, hydroxyl groups, $C_{1-6}$ alkyl groups optionally substituted with 1-5 fluorine atoms, $C_{1-6}$ alkoxy groups optionally substituted with 1-5 fluorine atoms, nitro groups, amino groups, cyano groups, $C_{1-4}$ alkyloxycarbonyl groups, $C_{1-4}$ alkylcarbonyloxy groups, carboxyl groups, and methylenedioxy groups;
provided that X is a single bond and Z is not an aryl group when Y is a single bond; both X and Y are a single bond when Z is a $C_{3-8}$ cycloalkylidene-$C_{1-3}$ alkyl group; or X is a $C_{1-10}$ alkylene group when Y in the formula (B) or (C) is —O—;
R⁴ is a hydrogen atom, a hydroxyl group, a $C_{1-4}$ alkyl group, a $C_{2-4}$ alkenyl group, or a $C_{2-4}$ alkynyl group, provided that R⁴ in formula (C) is not a hydroxyl group;
alternatively
R³ and R⁴ are taken together to form a $C_{3-8}$ cycloalkyl group or a saturated $C_{3-8}$ heteromonocyclyl group containing 1 or 2 oxygen atoms, each of which may be optionally substituted with 1-5 $C_{1-6}$ alkyl groups;
further provided that R³ and R⁴ in formula (A) contain at least 3 carbon atoms in total; R³ in formula (B) contains at least 3 carbon atoms; and R³ and R⁴ in formula (C) contain at least 2 carbon atoms in total,
or a physiologically acceptable salt thereof.

4. The N-substituted phenylacetamide derivative of claim 1 wherein
R¹ is a methoxy group, a hydroxyl group, or a hydrogen atom;
R² is a hydrogen atom, a $C_{1-4}$ alkyl group, a $C_{1-4}$ alkylcarbonyl group, or an arylcarbonyl group; and
D is a group of the following formula (A), (B), or (C):

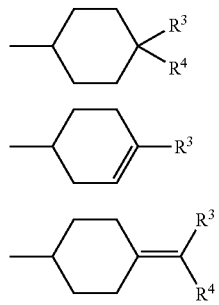

wherein
R³ is defined as a group of —X—Y—Z, wherein
X is a single bond, a $C_{1-10}$ alkylene group, or a $C_{2-10}$ alkenylene group;
Y is a single bond, —O—, —O—C(=O)—, —C(=O)—, or —C(=O)—O—;
Z is a straight or branched hydrocarbon group selected from the group consisting of a $C_{1-10}$ alkyl group and a $C_{2-10}$ alkenyl group, in which the hydrocarbon may be optionally substituted with a $C_{3-8}$ cycloalkyl or an aryl; or a cyclic group selected from the group consisting of a $C_{3-8}$ cycloalkyl group, a $C_{3-8}$ cycloalkylidene-$C_{1-3}$ alkyl group, and an aryl group;
the alkylene group, the alkenylene group, the alkyl group, and the alkenyl group in the above X and Z may be optionally substituted with 1-5 substituents selected from the group consisting of fluorine atoms and hydroxyl groups;
the cycloalkyl group and the cycloalkyl moiety in the above Z may be optionally substituted with 1-5 substituents selected from the group consisting of fluorine atoms, hydroxyl groups, and $C_{1-6}$ alkyl groups;
the aryl group and the aryl moiety in the above Z may be optionally substituted with 1-5 substituents selected from the group consisting of fluorine atoms, hydroxyl groups, $C_{1-6}$ alkyl groups optionally substituted with 1-5 fluorine atoms, $C_{1-6}$ alkoxy groups optionally substituted with 1-5 fluorine atoms, nitro groups, amino groups, cyano groups, $C_{1-4}$ alkyloxycarbonyl groups, $C_{1-4}$ alkylcarbonyloxy groups, carboxyl groups, and methylenedioxy groups;
provided that X is a single bond and Z is not an aryl group when Y is a single bond; both X and Y are a single bond when Z is a $C_{3-8}$ cycloalkylidene-$C_{1-3}$ alkyl group; or X is a $C_{1-10}$ alkylene group when Y in the formula (B) or (C) is —O—;
R⁴ is a hydrogen atom or a $C_{1-4}$ alkyl group; alternatively R³ and R⁴ are taken together to form a $C_{3-8}$ cycloalkyl group or a saturated $C_{3-8}$ heteromonocyclyl group containing 1 or 2 oxygen atoms, each of which may be optionally substituted with 1-5 $C_{1-6}$ alkyl groups;
further provided that R³ and R⁴ in formula (A) contain at least 3 carbon atoms in total; R³ in formula (B) contains at least 3 carbon atoms; and R³ and R⁴ in formula (C) contain at least 2 carbon atoms in total,
or a physiologically acceptable salt thereof.

5. The N-substituted phenylacetamide derivative of claim 1 wherein R³ is defined as a group of —X—Y—Z, and X is a single bond; or a physiologically acceptable salt thereof.

6. The N-substituted phenylacetamide derivative of claim 1 wherein R³ is defined as a group of —X—Y—Z, and Y is a single bond or —O—; or a physiologically acceptable salt thereof.

7. The N-substituted phenylacetamide derivative of claim 1 wherein R³ is defined as a group of —X—Y—Z, and both X and Y are a single bond; or a physiologically acceptable salt thereof.

8. The N-substituted phenylacetamide derivative of claim 1 wherein R³ and R⁴ are taken together to form a $C_{3-8}$ cycloalkyl group which may be optionally substituted with 1-5 $C_{1-6}$ alkyl groups; or a physiologically acceptable salt thereof.

9. The N-substituted phenylacetamide derivative of claim 1 wherein R³ and R⁴ in formula (A) contain 3-10 carbon atoms in total, R³ in formula (B) contains 3-10 carbon atoms, and R³ and R⁴ in formula (C) contain 2-9 carbon atoms in total; or a physiologically acceptable salt thereof.

10. The N-substituted phenylacetamide derivative of claim 1 wherein R³ and R⁴ in formula (A) contain 3-8 carbon atoms in total, R³ in formula (B) contains 3-8 carbon atoms, and R³ and R⁴ in formula (C) contain 2-7 carbon atoms in total; or a physiologically acceptable salt thereof.

11. The N-substituted phenylacetamide derivative of claim 1 wherein
R¹ is a methoxy group, a hydroxyl group, or a hydrogen atom;
R² is a hydrogen atom, a $C_{1-4}$ alkyl group, a $C_{1-4}$ alkylcarbonyl group, or an arylcarbonyl group; and
D is a group of the following formula (A), (B), or (C):

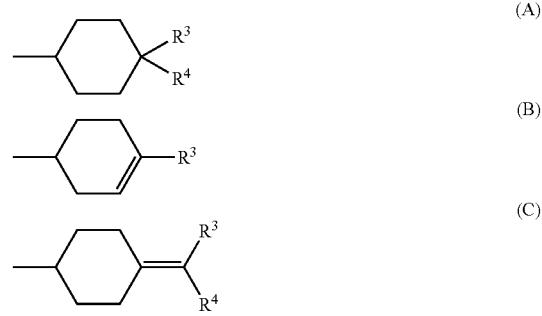

wherein
R³ is defined as a group of —X—Y—Z, wherein
X is a single bond;
Y is a single bond;
Z is a straight or branched hydrocarbon group selected from the group consisting of a $C_{1-7}$ alkyl group or a $C_{2-7}$ alkenyl group, in which the hydrocarbon may be optionally substituted with a $C_{3-8}$ cycloalkyl or an aryl; or a cyclic group selected from the group consisting of a $C_{3-8}$ cycloalkyl group, and a $C_{3-8}$ cycloalkylidene-$C_{1-3}$ alkyl group;
the alkyl group or alkenyl group in the above Z may be optionally substituted with 1-5 substituents selected from the group consisting of fluorine atoms and hydroxyl groups;

the cycloalkyl group and the cycloalkyl moiety in the above Z may be optionally substituted with 1-5 substituents selected from the group consisting of fluorine atoms, hydroxyl groups, and $C_{1-6}$ alkyl groups;

the aryl moiety in the above Z may be optionally substituted with 1-5 substituents selected from the group consisting of fluorine atoms, hydroxyl groups, $C_{1-6}$ alkyl groups optionally substituted with 1-5 fluorine atoms, $C_{1-6}$ alkoxy groups optionally substituted with 1-5 fluorine atoms, nitro groups, amino groups, cyano groups, $C_{1-4}$ alkyloxycarbonyl groups, $C_{1-4}$ alkylcarbonyloxy groups, carboxyl groups, and methylenedioxy groups;

$R^4$ is a hydrogen atom or a $C_{1-4}$ alkyl group; alternatively $R^3$ and $R^4$ are taken together to form a $C_{3-8}$ cycloalkyl group which may be optionally substituted with 1-5 $C_{1-6}$ alkyl groups;

further provided that $R^3$ and $R^4$ in formula (A) contain 3-10 carbon atoms in total; $R^3$ in formula (B) contains 3-10 carbon atoms; and $R^3$ and $R^4$ in formula (C) contain 2-9 carbon atoms in total, or a physiologically acceptable salt thereof.

12. The N-substituted phenylacetamide derivative of claim 1 wherein $R^1$ is a methoxy group, a hydroxyl group, or a hydrogen atom;

$R^2$ is a hydrogen atom, a $C_{1-4}$ alkyl group, a $C_{1-4}$ alkylcarbonyl group, or an arylcarbonyl group; and D is a group of the following formula (A), (B), or (C):

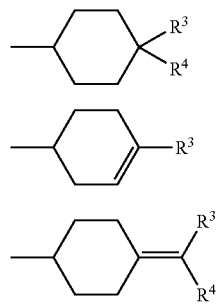

wherein $R^3$ is defined as a group of —X—Y—Z, wherein

X is a single bond;

Y is a single bond;

Z is a straight or branched hydrocarbon group selected from the group consisting of a $C_{1-7}$ alkyl group and a $C_{2-7}$ alkenyl group, in which the hydrocarbon may be optionally substituted with a $C_{3-8}$ cycloalkyl; or a cyclic group selected from the group consisting of a $C_{3-8}$ cycloalkyl group and a $C_{3-8}$ cycloalkylidene-$C_{1-3}$ alkyl group;

the alkyl group or alkenyl group in the above Z may be optionally substituted with 1-5 fluorine atoms;

$R^4$ is a hydrogen atom or a $C_{1-4}$ alkyl group; alternatively $R^3$ and $R^4$ are taken together to form a $C_{3-8}$ cycloalkyl group further provided that $R^3$ and $R^4$ in formula (A) contain 3-10 carbon atoms in total; $R^3$ in formula (B) contains 3 - 10 carbon atoms; and $R^3$ and $R^4$ in formula (C) contain 2-9 carbon atoms in total, or a physiologically acceptable salt thereof.

13. The N-substituted phenylacetamide derivative of claim 1 wherein $R^1$ is a methoxy group or a hydroxyl group, or a physiologically acceptable salt thereof.

14. The N-substituted phenylacetamide derivative of claim 1 wherein $R^2$ is a hydrogen atom, or a physiologically acceptable salt thereof.

15. The N-substituted phenylacetamide derivative of claim 1 wherein $R^1$ is a methoxy group, and $R^2$ is a hydrogen atom; or a physiologically acceptable salt thereof.

16. The N-substituted phenylacetamide derivative of any one of claims 1-15 wherein D is defined as formula (A), or a physiologically acceptable salt thereof.

17. The N-substituted phenylacetamide derivative of any one of claims 1-15 wherein D is defined as formula (B), or a physiologically acceptable salt thereof.

18. The N-substituted phenylacetamide derivative of any one of claims 1-15 wherein D is defined as formula (C), or a physiologically acceptable salt thereof.

19. The N-substituted phenylacetamide derivative of claim 1 wherein the compound of formula (I) is selected from the group consisting of N-(4-butyl-3-cyclohexenyl)-2-(4-hydroxy-3-methoxyphenyl)acetamide, N-(cis-4-butylcyclohexyl)-2-(4-hydroxy-3-methoxyphenyl)acetamide, N-(trans-4-butylcyclohexyl)-2-(4-hydroxy-3-methoxyphenyl)acetamide, 2-(4-hydroxy-3-methoxyphenyl)-N-(cis-4-pentylcyclohexyl)acetamide, 2-(4-hydroxy-3-methoxyphenyl)-N-(trans-4-pentylcyclohexyl)acetamide, N-(4-butylidenecyclohexyl)-2-(4-hydroxy-3-methoxyphenyl)acetamide, 2-(4-hydroxy-3-methoxyphenyl)-N-(4-pentylidene-cyclohexyl)acetamide, 2-(4-hydroxy-3-methoxyphenyl)-N-[4-(3-methyl-butylidene) cyclohexyl]acetamide, 2-(4-hydroxy-3-methoxyphenyl)-N-[4-(4-pentenylidene) cyclohexyl]acetamide, N-{trans-4-[(Z)-1-butenyl]cyclohexy}-2-(4-hydroxy-3-methoxyphenyl) acetamide, 2-(4-hydroxy-3-methoxyphenyl)-N-{trans-4-[(Z)-1-pentenyl]cyclohexyl}acetamide, 2-(4-hydroxy-3-methoxyphenyl)-N-{trans-4-[(Z)-1-propenyl]cyclohexyl} acetamide, 2-(4-hydroxy-3-methoxyphenyl)-N-{trans-4-[(Z)-4,4,4-trifluoro-1-butenyl]cyclohexyl}acetamide, 2-(4-hydroxy-3-methoxyphenyl)-N-[trans-4-(3-methylbutyl) cyclohexyl]acetamide, 2-(4-hydroxy-3-methoxyphenyl)-N-[trans-4-(4-methylpentyl) cyclohexyl]acetamide, N-[trans-4-(2-cyclopropylethyl)cyclohexyl]-2-(4-hydroxy-3-methoxyphenyl)acetamide, 2-(4-hydroxy-3-methoxyphenyl)-N-[trans-4-(2-methyl-propyl)cyclohexyl]acetamide, N-[trans-4-(cyclopentylmethyl)cyclohexyl]-2-(4-hydroxy-3-methoxyphenyl)acetamide, 2-(4-hydroxy-3-methoxyphenyl)-N-[trans-4-(3-methyl-2-butenyl)cyclohexyl]acetamide, 2-(4-hydroxy-3-methoxyphenyl)-N-[cis-4-(3-methyl-2-butenyl)cyclohexyl]acetamide, 2-(4-hydroxy-3-methoxyphenyl)-N-[cis-4-(3-methylbutyl)cyclohexyl]acetamide, N-{trans-4-[(E)-1-butenyl]cyclohexyl}-2-(4-hydroxy-3-methoxyphenyl)acetamide, 2-(4-hydroxy-3-methoxyphenyl)-N-{trans-4-[(E)-1-pentenyl]cyclohexyl}acetamide, 2-(4-hydroxy-3-methoxyphenyl)-N-{trans-4-[(E)-4-methyl-1-pentenyl]cyclohexyl}acetamide,
N-[trans-4-(2-cyclobutylethyl)cyclohexyl]-2-(4-hydroxy-3-methoxyphenyl)acetamide,
2-(4-hydroxy-3-methoxyphenyl)-N-{cis-4-[(E)-1-pentenyl]cyclohexyl}acetamide,
N-{cis-4-[(E)-1-butenyl]cyclohexyl}-2-(4-hydroxy-3-methoxyphenyl)acetamide,
2-(4-hydroxy-3-methoxyphenyl)-N-{cis-4-[(E)-3-methyl-1-butenyl]cyclohexyl}acetamide,
N-{cis-4-[(E)-2-cyclopropylvinyl]cyclohexyl}-2-(4-hydroxy-3-methoxyphenyl)acetamide,
2-(4-hydroxy-3-methoxyphenyl)-N-(cis-4-propylcyclohexyl)acetamide,
N-[cis-4-(3-cyclopropylpropyl)cyclohexyl]-2-(4-hydroxy-3-methoxyphenyl)acetamide,
2-(4-hydroxy-3-methoxyphenyl)-N-{trans-4-[(E)-3-methyl-1,3-butadienyl]cyclohexyl}acetamide,
2-(4-hydroxy-3-methoxyphenyl)-N-{trans-4-[(Z)-3-pentenyl]cyclohexyl}acetamide,
2-(4-hydroxy-3-methoxyphenyl)-N-{trans-4-[(E)-3-pentenyl]cyclohexyl}acetamide,
N-(4-cyclohexylidenecyclohexyl)-2-(4-hydroxy-3-methoxyphenyl)acetamide,
N-[4-(1-ethylpropylidene)cyclohexyl]-2-(4-hydroxy-3-methoxyphenyl)acetamide,
N-(4-cycloheptylidenecyclohexyl)-2-(4-hydroxy-3-methoxyphenyl)acetamide,
2-(4-hydroxy-3-methoxyphenyl)-N-(4-isopropylidenecyclohexyl)acetamide,
N-(trans-4-cyclohexylcyclohexyl)-2-(4-hydroxy-3-methoxyphenyl)acetamide,
2-(4-hydroxy-3-methoxyphenyl)-N-[trans-4-(3-pentyl)cyclohexyl]acetamide,
N-(trans-4-cyclobutylcyclohexyl)-2-(4-hydroxy-3-methoxyphenyl)acetamide,
N-(trans-4-cycloheptylcyclohexyl)-2-(4-hydroxy-3-methoxyphenyl)acetamide,
2-(4-hydroxy-3-methoxyphenyl)-N-[4-(3-pentyl)-3-cyclohexenyl]acetamide,
N-[4-(4-heptyl)-3-cyclohexenyl]-2-(4-hydroxy-3-methoxyphenyl)acetamide,
N-[trans-4-(2-ethyl-1-butenyl)cyclohexyl]-2-(4-hydroxy-3-methoxyphenyl)acetamide,
N-[trans-4-(cyclobutylidenemethyl)cyclohexyl]-2-(4-hydroxy-3-methoxyphenyl)acetamide,
N-[trans-4-(2-ethylbutyl)cyclohexyl]-2-(4-hydroxy-3-methoxyphenyl)acetamide,
N-[trans-4-(cyclobutylmethyl)cyclohexyl]-2-(4-hydroxy-3-methoxyphenyl)acetamide,
N-{trans-4-[(Z)-2-butenyl]cyclohexyl}-2-(4-hydroxy-3-methoxyphenyl)acetamide,
2-(4-hydroxy-3-methoxyphenyl)-N-[cis-4-(2-methylpropyl)cyclohexyl]acetamide,
N[trans-4-(3,3-dimethylbutyl)cyclohexyl]-2-(4-hydroxy-3-methoxyphenyl)acetamide,
2-(4-hydroxy-3-methoxyphenyl)-N-(spiro[5.5]undec-3-yl)acetamide, and
N-(4-butyl-4-ethylcyclohexyl)-2-(4-hydroxy-3-methoxyphenyl)acetamide;
or a physiologically acceptable salt thereof 20. The N-substituted phenylacetamide derivative of claim 1 wherein the compound of formula (I) is selected from the group consisting of
N-(4-butyl-3-cyclohexenyl)-2-(4-hydroxy-3-methoxyphenyl)acetamide,
N-(cis-4-butylcyclohexyl)-2-(4-hydroxy-3-methoxyphenyl)acetamide,
N-(trans-4-butylcyclohexyl)-2-(4-hydroxy-3-methoxyphenyl)acetamide,
2-(4-hydroxy-3-methoxyphenyl)-N-(cis-4-pentylcyclohexyl)acetamide,
2-(4-hydroxy-3-methoxyphenyl)-N-(trans-4-pentylcyclohexyl)acetamide,
N-(4-butylidenecyclohexyl)-2-(4-hydroxy-3-methoxyphenyl)acetamide,
N-{trans-4-[(Z)-1-butenyl]cyclohexyl}-2-(4-hydroxy-3-methoxyphenyl)acetamide,
2-(4-hydroxy-3-methoxyphenyl)-N-{trans-4-[(Z)-1-propenyl]cyclohexyl}acetamide,
2-(4-hydroxy-3-methoxyphenyl)-N-{trans-4-[(Z)-4,4,4-trifluoro-1-butenyl]cyclohexyl}acetamide,
2-(4-hydroxy-3-methoxyphenyl)-N-[trans-4-(3-methyl-butyl)cyclohexyl]acetamide,
2-(4-hydroxy-3-methoxyphenyl)-N-[trans-4-(4-methyl-pentyl)cyclohexyl]acetamide,
N-[trans-4-(2-cyclopropylethyl)cyclohexyl]-2-(4-hydroxy-3-methoxyphenyl)acetamide,
N-[trans-4-(cyclopentylmethyl)cyclohexyl]-2-(4-hydroxy-3-methoxyphenyl)acetamide,
2-(4-hydroxy-3-methoxyphenyl)-N-[trans-4-(3-methyl-2-butenyl)cyclohexyl]acetamide,
N-{trans-4-[(E)-1-butenyl]cyclohexyl}-2-(4-hydroxy-3-methoxyphenyl)acetamide,
2-(4-hydroxy-3-methoxyphenyl)-N-{trans-4-[(E)-1-pentenyl]cyclohexyl}acetamide,
2-(4-hydroxy-3-methoxyphenyl)-N-{trans-4-[(E)-4-methyl-1-pentenyl]cyclohexyl}acetamide,
2-(4-hydroxy-3-methoxyphenyl)-N-{cis-4-[(E)-1-pentenyl]cyclohexyl}acetamide,
N-{cis-4-[(E)-1-butenyl]cyclohexyl}-2-(4-hydroxy-3-methoxyphenyl)acetamide,
2-(4-hydroxy-3-methoxyphenyl)-N-{cis-4-[(E)-3-methyl-1-butenyl]cyclohexyl }acetamide,
2-(4-hydroxy-3-methoxyphenyl)-N-(cis-4-propylcyclohexyl)acetamide,
N-[4-(1-ethylpropylidene)cyclohexyl]-2-(4-hydroxy-3-methoxyphenyl)acetamide,
N-(trans-4-cyclohexylcyclohexyl)-2-(4-hydroxy-3-methoxyphenyl)acetamide,
2-(4-hydroxy-3-methoxyphenyl)-N-[trans-4-(3-pentyl)cyclohexyl]acetamide,
N-(trans-4-cycloheptylcyclohexyl)-2-(4-hydroxy-3-methoxyphenyl)acetamide,
2-(4-hydroxy-3-methoxyphenyl)-N-[4-(3-pentyl)-3-cyclohexenyl]acetamide, and
N-[4-(4-heptyl)-3-cyclohexenyl]-2-(4-hydroxy-3-methoxyphenyl)acetamide;
or a physiologically acceptable salt thereof.

21. The N-substituted phenylacetamide derivative of claim 1 wherein the compound of formula (I) is selected from the group consisting of
N-(4-butyl-3-cyclohexenyl)-2-(4-hydroxy-3-methoxyphenyl)acetamide,
N-(cis-4-butylcyclohexyl)-2-(4-hydroxy-3-methoxyphenyl)acetamide,
N-(trans-4-butylcyclohexyl)-2-(4-hydroxy-3-methoxyphenyl)acetamide,
2-(4-hydroxy-3-methoxyphenyl)-N-(cis-4-pentylcyclohexyl)acetamide,
2-(4-hydroxy-3-methoxyphenyl)-N-(trans-4-pentylcyclohexyl)acetamide, N-(4-butylidenecyclohexyl)-2-(4-hydroxy-3-methoxyphenyl)acetamide, N-{trans-4-[(Z)-1-butenyl]cyclohexyl}-2-(4-hydroxy-3-methoxyphenyl)acetamide, 2-(4-hydroxy-3-methoxyphenyl)-N-{trans-4-[(Z)-1-propenyl]cyclohexyl}acetamide, 2-(4-hydroxy-3-methoxyphenyl)-N-{trans-4-[(Z)-4,4,4-trifluoro-1-butenyl]cyclohexyl}acetamide, N-{trans-4-[(E)-1-butenyl]cyclohexyl}-2-(4-hydroxy-3-methoxyphenyl)acetamide, 2-(4-hydroxy-3-methoxyphenyl)-N-{trans-4-[(E)-1-pentenyl]cyclohexyl}acetamide, N-{cis-4-[(E)-1-butenyl]cyclohexyl}-2-(4-hydroxy-3-methoxyphenyl)acetamide, 2-(4-hydroxy-3-methoxyphenyl)-N-(cis-4-propylcyclohexyl)acetamide, N-[4-(1-ethylpropylidene)cyclohexyl]-2-(4-hydroxy-3-methoxyphenyl)acetamide, and 2-(4-hydroxy-3-methoxyphenyl)-N-[4-(3-pentyl)-3-cyclohexenyl]acetamide;

or a physiologically acceptable salt thereof.

22. A pharmaceutical composition comprising as an active ingredient the N-substituted phenylacetamide derivative of claim 1 or a physiologically acceptable salt thereof.

23. An analgesic agent or anti-inflammatory agent comprising as an active ingredient the N-substituted phenylacetamide derivative of claim 1 or a physiologically acceptable salt thereof.

24. A method for treating pain and/or inflammation, which comprises administering an effective amount of the N-substituted phenylacetamide derivative of claim 1 or a physiologically acceptable salt thereof to a patient in need thereof.

* * * * *